(12) United States Patent
Cantor et al.

(10) Patent No.: US 8,329,409 B2
(45) Date of Patent: Dec. 11, 2012

(54) METHODS, KITS, AND ANTIBODIES FOR DETECTING PARATHYROID HORMONE

(75) Inventors: Thomas L. Cantor, El Cajon, CA (US); Ping Gao, San Diego, CA (US)

(73) Assignee: Scantibodies Laboratory, Inc., Santee, CA (US)

( * ) Notice: Subject to any disclaimer, the term of this patent is extended or adjusted under 35 U.S.C. 154(b) by 366 days.

(21) Appl. No.: 11/894,367

(22) Filed: Aug. 20, 2007

(65) Prior Publication Data

US 2008/0069828 A1 Mar. 20, 2008

Related U.S. Application Data

(60) Continuation of application No. 11/799,726, filed on May 1, 2007, which is a division of application No. 10/617,489, filed on Jul. 10, 2003, which is a continuation-in-part of application No. 09/344,639, filed on Jun. 26, 1999, now Pat. No. 6,743,590, which is a continuation-in-part of application No. 09/231,422, filed on Jan. 14, 1999, now Pat. No. 6,689,566.

(51) Int. Cl.
*G01N 33/53* (2006.01)

(52) U.S. Cl. ........................................... 435/7.1

(58) Field of Classification Search ..................... None
See application file for complete search history.

(56) References Cited

U.S. PATENT DOCUMENTS

| | | | |
|---|---|---|---|
| 4,086,196 A | 4/1978 | Tregear |
| 4,208,479 A | 6/1980 | Zuk et al. |
| 4,369,138 A | 1/1983 | Lindall |
| 4,423,037 A | 12/1983 | Rosenblatt et al. |
| 4,508,828 A | 4/1985 | Lindall et al. |
| 4,517,290 A | 5/1985 | Iwasa et al. |
| 4,656,250 A | 4/1987 | Morita et al. |
| 4,751,284 A | 6/1988 | Forssmann |
| 4,782,044 A | 11/1988 | Forssmann |
| 4,824,777 A | 4/1989 | Chang et al. |
| 4,851,356 A | 7/1989 | Canfield et al. |
| 4,895,932 A | 1/1990 | Forssmann |
| 4,968,669 A | 11/1990 | Rosenblatt et al. |
| 5,026,653 A | 6/1991 | Lee et al. |
| 5,075,218 A | 12/1991 | Jette et al. |
| 5,093,233 A | 3/1992 | Rosenblatt et al. |
| 5,116,952 A | 5/1992 | Martin et al. |
| 5,208,041 A | 5/1993 | Sindrey |
| 5,256,543 A | 10/1993 | Pouletty et al. |
| 5,317,010 A | 5/1994 | Pang et al. |
| 5,354,900 A | 10/1994 | Matsuo et al. |
| 5,382,658 A | 1/1995 | Kronis et al. |
| 5,434,246 A | 7/1995 | Fukuda et al. |
| 5,496,801 A | 3/1996 | Holthuis et al. |
| 5,545,553 A | 8/1996 | Gotschlich |
| 5,589,452 A | 12/1996 | Krstenansky et al. |
| 5,639,617 A | 6/1997 | Bohuon |
| 5,656,455 A | 8/1997 | Wood et al. |
| 5,695,955 A | 12/1997 | Krstenansky et al. |
| 5,723,577 A | 3/1998 | Dong |
| 5,744,444 A | 4/1998 | Forsssmann |
| 5,747,456 A | 5/1998 | Chorev et al. |
| 5,783,558 A | 7/1998 | Duvos et al. |
| 5,792,455 A | 8/1998 | Chapman et al. |
| 5,798,225 A | 8/1998 | Krstenansky et al. |
| 5,807,823 A | 9/1998 | Krstenansky et al. |
| 5,840,831 A | 11/1998 | Hamachi et al. |
| 5,955,264 A | 9/1999 | Seed et al. |
| 5,958,384 A | 9/1999 | Holick et al. |
| 6,030,790 A | 2/2000 | Adermann et al. |
| 6,124,314 A | 9/2000 | Cameron et al. |
| 6,387,711 B1 | 5/2002 | Sundaram et al. |
| 6,524,788 B1 | 2/2003 | Cantor |
| 6,548,066 B1 * | 4/2003 | Michaeli et al. ........... 424/185.1 |
| 6,689,566 B1 | 2/2004 | Cantor et al. |
| 6,743,590 B1 | 6/2004 | Cantor |
| 6,756,480 B2 | 6/2004 | Kostenuik et al. |
| 6,838,264 B2 | 1/2005 | Zahradnik et al. |
| 7,056,655 B2 | 6/2006 | Cantor |
| 7,057,012 B1 | 6/2006 | Gardella et al. |
| 7,459,276 B2 | 12/2008 | Cantor et al. |

(Continued)

FOREIGN PATENT DOCUMENTS

DE 33 47 548 7/1985

(Continued)

OTHER PUBLICATIONS

Veprek et al. (J. Peptide Research 1999 vol. 5, p. 203-220).* Tam et al. (Method in Enzymology 1997 vol. 289, p. 612-628).*
Brossard et al., Journal of Clinical Endocrinology and Metabolism (1996) 81(11):3923-3929.
Gao et al., Clinica Chimica Acta (1996) 245:39-59.
Lepage et al., Clin. Chem. (1998) 44:805-810.
Magerlein et al., Arzneim.-Forsch./Drug Res. (1998) 48:197-204.
European Search Report for EP 06 00 8181, mailed on May 29, 2008, 14 pages.
Adermann et al., in: Innovations and Perspectives in Solid Phase Synthesis, Epton (ed.), Mayflower World Wide, Birmingham (1994) pp. 429-432.

(Continued)

*Primary Examiner* — Jacob Cheu
(74) *Attorney, Agent, or Firm* — Morrison & Foerster LLP

(57) ABSTRACT

The present invention relates to novel methods and compositions useful for detecting whole parathyroid hormone at a physiological level and parathyroid fragments in a mammalian sample. Such detections may be useful to different parathyroid diseases or disorders in a subject, such as hyperparathyroidism and related bone diseases, from normal or non-disease states. One detects whole or non-fragmented (1 to 84) parathyroid hormone in a biological sample and optionally one or more of a selection of non-whole parathyroid hormone peptide fragments that may or may not function as a parathyroid hormone antagonists. By either comparing values or using independently the value of either the one or more of a selection of non-whole parathyroid hormone peptide fragments, the whole parathyroid hormone, or the combination of these values one is able to differentiate parathyroid and bone related disease states, as well as differentiate such states from normal states.

9 Claims, 17 Drawing Sheets

U.S. PATENT DOCUMENTS

| | | | |
|---|---|---|---|
| 7,465,703 | B1 | 12/2008 | Cantor |
| 7,572,765 | B2 * | 8/2009 | Gardella ................. 514/1.1 |
| 7,723,042 | B2 | 5/2010 | Cantor et al. |
| 7,820,393 | B2 | 10/2010 | Cantor et al. |
| 7,851,163 | B2 | 12/2010 | Armbruster et al. |
| 7,892,749 | B2 | 2/2011 | Cantor et al. |
| 7,943,323 | B2 | 5/2011 | Cantor et al. |
| 2002/0025929 | A1 | 2/2002 | Sato |
| 2002/0110871 | A1 | 8/2002 | Zahradnik et al. |
| 2002/0160945 | A1 | 10/2002 | Cantor |
| 2003/0082179 | A1 | 5/2003 | Hutchison |
| 2003/0087822 | A1 | 5/2003 | Cantor |
| 2003/0138858 | A1 | 7/2003 | Cantor |
| 2003/0157560 | A1 | 8/2003 | Cantor |
| 2003/0171288 | A1 | 9/2003 | Stewart |
| 2003/0175802 | A1 | 9/2003 | Armbruster et al. |
| 2004/0014095 | A1 | 1/2004 | Gerber et al. |
| 2004/0067526 | A1 | 4/2004 | Cantor |
| 2004/0185536 | A1 | 9/2004 | Cantor |
| 2004/0219598 | A1 | 11/2004 | Cantor |
| 2004/0229281 | A1 | 11/2004 | Cantor |
| 2005/0003493 | A1 | 1/2005 | Hutchison |
| 2005/0026839 | A1 | 2/2005 | Gardella |
| 2005/0069952 | A1 | 3/2005 | Cantor et al. |
| 2005/0095236 | A1 | 5/2005 | Zahradnik et al. |
| 2005/0095631 | A1 | 5/2005 | Cantor |
| 2005/0170443 | A1 | 8/2005 | Cantor |
| 2005/0202506 | A1 | 9/2005 | Cantor |
| 2005/0260191 | A1 | 11/2005 | Zahradnik et al. |
| 2006/0024772 | A1 | 2/2006 | Hutchison |
| 2006/0035282 | A1 | 2/2006 | Cantor |
| 2006/0223119 | A1 | 10/2006 | Cantor |
| 2006/0286107 | A1 | 12/2006 | Hutchison |
| 2007/0098726 | A1 | 5/2007 | Cantor et al. |
| 2007/0287668 | A1 | 12/2007 | Cantor et al. |
| 2008/0069828 | A1 | 3/2008 | Cantor et al. |
| 2008/0108086 | A1 | 5/2008 | Cantor |
| 2009/0047686 | A1 | 2/2009 | Cantor |
| 2009/0094704 | A1 | 4/2009 | Zahradnik et al. |
| 2011/0009328 | A1 | 1/2011 | Gardella et al. |
| 2011/0300642 | A1 | 12/2011 | Cantor et al. |

FOREIGN PATENT DOCUMENTS

| | | |
|---|---|---|
| DE | 44 34 551 | 4/1996 |
| DE | 10 236 631 | 7/2003 |
| EP | 0 783 522 | 12/2001 |
| EP | 1 151 307 | 2/2007 |
| JP | 4132677 | 6/2008 |
| WO | WO-91/06564 | 5/1991 |
| WO | WO-93/06845 | 4/1993 |
| WO | WO-94/03201 | 2/1994 |
| WO | WO-96/10041 | 4/1996 |
| WO | WO-00/42437 | 7/2000 |
| WO | WO-01/44818 | 6/2001 |
| WO | WO-03/039572 | 5/2003 |
| WO | WO-2004/011607 | 2/2004 |
| WO | WO-2004/028444 | 4/2004 |
| WO | WO-2004/031727 | 4/2004 |
| WO | WO-2004/067021 | 8/2004 |
| WO | WO 2004067021 * | 8/2004 |
| WO | WO-2005/018413 | 3/2005 |

OTHER PUBLICATIONS

Aka et al., International Journal of Adolescent Medicine and Health (2000) 12(4):331-335.
Atkinson et al., Journal of Immunoassay (1982) 3(1):31-51.
Berson et al., J. Clin. Invest. (1956) 35:170-190.
Berson et al., PNAS USA (1963) 49:613-617.
Bhaskaran and Ponnuswamy, Int. J. Pept. Protein Res. (1988) 32:242-255.
Blind et al., Clin. Chem. (1987) 33(8):1376-1381.
Born et al., Endocrinology (1988) 123(4):1848-1853.
Born et al., Mol. Endocrinol. (1987) 1:5-14.
Bouillon et al., Clin. Chem. (1990) 36(2):271-276.
Bowie et al., Science (1990) 247:1306-1310.
Bringhurst et al., Am. J. Physiol. (1988) 255(6 Pt 1):E886-93.
Bringhurst et al., Endocrinology (1981) 108:103-108.
Broadus et al., J. Clin. Invest. (1977) 60:771-783.
Brossard et al., J. Bone and Miner. Res. (1999) 14:S444.
Brossard et al., Journal of Clinical Endocrinology and Metabolism (1993) 77:413-419.
Caetano et al., Equus Genome Res. (1999) 9(12):1239-1249.
Campbell et al., Laboratory Techniques in Biochemistry and Molecular Biology (1986) vol. 13, pp. 1-19.
Campbell, Monoclonal Antibody and Immunosensor Technology, in Laboratory Techniques in Biochemistry and Molecular Biology, van der Vliet (ed.), Elsevier (1991) pp. 1-11, 42-45.
Canfield et al., Endocrinology (1982) 110(5):1555-1563.
Canterbury et al., J. Clin. Invest. (1975) 55:1245-1253.
Cantor, Kidney Int. (2004) 66:461.
Caporale and Rosenblatt, Paraththyroid Hormone Antagonists Effective in vivo, in: Advances in Experimental Medicine and Biology, New York (1986) pp. 315-327.
Cardinal et al., J. of Clinical Endocrinology & Metabolism (1998) 83(11):3839-3844.
Cavaco et al., Journal of Endocrinological Investigation (1999) 22(11):829-834.
Clinical Chemistry (1999) 45(6)Suppl:A97 b, Abstract Nos. 339-341.
Coen et al., J. Lab. Clin. Med. (1993) 122:103-109.
Cohen Solal et al., J. of Clinical Endocrinology & Metabolism (1991) 73(3):516-524.
Colford et al., Clin. Chem. (1997) 43(6):S189 (381).
Colford et al., J. Bone & Miner. Res. (1997) 12(Supp. 1):S318 (F368).
Colford et al., 10th International Congress of Endocrinology Program and Abstracts (1996), entitled "Data Suggesting the Presence of a Circulating Inhibitor to PTH".
Colford et al., Meeting of the Endocrine Society (1996), entitled "Comparing Specificity for Intact Human Parathyroid Hormone Between INCSTAR PTHSP and Nichols Intact PTH Assays".
Colford 1997 Abstract Presentation.
Colford et al., The Endocrine Society, Programs & Abstracts, 79th Annual Meeting, Jun. 11-14, 1997, Minneapolis Minnesota, "Isolation and Characterization of Large Molecular Weight Fragments of PTH".
Corbetta et al., Clinical Endocrinology (2000) 52(3):339-348.
Dambacher et al., Clinical Science (1979) 57:435-443.
D'Amour et al., Am. J. Physiol. (1986) 251:E680-E687.
D'Amour et al., Clin. Chem. (2003) 49:2037-2044.
D'Amour et al., Clin. Chem. (2005) 51:169-176.
D'Amour et al., Endocrinology (1985) 117:127-134.
D'Amour et al., J. Bone Miner. Res. (1996) 11:1075-1085.
D'Amour et al., J. Clinical Endocrinology & Metabolism (1992) 74(3):525-532.
D'Amour et al., J. Clinical Endocrinology & Metabolism (2006) 91(1):283-289.
D'Amour et al., J. Immunoassay (1989) 10:191-205.
D'Amour et al., Kidney International (2005) 68:998-1007.
D'Amour, Kidney International (2006) 70:S29-S33.
Daniel et al., Virology (1994) 202:540-549.
Deleage and Roux, Protein Engineering (1987) 1:289-294.
Delmas et al., Molecular Immunology (1985) 22:675-679.
Desplan et al., The Lancet (Jul. 1977):198-199.
Estepa et al., Equine Vet J. (2003) 35:291-295.
Estepa et al., Nephrol. Dial. Transplant (2003) 18:1101-1107.
Fine and Zacharias, Kidney Int. (2002) 61:2210-2217.
Fischer et al., The Journal of Clinical Investigation (1974) 54:1382-1394.
Fiskin et al., The Journal of Biological Chemistry (1977) 252:8261-8268.
Flueck et al., Proceedings of the 58th American Meeting of the Endocrine Society, Jun. 1976.
Fournier et al., J. of Clinical Endocrinology & Metabolism (2001) 86(4):1840-1841.
Fournier et al., Kidney Int. (2002) 61(3):1181.
Fournier et al., Nephrol. Dial. Transplant. (1999) 14:2772-2774.
Freitag et al., New England Journal of Medicine (1978) 298:29-32.
Fuhr et al., Klin Wochenschr (1955) 33:729-730.

Fujimori et al., Endocrinology (1992) 130:29-36.
Fujimori et al., Therapeutic Apheresis and Dialysis (2004) 8(6):474-479.
Gallagher et al., J. Lab. Clin. Med. (1980) 95:373-385.
Gao et al., J. Bone Mineral Res. (2001) 16:605-614.
Gao et al., "Recognition of the PTH(7-84) Fragment by 5 Commercial PTH 'Sandwich' Assays" presented at the ASBMR 22$^{nd}$ Annual Meeting, Sep. 22-26, 2000, Toronto, Canada.
Gardella et al., J. Biol. Chem. (1991) 266:13141-13146.
Gardella et al., J. Biol. Chem. (1995) 270:6584-6588.
Ghillani et al., Cancer Res. (1989) 49(23):6845-6851.
Goltzman et al., J. Clin. Invest. (1980) 65:1309-1317.
Goltzmann et al., Journal of Biological Chemistry (1975) 250:3199-3203.
Goodman et al., J. of Clinical Endocrinology & Metabolism (2001) 86(4):1841-1842.
Goodman et al., Nephrol. Dial. Transplant. (2002) 17:1731-1736.
Gordon et al., Parathyroid Hormone Domain for Protein Kinase C Stimulation Located within Amphiphilic Helix, in: Peptides: Chemistry and Biology, Proceedings of the Twelfth American Peptide Symposium, Jun. 16-21, 1991, Cambridge, MA, Smith and Rivier (eds.) Escom Science Publishers (1992) pp. 37-39.
Gronwald et al., Biol. Chem. (1996) 377:175-186.
Habener and Potts, Endocrinology (1979) 105:115-119.
Habener and Potts, New England Journal of Medicine (1978) 299:580-585, 635-644.
Habener et al., Endocrine Research Comminications (1974) 1:1-17.
Habener et al., Nature New Biology (1972) 238:152-154.
Hanley and Wellings, Journal of Immunoassay (1985) 6:245-259.
Harlow and Lane, Antibodies: A Laboratory Manual, Cold Spring (1988) pp. 313-315.
Harlow and Lane, Antibodies: A Laboratory Manual, Cold Spring Harbor (1988) p. 612.
Harlow et al., Antibodies, 1988, pp. 366, 428, 584, and 579.
Harvey et al., Journal of Biological Chemistry (1999) 274(33):23249-23255.
Hashimoto et al., Journal of Cardiovascular Pharmacology (1981) 3(4):668-676.
Hehrmann et al., Journal of Immunoassay (1980) 1(2):151-174.
Hendy et al., Proceedings of the Society for Endocrinology 26P-27P.
Henikoff et al., PNAS USA (1992) 89:10915-10919.
Hopp and Woods, PNAS USA (1981) 78:3824-3828.
Horiuchi et al., Am. J. Physiol. (1983) 244(6):E589-95.
Huan et al., J. Am. Soc. Nephrol. (2006) 17:1923-1930.
Janeway et al., Immunobiology, 5$^{th}$ ed., Appendix I, pp. 624-625.
Janin, Nature (1979) 277:491-492.
Jara et al., Journal of Bone and Mineral Research (1994) 9(10):1629-1633.
Jensen et al., Clinical Chemistry (1996) 42(6):S172 Abstract 320 "Comparing Specificity for Intact Human Parathyroid Hormone Between INCSTAR PTHSP and Nichols Intact PTH Assays".
Jensen et al., poster from the 1996 Annual Meeting of the Endocrine Society, San Francisco, CA, entitled "Comparing Specificity for Intact Human Parathyroid Hormone Between INCSTAR PTHSP and Nichols Intact PTH Assays".
K/DOQI Clinical Practice Guidelines for Bone Metabolism and Disease in Chronic Kidney Disease, Draft Guideline Statements and Treatment Algorithms, Feb. 2003.
Kao et al., Clin. Chem. (1982) 28:69-74.
Kazama et al., Nephrol. Dial. Transplant. (2004) 19:892-897.
Keutmann et al., Biochemistry (1978) 17:5723-5729.
Keutmann et al., Endocrinology (1985) 117(3):1230-1234.
Kifor et al., J. Clin. Endocrinology Metab. (2003) 88:60-72.
Kifor et al., J. Clin. Endocrinology Metab. (2003) 88:4455-4464.
Kifor et al., J. Clin. Endocrinology Metab. (2004) 89:548-556.
Kohler and Milstein, Nature (1975) 256:495-497.
Kohno et al., J. Clin., Lab. Anal. (1998) 12:268-275.
Kunii and Vieira, Braz. J. Med. Biol. Res. (2001) 34(12):1547-1550.
Kuriyama et al., Blood Purification (1998) 16:43-48.
Kyte and Doolittle, J. Mol. Biol. (1982) 157:105-132.
Lafferty, Medicine (1966) 45:247-260.
Lei et al., J. Biol. Chem. (1995) 270(20):1182-1186.

Logue et al., Journal of Immunological Methods (1991) 137:159-166.
Loveridge et al., Endocrinology (1991) 128(4):1938-1946.
Magerlein et al., Arzneim.-Forsch./Drug Res. (1998) 48(1):197-204.
Magerlein et al., Arzneim.-Forsch./Drug Res. (1998) 48(II):783-787.
Magerlein et al., Calcified Tissue International (1995) 56:471 Abstract 193.
Magerlein et al., European Journal of Pharmaceutical Sciences (1994) vol. 2 pt. ½ at 154.
Magerlein, Ph.D. Dissertation, Oct. 31, 1995, Ruprecht Karls University of Heidelberg (Original in German).
Magerlein, Ph.D. Dissertation, Oct. 31, 1995, Ruprecht Karls University of Heidelberg (English Translation).
Mallette et al., J. Clin. Endocrinology Metab. (1982) 54:1017-1024.
Mallette, Journal of Clinical Endocrinology and Metabolism (1980) 50(1):201-203.
Mallette, Ligand Review (1979) 1:18-19.
Malluche, The Importance of Bone Health in ERSD: Out of the Frying Pan, Into the Fire?, World Congress on Nephrology, Berlin, Germany, Jun. 2003.
Marx et al., Journal of Biological Chemistry (1995) 270:15194-15202.
Marx, Medical Progress (2000) 343:1863-1875.
Mayer et al., Endocrinology (1979) 104:1778-1784.
Merrifield et al., Biochemistry (1982) 21:5020.
Mittal et al., Kidney International (1999) 55(5):1912-1919.
Monier-Faugere et al., Journal of the American Society of Nephrology (1999) 11:1093-1099.
Monier-Faugere et al., Kidney Int. (2001) 60:1460-1468.
Moreau et al., Bioinformatics (2006) 22:1088-1095.
Motte et al., Journal of Immunology (1987) 138(10):3332-3338.
Nakamura et al., Endocrinol. JPN (1981) 28(4):547-549.
Neer et al., J. Clin. Endocrinol. Metab. (1977) 44(2):420-423.
Ngo et al., The Protein Folding Problem and Tertiary Structure Prediction, Merz et al., (eds.), Birkhäuser Boston (1994) pp. 492-495.
Nguyen-Yamamoto et al., Eur. J. Endocrinol. (2002) 147:123-131.
Niall et al., PNAS USA (1969) 64:771-778.
Niall et al., Proc. Natl. Acad. Sci. USA (1974) 71(2):384-388.
Nissenson et al., J. Biol. Chem. (1988) 263(26):12866-12871.
Nussbaum et al., Chemical Abstracts (1982) 96(5):181-192.
Nussbaum et al., Clin. Chem. (1988) 33(8):1364-1367.
Nussbaum et al., Methods in Enzymology (1985) 109:625-638.
Pang et al., Pharmacol. Exp. Ther. (1981) 216(3):567-571.
Parthemore et al., J. Clin. Endocrinol. Metab. (1978) 47(2):284-289.
Pellegrini et al., The Journal of Biological Chemistry (1998) 273:10420-10427.
Podbesek et al., Endocrinology (1983) 112:1000-1006.
Qi et al., Am. J. Kidney Dis. (1995) 26:622-631.
Quarles et al., J. Clin. Endocrinol. Metab. (1992) 75:145-150.
Rabbani et al., J. Biol. Chem. (1984) 259:2949-2955.
Raisz et al., Annals International Medicine (1979) 91:739-740.
Rapley et al., Immunology (1993) 78:379-386.
Reeve et al., Br. Med. J. (1980) 280:1340-1344.
Regenmortel et al., Methods in Enzymology (1996) 9:465-472.
Richards et al., Clin. Nephrol. (1999) 51(2):126-127.
Rich et al., Clinical Immunology Principles and Practice (Mosby) (2$^{nd}$ ed. 2001) at 14.4.
Rodbard and Hutt, "Statistical Analysis of Radioimmunoassays and Immunoradiometric (labeled antibody) Assays" in Assays, Radioimmunoassays and Related Procedures in Medicine, vol. 1, Vienna: International Atomic Energy Agency, Vienna, (1974) pp. 165-192.
Rodbard et al., J. Clin. Endocrinology Metab. (1968) 28:1412-1418.
Roos et al., J. Clin. Endocrinology and Metab. (1981) 53:709-721.
Rosenblatt et al., Biochemistry (1981) 20(25):7246-7250.
Rosenblatt et al., Endocrinology (1978) 103(3):978-984.
Rucinski et al., Calcif. Tissue Int. (1995) 56:83-87.
Salomon et al., Pediatr. Nephrol. (2001) 16:1011-1014.
Sanchez and Salusky, Adv. Ren. Replace. Ther. (1996) 3:14-23 (Abstract only).
Santamaria et al., Kidney Int. (2003) 64:1867-1873.
Schultz et al., Bone and Mineral (1994) 27:121-132.
Schultz et al., Journal of Bone and Mineral Research (1993) 8(Supp. 1):S202.

Segre et al., American Journal of Medicine (1974) 56:774-784.
Segre et al., Biochemistry (1977) 16:2417-2427.
Segre et al., Endocrinology (1985) 116(3):1024-1029.
Segre et al., J. Clin. Invest. (1981) 67:439-448.
Segre et al., J. Clin. Invest. (1981) 67:449-457.
Segre et al., J. Clin. Invest. (1972) 51:3163-3172.
Segre et al., Methods Enzymol. (1975) 37(Pt. B):38-66.
Shigeno et al., Journal of Biological Chemistry (1988) 263:3864-3871.
Silverberg et al., J. Clin. Endocrinology Metab. (2003) 88:4725-4730.
Silverman and Yalow, J. Clin. Invest. (1973) 52:1958-1971.
Slatopolsky et al., Journal of American Society of Nephrology (1999) 10:625A.
Slatopolsky et al., Kidney Int. (2000) 58:753-761.
Souberbielle et al., J. Clin. Endocrinology Metab. (2001) 86:3086-3090.
Stadler, Homologous Radioimmunoassay for Human Parathyroid Hormone (Residues 1-34) with Biotinylated Peptide as Tracer, in Calcium Regulating Hormones, Vitamin D Metabolites, and Cyclic AMP Assays and their Clinical Application, Schmidt-Gayk et al., (eds.), Berlin/Heidelberg, Springer, (1990) pp. 137-150.
Stafford-Johnson et al., J. Comput. Assist. Tomogr. (1998) 22(2):295-299.
Stevens et al., Journal of Immunological Methods (1988) 108:271-278.
Stewart et al., J. Clin. Invest. (1988) 81(2):596-600.
Stryer, (ed.), Biochemistry $2^{nd}$ ed., (1981) pp. 13-16.
Sukovaty et al., Journal of Pharmaceutical and Biomedical Analysis (2006) 42:261-271.
Takano et al., Acta Endocrinologica (1988) 118:551-558.
Tam et al., PNAS USA (1988) 85(15):5409-5413.
Tampe et al., J. Immunoassay (1992) 13(1):1-13.
Thompson et al., PNAS USA (1988) 85(15):5673-5677.
Tizard, Immunology, An Introduction (Saunders College Publishing) $3^{rd}$ ed. (1992) p. 17.
Travis, (ed.), "Clinical Radioimmunoassay" in State-of-the-Art Scientific Newsletter, Inc., Anaheim, CA 92803, (1980) pp. 13-16.
Tregear et al., Endocr. Res. Commun. (1975) 2(8):561-570.
Uddin et al., Clinical Chemistry (1999) 45:A97 (340).
Vieira et al., Brazilian J. Med. Biol. Res. (1987) 20:721-729.
Visser et al., Acta Endocrinology (1979) 90:90-102.
Waller et al., Pediatr. Nephrol. (2003) 18:1242-1248.
Waller et al., Pediatr. Nephrol. (2005) 20:197-199.
Waller et al., "What is the parathyroid hormone level?" pamphlet.
Watson et al., Molecular Biology of the Gene, $4^{th}$ edition, (1987) The Bejamin/Cummings Pub. Co., p. 224.
Wingender et al., Structure-Function Relationship in Parathyroid Hormone in: Advances in Protein Design, International Workshop, Blöcker et al. (eds.), VCH (1988) pp. 167-176.
Wood et al., J. Clin. Chem. Biochemistry (1980) 18:789-795.
Wood et al., PNAS USA (1985) 82:1585-1588.
Woodhead, Clin. Biochem. (1990) 23:17-21.
Xie and Abou-Samra, Endocrinology (1998) 139:4563-4567.
Yamashita et al., Ann. Surg. (2002) 236:105-111.
Yamashita et al., Eur. J. Endocrinol. (2003) 149:301-306.
Yamashita et al., Surgery (2004) 135:149-156.
Yates et al., J. Clin. Invest. (1988) 81(3):932-938.
Zahradnik et al., Clinical Chemistry (1986) 32(6):1154.
Zanelli et al., Journal of Immunoassay (1983) 4(2):175-206.
Allegro Intact PTH, directional insert for PTH kit by Nichols Institute.
Nichols Advantage Bio-Intact PTH (1-84), Directional Insert for the test kit.
Receipt stamp from the National Diet Library of Japan showing that the Sep. 1994 issue of the European Journal of Pharmaceutical Sciences was received by the library on Sep. 26, 1995.
Note from the Bibliotheque Interuniversitaire de Pharmacie in Paris indicating that the library received the Sep. 1994 issue of the European Journal of Pharmaceutical Sciences on Sep. 27, 1994.
The copied register received from the Bibliotheque Universitaire Lyon, France indicating that the library received the Sep. 1994 issue of the European Journal of Pharmaceutical Sciences on Sep. 21, 1994.
U.S. Appl. No. 09/231,422, filed Jan. 14, 1999.
Office Action from U.S. Appl. No. 09/231,422, mailed on Sep. 20, 2000.
Amendment from U.S. Appl. No. 09/231,422, filed Feb. 7, 2001.
Supplemental Amendment from U.S. Appl. No. 09/231,422, filed Jul. 11, 2001.
Supplemental Amendment Under 37 C.F.R. § 1.111 from U.S. Appl. No. 09/231,422, filed May 20, 2002.
Amendment Under 37 C.F.R. § 1.111 from U.S. Appl. No. 09/231,422, filed Jan. 14, 2003.
Notice of Allowance and Interview Summary from U.S. Appl. No. 09/231,422, mailed on Feb. 12, 2003.
Amendment Under 37 C.F.R. § 1.312 from U.S. Appl. No. 09/231,422, filed May 2, 2003.
Comments on Statements of Reasons for Allowance from U.S. Appl. No. 09/231,422, filed May 2, 2003.
Response to Rule 312 Communication from U.S. Appl. No. 09/231,422, mailed on Dec. 5, 2003.
Request for Ex Parte ReExamination of United States Patent No. 6,689,566, filed Aug. 22, 2005.
Declaration of John Colford.
Order Granting Request for Ex Parte Reexamination for U.S. Patent No. 6,689,566, mailed on Sep. 14, 2005, control No. 90/007,685.
Request for Ex Parte Reexamination of U.S. Patent 6,689,566 per Rule 1.501 et seq., filed on Sep. 28, 2005 by Immutopics.
Order Granting Request for Reexamination of U.S. Patent 6,689,566, mailed on Oct. 27, 2005, control No. 90/007,732.
Decision Merging Reexamination Proceedings Control No. 90/007,685 and 90/007,732, mailed on Feb. 16, 2006.
Office Action in the Reexamination of US Patent No. 6,689,566, Control Nos. 90/007,685 and 90/007,732, mailed on Apr. 20, 2006.
Office Action in Ex Parte Reexamination of US Patent No. 6,689,566, Control No.'s 90/007,685 and 90/007,732, mailed on May 24, 2006.
Ex Parte Reexamination Interview Summary, Jun. 5, 2006.
Ex Parte Reexamination Interview Summary, Jul. 10, 2006.
Amendment in Response to Non-Final Office Action (and Exhibits 1-12 and Replacement Sheet Figure 5), filed in the Ex Parte Reexamination of US Patent No. 6,689,566, Control No.'s 90/007,685 and 90/007,732, filed on Jul. 24, 2006.
Final Office Action, from the Reexamination of U.S. Patent No. 6,689,566, Control Nos. 90/007,685 and 90/007,732, mailed on Sep. 21, 2006.
Notice of Litigation Activity, submitted by the third party requestor, Oct. 6, 2006.
Response to Final Office Action from the Reexamination of U.S. Patent No. 6,689,566, Control Nos. 90/007,685 and 90/007,732, filed on Nov. 10, 2006.
Supplemental Response to Final Office Action, from the Reexamination of United States Patent No. 6,689,566, having Control Nos. 90/007,685 and 90/007,732, filed Nov. 20, 2006.
Second Supplemental Response to Final Office Action from the Reexamination of United States Patent No. 6,689,566, having Control Nos. 90/007,685 and 90/007,732, filed Dec. 1, 2006.
Notice of Intent to Issue Ex Parte Reexamination Certificate, from the Reexamination of US Patent No. 6,689,566, Control No.'s 90/007,685 and 90/007,732, mailed Jan. 8, 2007.
Statement of Substance of Interview, from Control No. 90/007,685 and 90/007,732, filed on Jun. 29, 2007.
Statement of Substance of Interview from Reexamination Control No.'s 90/007,685 and 90/007,732, filed Nov. 26, 2007.
Miscellaneous Communication from Reexamination Control No.'s 90/007,685 and 90/007,732, mailed on Nov. 30, 2007.
Decision on Petition from the Reexamination of U.S. Patent No. 6,689,566, Control Nos. 90/007,685 and 90/007,732, mailed on Feb. 11, 2008.
Decision Returning Papers from the Reexamination of U.S. Patent No. 6,689,566, Control Nos. 90/007,685 and 90/007,732, mailed on Feb. 11, 2008.

Statement of Substance of Interview from the Reexamination of U.S. Patent No. 6,689,566, Control Nos. 90/007,685 and 90/007,732, filed on Mar. 6, 2008.
Decision on Petition, from 90/007,685 and 90/007,732, mailed on Apr. 3, 2008.
Statement of Substance of Interview from 90/007,685 and 90/007,732, filed May 15, 2008.
Office Action for U.S. Appl. No. 09/344,639 mailed on Sep. 20, 2000.
Petition for Extension of time of Two Months and Amendment for U.S. Appl. No. 09/344,639, dated Feb. 7, 2001.
Declaration of Dr. Ping Gao dated Feb. 7, 2001.
Supplemental Amendment for U.S. Appl. No. 09/344,639 dated Jul. 11, 2001.
Supplemental Amendment Under 37 CFR 1.111 for U.S. Appl. No. 09/344,639 dated May 20, 2002.
Second Supplemental Amendment for U.S. Appl. No. 09/344,639 dated Mar. 18, 2003.
Third Supplemental Amendment for U.S. Appl. No. 09/344,639 dated Mar. 28, 2003.
Notice of Allowability for U.S. Appl. No. 09/344,639 mailed on Apr. 7, 2003.
Interview Summary for U.S. Appl. No. 09/344,639 dated Mar. 11, 2003.
Amendment Under 37 CFR 1.312 for U.S. Appl. No. 09/344,639, dated Jul. 8, 2003.
Comments on Statements of Reasons for Allowance for U.S. Appl. No. 09/344,639, dated Jul. 8, 2003.
Office Communication for U.S. Appl. No. 09/344,639 mailed on Dec. 29, 2003.
U.S. Appl. No. 09/636,531, filed Aug. 10, 2000 by Thomas Cantor.
Petition to Make Special from U.S. Appl. No. 10/617,489, filed Dec. 30, 2003.
Statement of Substance of Interview from U.S. Appl. No. 10/617,489, filed Nov. 12, 2004.
Office Action from U.S. Appl. No. 10/617,489, mailed on Jan. 24, 2005.
Amendment in Response to Non-Final Office Action from U.S. Appl. No. 10/617,489, filed Mar. 28, 2005.
Supplemental Amendment from U.S. Appl. No. 10/617,489, mailed on Oct. 28, 2005.
Office Action from U.S. Appl. No. 10/617,489, mailed on Dec. 5, 2005.
Amendment in Response to Non-Final Office Action from U.S. Appl. No. 10/617,489, filed Mar. 6, 2006.
Non-Final Office Action from U.S. Appl. No. 10/617,489, mailed on Oct. 23, 2006.
Supplemental Amendment from U.S. Appl. No. 10/617,489, filed Nov. 28, 2006.
Terminal Disclaimer from U.S. Appl. No. 10/617,489, filed Nov. 28, 2006.
Notice of Allowance from U.S. Appl. No. 10/617,489, mailed on Jan. 4, 2007.
Petition to Withdraw Application from Issue Pursuant to 37 CFR 1.313(c)(2) and Preliminary Amendment from U.S. Appl. No. 10/617,489, filed Jan. 25, 2008.
Statement of Substance of Interview from U.S. Appl. No. 10/617,489, filed Feb. 26, 2008.
Statement of Substance of Interview from U.S. Appl. No. 10/617,489, filed Mar. 6, 2008.
Notice of Allowance and Examiner Interview Summary from U.S. Appl. No. 10/617,489, mailed on Apr. 4, 2008.
Statement of Substance of Interview from U.S. Appl. No. 10/617,489, filed May 15, 2008.
Notice of Allowance from U.S. Appl. No. 10/617,489, mailed on Oct. 2, 2008.
Petition Decision from U.S. Appl. No. 10/617,489, mailed on Oct. 22, 2008.
Petition Decision from U.S. Appl. No. 10/617,489, mailed on Dec. 15, 2008.
Petition Decision from U.S. Appl. No. 10/617,489, mailed on Dec. 22, 2008.
RCE and Interview Summary from U.S. Appl. No. 10/617,489, filed Jan. 2, 2009.
Application and Preliminary Amendment for U.S. Appl. No. 10/641,780, filed Aug. 15, 2003.
Second Preliminary Amendment for U.S. Appl. No. 10/641,780, filed Jan. 3, 2006.
Restriction Requirement for U.S. Appl. No. 10/641,780, mailed on Jun. 12, 2006.
Response to Restriction Requirement from U.S. Appl. No. 10/641,780, filed Jul. 11, 2006.
Non-Final Office Action, from U.S. Appl. No. 10/641,780, mailed on Oct. 5, 2006.
Amendment in Response to Non-Final Office Action from U.S. Appl. No. 10/641,780, filed Jan. 5, 2007.
Supplemental Amendment, from U.S. Appl. No. 10/641,780, filed Mar. 27, 2007.
Office Communication from U.S. Appl. No. 10/641,780, mailed on Jun. 12, 2007.
Statement of Substance of Interview from U.S. Appl. No. 10/641,780, filed Jun. 29, 2007.
Petition Decision from U.S. Appl. No. 10/641,780, mailed on Dec. 5, 2008.
Declaration of Interference, between U.S. Appl. No. 10/641,780 and U.S. Patent No. 6,838,264, Patent Interference No. 105,575 (MPT), mailed on Aug. 30, 2007.
Cantor Power of Attorney and Designation of Lead and Backup Counsel, filed Sep. 12, 2007.
Cantor Notice of Related Proceedings, filed Sep. 12, 2007.
Cantor Notice of Real Party-in-Interest, filed Sep. 12, 2007.
Cantor Request for File Copies, filed Sep. 12, 2007.
Cantor Clean Copy of Claims, filed Sep. 12, 2007.
Zahradnik Power of Attorney and Designation of Lead Counsel, filed Sep. 13, 2007.
Zahradnik Notice of Related Proceedings, filed Sep. 13, 2007.
Zahradnik Notice of Lead and Backup Counsel, filed Sep. 13, 2007.
Zahradnik Notice of Real Party-in-Interest, filed Sep. 13, 2007.
Zahradnik Request for File Copies, filed Sep. 13, 2007.
Zahradnik Clean Copy of Claims, filed Sep. 13, 2007.
Order Authorizing Copies of Office Records, filed Sep. 18, 2007.
Cantor Annotated Copy of Claims, filed Sep. 26, 2007.
Zahradnik Substitute Clean Copy of Claims, filed Sep. 27, 2007.
Zahradnik Annotated Copy of Claims, filed Sep. 27, 2007.
Notice to the Board Re: Incomplete Copy of Files, filed Oct. 9, 2007.
Cantor List of Intended Motions, filed Oct. 11, 2007.
Zahradnik List of Motions, filed Oct. 11, 2007.
Order Motion Times—Bd.R. 104(c), from Patent Interference No. 105,575 (MPT), filed Oct. 22, 2007.
Joint Stipulation Extending Time Periods 1 and 2, from Patent Interference No. 105,575 (MPT), filed Nov. 19, 2007.
Joint Statement Regarding Settlement Discussions, from Patent Interference No. 105,575 (MPT), filed Nov. 30, 2007.
Cantor Exhibit List and Exhibits, filed Dec. 14, 2007.
Cantor Substantive Motion 1—Motion for Benefit to Priority Applications, filed Dec. 14, 2007.
Cantor Substantive Motion 2—Motion to Change the Count, filed Dec. 14, 2007.
Cantor Substantive Motion 3—Motion to Correct Inventorship, filed Dec. 14, 2007.
Notice of Request to Correct Inventorship, filed Dec. 14, 2007.
Notice of Filing Cantor Priority Statement, filed Dec. 14, 2007.
Notice of Filing of Zahradnik Priority Statement, filed Dec. 14, 2007.
Zahradnik List of Exhibits and Exhibits, filed Dec. 14, 2007.
Zahradnik Substantive Motion 1 (Motion for Judgment Under 35 U.S.C. § 135(b)), filed Dec. 14, 2007.
Zahradnik Substantive Motion 2 (Judgment for No Interference in Fact), filed Dec. 14, 2007.
Zahradnik Substantive Motion 3 (Judgment for Lack of Written Description), filed Dec. 14, 2007.
Zahradnik Substantive Motion 4 (Judgment for Lack of Enablement), filed Dec. 14, 2007.
Cantor Contingent Responsive Motion 1, Contingent Motion to Substitute Claim 47 for Claims in Interference, filed Jan. 18, 2008.
Deposition of J. Stuart Woodhead, Ph.D., taken on Feb. 21, 2008.
Deposition of J. Scott Hutchison, Ph.D., taken on Feb. 15, 2008.
Deposition of Thomas L. Cantor, taken on Feb. 8, 2008.

Cantor Opposition 1 (Opposition to Motion for Judgment Under 35 U.S.C. § 135(b)), Patent Interference No. 105,575 (MPT), filed Mar. 21, 2008.
Cantor Opposition 2 (Opposition to Motion for Judgment of No Interference-in-Fact), Patent Interference No. 105,575 (MPT), filed Mar. 21, 2008.
Cantor Opposition to Zahradnik Motion 3, Judgment for Lack of Written Description, Patent Interference No. 105,575 (MPT), filed Mar. 21, 2008.
Cantor Opposition to Zahradnik Motion 4, Judgment for Lack of Enablement, Patent Interference No. 105,575 (MPT), filed Mar. 21, 2008.
Cantor Exhibit List and Exhibits, Patent Interference No. 105,575 (MPT), filed Mar. 21, 2008.
Supplemental Affidavit of J. Stuart Woodhead, Ph.D., dated Mar. 19, 2008.
Zahradnik Opposition 1 (Opposition to Cantor Substantive Motion 1—Motion for Benefit to Priority Applications), Patent Interference No. 105,575 (MPT), filed Mar. 21, 2008.
Zahradnik Opposition 2 (Opposition to Cantor Substantive Motion 2 to Change the Count), Patent Interference No. 105,575 (MPT), filed Mar. 21, 2008.
Zahradnik Opposition 3 (Opposition to Cantor Contingent Responsive Motion 1—Contingent Motion to Substitute Claim 47 for Claims in Interference), Patent Interference No. 105,575 (MPT), filed Mar. 21, 2008.
Zahradnik List of Exhibits as of Mar. 21, 2008, Patent Interference No. 105,575 (MPT), filed Mar. 21, 2008.
Declaration of J. Scott Hutchison, dated Mar. 20, 2008.
Cantor Reply 1 (In Support of Motion for Benefit to Priority Applications) from Patent Interference No. 105,575 (MPT), filed May 19, 2008.
Cantor Reply 2 (In Support of Motion to Change the Count) from Patent Interference No. 105,575 (MPT), filed May 19, 2008.
Cantor Reply 3 in Response to Zahradnik Opposition 3 (In Support of Cantor Contingent Responsive Motion 1 to Substitute Claim 47 for Claims in Interference) from Patent Interference No. 105,575 (MPT), filed May 19, 2008.
Zahradnik List of Exhibits as of May 19, 2008 from Patent Interference No. 105,575 (MPT), filed May 19, 2008.
Zahradnik Reply 1 (Reply to Cantor Opposition to Zahradnik Motion 1—§ 135(b)) from Patent Interference No. 105,575 (MPT), filed May 19, 2008.
Zahradnik Reply 2 (Reply to Cantor Opposition to Zahradnik Motion 2—No Interference-In-Fact) from Patent Interference No. 105,575 (MPT), filed May 19, 2008.
Zahradnik Reply 3 (Reply to Cantor Opposition to Zahradnik Motion 3—Written Description) from Patent Interference No. 105,575 (MPT), filed May 19, 2008.
Zahradnik Reply 4 (Reply to Cantor Opposition to Zahradnik Motion 4—Enablement) from Patent Interference No. 105,575 (MPT), filed May 19, 2008.
Zahradnik Service of Demonstrative Exhibits, Patent Interference No. 105,575 (MPT), Jul. 16, 2008.
Cantor Service of Demonstrative Exhibits, Patent Interference No. 105,575 (MPT), Jul. 16, 2008.
Order—Bd. R. 104 Regarding Demonstrative Aids, Patent Interference No. 105,575 (MPT), filed Jul. 24, 2008.
Transcript of Oral Hearing Held on Wednesday, Jul. 23, 2008 in Patent Interference 105,575 (MPT) Before the Board of Patent Appeals and Interferences.
Application and Preliminary Amendment for U.S. Appl. No. 10/760,091, filed Jan. 16, 2004.
Restriction Requirement for U.S. Appl. No. 10/760,091, mailed on Jun. 26, 2006.
Response to Restriction Requirement from U.S. Appl. No. 10/760,091, filed Jul. 26, 2006.
Statement of Substance of Interview from U.S. Appl. No. 10/760,091, filed Oct. 17, 2006.
Non-Final Office Action from U.S. Appl. No. 10/760,091, mailed on Oct. 23, 2006.
Amendment in Response to Non-Final Office Action from U.S. Appl. No. 10/760,091, filed Mar. 23, 2007.
Non-Final Office Action from U.S. Appl. No. 10/760,091, mailed on Jun. 15, 2007.
Amendment in Response to Non-Final Office Action from U.S. Appl. No. 10/760,091, filed Sep. 17, 2007.
Final Office Action from U.S. Appl. No. 10/760,091, mailed on Dec. 13, 2007.
Amendment After Final Action Under 37 C.F.R. 1.116 from U.S. Appl. No. 10/760,091, filed Jun. 12, 2008.
Non-Final Office Action from U.S. Appl. No. 10/760,091, mailed on Aug. 19, 2008.
Application and Preliminary Amendment for U.S. Appl. No. 10/945,608 filed Sep. 20, 2004.
Non-Final Office Action from U.S. Appl. No. 10/945,608, mailed on Nov. 15, 2006.
Amendment in Response to Non-Final Office Action from U.S. Appl. No. 10/945,608, filed Feb. 15, 2007.
Final Office Action from U.S. Appl. No. 10/945,608, mailed on May 2, 2007.
Advisory Action from U.S. Appl. No. 10/945,608, mailed on Jul. 23, 2007.
Request for Continued Examination from U.S. Appl. No. 10/945,608, filed Aug. 2, 2007.
Non-Final Office Action from U.S. Appl. No. 10/945,608, mailed on Oct. 16, 2007.
Amendment in Response to Non-Final Office Action from U.S. Appl. No. 10/945,608, filed Apr. 16, 2008.
Notice of Allowance and Examiner's Amendment from U.S. Appl. No. 10/945,608, mailed on Jul. 23, 2008.
Statement of Substance of Interview from U.S. Appl. No. 10/945,608, filed Aug. 7, 2008.
Petition Decision from U.S. Appl. No. 10/945,608, mailed on Sep. 26, 2008.
Petition Decision from U.S. Appl. No. 10/945,608, mailed on Nov. 19, 2008.
Notice of Allowance from U.S. Appl. No. 10/945,608, mailed on Jan. 28, 2009.
Non-Final Office Action from U.S. Appl. No. 11/799,726, mailed on Apr. 28, 2008.
Amendment in Response to Non-Final Office Action from U.S. Appl. No. 11/799,726, filed Sep. 29, 2008.
Final Office Action from U.S. Appl. No. 11/799,726, mailed on Dec. 31, 2008.
Office Action—Examination Report dated Jul. 14, 2003 for EP application No. 00 902 406.8-2404.
Response to Office Action—Examination Report dated Jul. 14, 2003, response dated Jan. 23, 2004.
Office Action—Examination Report dated Mar. 16, 2004, for EP application No. 00 902 406.8-2404.
Response to Office Action—Examination Report dated Mar. 16, 2004, response dated Sep. 8, 2004.
Office Action—Examination Report dated May 6, 2005, for EP application No. 00 902 406.8-2404.
Written Submissions prior to the Oral Proceedings, dated Sep. 15, 2005.
Letter from counsel following phone conference with examiner and in anticipation of Oral Proceedings, dated Oct. 4, 2005.
Result of Consultation of Sep. 29, 2005, dated Oct. 12, 2005.
Result of Consultation of Oct. 4, 2005, dated Oct. 12, 2005.
Minutes of the Oral Proceedings on Oct. 17, 2005, dated Nov. 9, 2005.
Result of Consultation, from EP Application No. 00 902 406.8-2404, dated Dec. 19, 2005.
Communication Under Rule 51(4) EPC, from EP Application No. 00 902 406.8-2404, dated Dec. 19, 2005.
Request for correction After IGRA, from EP Application No. 00 902 406.8-2404, dated Apr. 27, 2006.
Documents for Grant, from EP Application No. 00 902 406.8-2404, dated May 24, 2006.
Brief Communication, from EP Application No. 00 902 406.8-2404, dated Jun. 12, 2006.
Receipt of Third Party Observations, from EP Application No. 00 902 406.8-2404, dated Jul. 6, 2006 (and English Translation).

Communication Pursuant to Article 115(2) EPC, from EP Application No. 00 902 406.8-2404, dated Jul. 18, 2006.
Communication of a Notice of Opposition against EP Patent No. 1 151 307, dated Dec. 3, 2007.
Communication of a Notice of Opposition against EP Patent No. 1 151 307, dated Dec. 3, 2007 (with Briefing Paper—Opposition Proceedings at the EPO English translation).
English Translation of Opposition Documents, Opposition to European Patent No. EP 1 151 307 B1, dated Nov. 19, 2007.
Patentee's Response to Grounds of Opposition, EP Patent No. 1 151 307, dated Jul. 14, 2008.
Affidavit of J. Stuart Woodhead, Ph.D., FRC.Path., dated Dec. 13, 2007.
"Assays for Antibody Production" in Current Protocols in Immunology, (1991) section 2.1.
Official Action (and English Translation) for Japanese Patent Application No. 2000-593958, mailed on Aug. 13, 2004.
Partial Translation of the Response filed Feb. 9, 2005.
Decision of Rejection (and English Translation) for Japanese Patent Application No. 2000-593958, mailed on Aug. 9, 2005.
Appeal Brief from Japanese Application No. 2000-593958 (in Japanese only), filed on Dec. 7, 2005.
Claims Allowed by the Appeal Board from Japanese Application No. 2000-593958, Feb. 8, 2008.
Amendment from Japanese Application No. 2000-593958 (in Japanese only), filed on Mar. 28, 2008.
Decision on Appeal (Notice of Allowance) from Japanese Application No. 2000-593958, mailed on May 2, 2008.
International Preliminary Examination Report for PCT/US00/00855, mailed on Feb. 16, 2001 (WO 00/42437).
Written Opinion for PCT/US04/21896 mailed on Mar. 7, 2005 (WO 05/01843).
PCT Demand and Response to the Written Opinion for PCT/US04/21896, mailed on Jun. 6, 2005 (WO 05/01843).
International Preliminary Report on Patentability for PCT/US04/21896, mailed on Sep. 20, 2005 (WO 05/01843).
Office Action from Canadian Patent Application No. 2,360,020, mailed on Mar. 12, 2007.
Amendment from Canadian Application No. 2,360,020, filed Sep. 12, 2007.
Office Action from Canadian Application No. 2,360,020, dated Sep. 30, 2008.
U.S. Appl. No. 60/224,396, filed Aug. 10, 2002, by Thomas Cantor.
U.S. Appl. No. 09/323,606, filed Jun. 2, 1999 by Thomas Cantor.
U.S. Appl. No. 09/636,530, filed Aug. 10, 2000 by Thomas Cantor.
Restriction Requirement from U.S. Appl. No. 10/799,476, mailed on Jan. 10, 2007.
Response to Restriction Requirement from U.S. Appl. No. 10/799,476, filed Jan. 24, 2007.
Non-Final Office Action from U.S. Appl. No. 10/799,476, mailed on Apr. 17, 2007.
Amendment in Response to Non-Final Office Action from U.S. Appl. No. 10/799,476, filed Aug. 29, 2007.
Final Office Action from U.S. Appl. No. 10/799,476, mailed on Nov. 6, 2007.
Request for Continued Examination and Amendment from U.S. Appl. No. 10/799,476, filed Mar. 6, 2008.
Final Office Action from U.S. Appl. No. 10/799,476, mailed on Apr. 21, 2008.
Restriction Requirement from U.S. Appl. No. 10/265,276, mailed on Aug. 20, 2004.
Response to Restriction Requirement from U.S. Appl. No. 10/265,276, filed Dec. 18, 2004.
Non-Final Office Action from U.S. Appl. No. 10/265,276, mailed on Jan. 24, 2005.
Amendment in Response to Non-Final Office Action from U.S. Appl. No. 10/265,276, filed Apr. 25, 2005.
Non-Final Office Action from U.S. Appl. No. 10/265,276, mailed on Jun. 28, 2005.
Amendment in Response to Non-Final Office Action from U.S. Appl. No. 10/265,276, filed Oct. 7, 2005.
Final Rejection from U.S. Appl. No. 10/265,276, mailed on Jan. 4, 2006.
Amendment After Final Action (37 CFR Section 1.116) from U.S. Appl. No. 10/265,276, filed Apr. 4, 2006.
Advisory Action from U.S. Appl. No. 10/265,276, mailed on May 18, 2006.
Pre-Appeal Brief Request for Review from U.S. Appl. No. 10/265,276, filed Jun. 13, 2006.
Notice of Panel Decision from Pre-Appeal Brief Review from U.S. Appl. No. 10/265,276, mailed on Aug. 4, 2006.
Non-Final Office Action from U.S. Appl. No. 10/265,276, mailed on Oct. 20, 2006.
Amendment in Response to Non-Final Office Action from U.S. Appl. No. 10/265,276, filed Jan. 19, 2007.
Final Rejection from U.S. Appl. No. 10/265,276, mailed on Apr. 19, 2007.
Notice of Appeal and Reasons for Requesting Pre-Appeal Brief Review from U.S. Appl. No. 10/265,276, filed Oct. 10, 2007.
Notice of Decision from Pre-Appeal Brief Review from U.S. Appl. No. 10/265,276, mailed on Nov. 30, 2007.
Restriction Requirement from U.S. Appl. No. 10/674,294, mailed on Jun. 2, 2006.
Response to Restriction Requirement from U.S. Appl. No. 10/674,294, filed Jun. 28, 2006.
Non-Final Office Action from U.S. Appl. No. 10/674,294, mailed on Sep. 11, 2006.
Amendment in Response to Non-Final Office Action from U.S. Appl. No. 10/674,294, filed Dec. 13, 2006.
Final Rejection from U.S. Appl. No. 10/674,294, mailed on Feb. 15, 2007.
Amendment After Final Action Under 37 CFR 1.116 from U.S. Appl. No. 10/674,294, filed Apr. 13, 2007.
Advisory Action from U.S. Appl. No. 10/674,294, mailed on Apr. 27, 2007.
Examiner Interview Summary from U.S. Appl. No. 10/674,294, mailed on May 17, 2007.
Amendment After Final Action Under 37 CFR 1.116 from U.S. Appl. No. 10/674,294, filed May 18, 2007.
Substance of Examiner Interview from U.S. Appl. No. 10/674,294, filed Jun. 14, 2007.
Non-Final Office Action from U.S. Appl. No. 10/674,294, mailed on Jun. 18, 2007.
Amendment in Response to Non-Final Office Action from U.S. Appl. No. 10/674,294, filed Sep. 17, 2007.
Non-Final Office Action from U.S. Appl. No. 10/674,294, mailed on Nov. 29, 2007.
Amendment in Response to Non-Final Office Action from U.S. Appl. No. 10/674,294, filed Apr. 29, 2008.
Notice of Allowance from U.S. Appl. No. 10/674,294, mailed on Aug. 7, 2008.
Notice of Allowance from U.S. Appl. No. 10/956,760, mailed on Aug. 14, 2008.
Restriction Requirement from U.S. Appl. No. 10/958,541, mailed on Mar. 7, 2007.
Response to Restriction Requirement from U.S. Appl. No. 10/958,541, filed Apr. 4, 2007.
Non-Final Office Action from U.S. Appl. No. 10/958,541, mailed on Aug. 3, 2007.
Restriction Requirement from U.S. Appl. No. 11/516,912, mailed on Jul. 31, 2007.
Response to Restriction Requirement from U.S. Appl. No. 11/516,912, filed Sep. 19, 2007.
Non-Final Office Action from U.S. Appl. No. 11/516,912, mailed on Nov. 13, 2007.
Amendment in Response to Non-Final Office Action from U.S. Appl. No. 11/516,912, filed May 13, 2008.
Final Office Action from U.S. Appl. No. 11/516,912, mailed on Sep. 4, 2008.
Amendment After Final Action Under 37 C.F.R. 1.116 from U.S. Appl. No. 11/516,912, filed Oct. 21, 2008.
Advisory Action from U.S. Appl. No. 11/516,912, mailed on Nov. 10, 2008.
Preliminary Amendment, from U.S. Appl. No. 09/730,174, filed Jan. 9, 2002.

Restriction Requirement, from U.S. Appl. No. 09/730,174, mailed on Jul. 2, 2002.
Response to Restriction Requirement, from U.S. Appl. No. 09/730,174, filed Jul. 19, 2002.
Non-Final Office Action, from U.S. Appl. No. 09/730,174, mailed on Oct. 1, 2002.
Amendment, from U.S. Appl. No. 09/730,174, filed Dec. 19, 2002.
Final Office Action, from U.S. Appl. No. 09/730,174, mailed on Mar. 24, 2003.
Amendment After Final Rejection, from U.S. Appl. No. 09/730,174, filed Jun. 23, 2003.
Advisory Action, from U.S. Appl. No. 09/730,174, mailed on Jul. 15, 2003.
Amendment & Response to Advisory Action, from U.S. Appl. No. 09/730,174, filed Aug. 14, 2003.
Non-Final Office Action, from U.S. Appl. No. 09/730,174, mailed on Jun. 15, 2004.
Amendment & Response to Advisory Action, from U.S. Appl. No. 09/730,174, filed Jun. 30, 2004.
Notice of Allowance, from U.S. Appl. No. 09/730,174, mailed on Sep. 21, 2004.
Restriction Requirement, from U.S. Appl. No. 10/954,695, mailed on Sep. 21, 2005.
Non-Final Office Action, from U.S. Appl. No. 10/954,695, mailed on Dec. 7, 2005.
Amendment, from U.S. Appl. No. 10/954,695, filed May 30, 2006.
Final Office Action, from U.S. Appl. No. 10/954,695, mailed on Aug. 24, 2006.
RCE and Preliminary Amendment, from U.S. Appl. No. 10/954,695, filed Oct. 26, 2006.
Non-Final Office Action, from U.S. Appl. No. 10/954,695, mailed on Jan. 3, 2007.
Response to Office Action, from U.S. Appl. No. 10/954,695, filed Mar. 12, 2007.
Supplemental Response to Office Action, from U.S. Appl. No. 10/954,695, filed Apr. 18, 2007.
Final Office Action, from U.S. Appl. No. 10/954,695, mailed on Jul. 27, 2007.
Request for Continued Examination, from U.S. Appl. No. 10/954,695, filed Jan. 4, 2008.
Non-Final Office Action, from U.S. Appl. No. 10/954,695, mailed on Feb. 28, 2008.
Response to Office Action from U.S. Appl. No. 10/954,695, filed May 5, 2008.
Non-Final Office Action, from U.S. Appl. No. 10/998,927, mailed on Dec. 21, 2006.
Response to Office Action, from U.S. Appl. No. 10/998,927, filed Jan. 2, 2007.
Notice of Allowance, from U.S. Appl. No. 10/998,927, mailed on Apr. 3, 2007.
Non-Final Office Action, from U.S. Appl. No. 09/898,398, mailed on Nov. 12, 2003.
Amendment in Response to Nov. 12, 2003 Office Action, from U.S. Appl. No. 09/898,398, filed Feb. 12, 2004.
Final Office Action, from U.S. Appl. No. 09/898,398, mailed on Apr. 28, 2004.
Amendment in Response to Apr. 28, 2004 Office Action, from U.S. Appl. No. 09/898,398, filed Jun. 28, 2004.
Notice of Allowance, from U.S. Appl. No. 09/898,398, mailed on Jul. 19, 2004.
Non-Final Office Action, from U.S. Appl. No. 10/921,368, mailed on Dec. 13, 2004.
Non-Final Office Action, from U.S. Appl. No. 11/146,598, mailed on Dec. 19, 2005.
Non-Final Office Action from U.S. Appl. No. 11/437,428, mailed on Oct. 16, 2006.
Amendment and Reply Under 37 CFR 1.111. from U.S. Appl. No. 11/437,428, filed Mar. 16, 2007.
Non-Final Office Action from U.S. Appl. No. 11/437,428, mailed on Jun. 6, 2007.
Amendment and Reply Under 37 CFR 1.111 from U.S. Appl. No. 11/437,428, filed Nov. 6, 2007.
Final Office Action, from U.S. Appl. No. 11/437,428, mailed on Jan. 25, 2008.
Submission Accompanying a Request for Continued Examination Under 37 CFR 1.114 from U.S. Appl. No. 11/437,428, filed Apr. 25, 2008.
Non-Final Office Action from U.S. Appl. No. 11/437,428, mailed on Jun. 11, 2008.
Amendment and Reply Under 37 CFR 1.111 from U.S. Appl. No. 11/437,428, filed Nov. 12, 2008.
Preliminary Amendment, from U.S. Appl. No. 10/168,185, filed Mar. 21, 2003.
Restriction Requirement, from U.S. Appl. No. 10/168,185, mailed on Jan. 26, 2006.
Response to Restriction Requirement, from U.S. Appl. No. 10/168,185, filed Jul. 26, 2006.
Non-Final Office Action, from U.S. Appl. No. 10/168,185, mailed on Oct. 23, 2006.
Examiner Interview Summary, from U.S. Appl. No. 10/168,185, mailed on Feb. 27, 2007.
Amendment in Response to Non-Final Office Action, from U.S. Appl. No. 10/168,185, filed Apr. 23, 2007.
Final Office Action, from U.S. Appl. No. 10/168,185, mailed on Jul. 25, 2007.
Amendment After Final Action Under 37 C.F.R. 1.116, from U.S. Appl. No. 10/168,185, filed Jan. 25, 2008.
Advisory Action, from U.S. Appl. No. 10/168,185, mailed on Apr. 1, 2008.
Amendment Accompanying a Request for Continued Examination from U.S. Appl. No. 10/168,185, filed Aug. 22, 2008.
Non-Final Office Action from U.S. Appl. No. 10/168,185, mailed on Nov. 17, 2008.
Complaint for Patent Infringement, *Nichols Institute Diagnostics, Inc.* v. *Scantibodies Clinical Laboratory, Inc. and Scantibodies Laboratory, Inc.*, filed Jan. 8, 2002 in the United States District Court for the Southern District of California, Case No. 02 CV 0046 B (LAB).
Answer and Counterclaims of Defendants Scantibodies Clinical Laboratory, Inc. and Scantibodies Laboratory, Inc., filed May 9, 2002.
Notice of Motion and Motion for Summary Judgment Pursuant to 35 U.S.C. § 102(f) for Nonjoinder of Co-Inventor, filed on May 16, 2002.
Scantibodies Clinical Laboratory, Inc. and Scantibodies Laboratory, Inc.'s Memorandum of Points and Authorities in Support of Motion for Summary Judgment Pursuant to 35 U.S.C. § 102(f) for NonJoinder of Co-Inventor, filed May 16, 2002.
Declaration of M. Andrew Woodmansee in Support of Scantibodies Clinical Laboratory, Inc. and Scantibodies Laboratory Inc.'s Motion for Summary Judgment Pursuant to 35 U.S.C. § 102(f) for NonJoinder of Co-Inventor, filed May 16, 2002.
Plaintiff/Counterdefendant Nichols Institute Diagnostics, Inc.'s Reply to Defendants' Counterclaims, filed May 29, 2002.
Defendant Scantibodies Clinical Laboratory's Initial Disclosure, filed Jul. 16, 2002 in 02 CV 0046 B (LAB).
Nichols Institute Diagnostics, Inc.'s Initial Disclosures Pursuant to Fed. R. Civ. P. 26(a)(1), filed on Jul. 16, 2002 in 02 CV 0046 B (LAB).
Plaintiff's Memorandum of Points and Authorities in Support of Opposition to Defendants' Motion for Summary Judgment Pursuant to 35 U.S.C. § 102(f) fo NonJoinder of Co-Inventor, filed Jul. 22, 2002.
Declaration of Vicki G. Norton in Support of Plaintiffs Opposition to Motion for Summary Judgment Pursuant to 35 U.S.C. § 102(f) for NonJoinder of Co-Inventor, filed Jul. 22, 2002.
Declaration of James T. Carmichael in Support of Plaintiffs Opposition to Motion for Summary Judgment Pursuant to 35 U.S.C. § 102(f) for NonJoinder of Co-Inventor, filed Jul. 22, 2002.
Scantibodies Clinical Laboratory, Inc. and Scantibodies Laboratory, Inc.'s Reply in Support of Motion for Summary Judgment Pursuant to 35 U.S.C. § 102(f) for NonJoinder of Co-Inventor, filed Jul. 29, 2002.
Declaration of David C. Doyle in Support of Scantibodies Clinical Laboratory, Inc. and Scantibodies Laboratory Inc.'s Reply in Support of Motion for Summary Judgment Pursuant to 35 U.S.C. § 102(f) for NonJoinder of Co-Inventor, filed Jul. 29, 2002.
Plaintiff's Sur-Reply in Opposition to Defendants' Reply to Plaintiff's Opposition to Motion for Summary Judgment Pursuant to 35 U.S.C. § 102(f) for NonJoinder of Co-Inventor, filed Aug. 16, 2002.
Declaration of Vicki G. Norton in Support of Plaintiffs Sur-Reply in Opposition to Defendants' Reply to Opposition to Motion for Summary Judgment Pursuant to 35 U.S.C. § 102(f) for NonJoinder of Co-Inventor, filed Aug. 16, 2002.
Scantibodies Clinical Laboratory, Inc. and Scantibodies Laboratory, Inc.'s Response to Plaintiff's Sur-Reply, filed Aug. 20, 2002.
Declaration of David C. Doyle in Support of Scantibodies Clinical Laboratory, Inc. and Scantibodies Laboratory Inc.'s Response to Plaintiffs Sur-Reply, filed Aug. 20, 2002.
Order Denying as Moot Defendants' Motion for Summary Judgment Pursuant to 35 U.S.C. § 102(f) for NonJoinder of Co-Inventor, Denying Request for Stay, and Ordering Plaintiff to File Amended Complaint, issued Sep. 6, 2002.
Amended Complaint for Patent Infringement, Case No. 02-CV-0046 B (LAB), filed Sep. 20, 2002.
Scantibodies Clinical Laboratory, Inc. and Scantibodies Laboratory, Inc.'s Notice of Appeal, filed Oct. 4, 2002.
Notice of Document Discrepancies rejecting the original Answer and Counterclaims filed by Scantibodies on May 9, 2002, notice dated Oct. 15, 2002.
Answer and Counterclaims of Defendants Scantibodies Clinical Laboratory, Inc. and Scantibodies Laboratory Inc. to Nichols' Amended Complaint for Patent Infringement, filed Oct. 17, 2002.
Plaintiff/Counterdefendant Nichols Institute Diagnostics, Inc.'s Reply to Defendants' Counterclaims, filed Nov. 4, 2002.
Plaintiffs' Brief on Claim Construction for the '790 Patent, filed Nov. 12, 2002.
Declaration of Vicki G. Norton in Support of Plaintiffs' Brief on Claim Construction for the '790 Patent, filed Nov. 12, 2002.
Scantibodies Clinical Laboratory, Inc. and Scantibodies Laboratory, Inc.'s Claim Construction Brief for U.S. Patent No. 6,030,790, filed Nov. 12, 2002.
Declaration of M. Andrew Woodmansee in Support of Scantibodies Clinical Laboratory, Inc. and Scantibodies Laboratory Inc.'s Claim Construction Brief for U.S. Patent No. 6,030,790, filed Nov. 12, 2002.
Declaration of Dr. Richard A. Lerner in Support of Scantibodies Clinical Laboratory, Inc. and Scantibodies Laboratory Inc.'s Claim Construction Brief for U.S. Patent No. 6,030,790, filed Nov. 12, 2002.
Declaration of Thomas G. Wiseman in Support of Scantibodies Clinical Laboratory, Inc. and Scantibodies Laboratory Inc.'s Claim Construction Brief for U.S. Patent No. 6,030,790, filed Nov. 12, 2002.
Nichols Institute Diagnostics, Inc.'s Supplemental Brief in Support of Motion for Judgment on the Pleadings, filed Dec. 2, 2002.
Reply of Scantibodies Clinical Laboratory, Inc. and Scantibodies Laboratory, Inc. in Support of Motion for Reconsideration of Dismissal for Want of Jurisdiction, filed Dec. 3, 2002.
Notice of Document Discrepancies, filed Dec. 5, 2002.
Report and Recommendation, filed Dec. 31, 2002 in United States District Court for the Southern District of Florida, Miami Division.
ESRD's Verified Motion to Tax Costs as Prevailing Party, filed Jan. 3, 2003 in United States District Court for the Southern District of Florida, Miami Division.
Plaintiff's Supplemental Brief on Claim Construction for the '790 Patent, filed Jan. 8, 2003.
Declaration of Vicki G. Norton in Support of Plaintiffs Supplemental Brief on Claim Construction for the '790 Patent, filed Jan. 8, 2003.
Declaration of Joseph O. Falkinham III, Ph.D. in Support of Plaintiffs' Supplemental Brief on Claim Construction for the '790 Patent, filed Jan. 8, 2003.
[Proposed] Order Granting Nichols Institute Diagnostics Inc.'s Ex Parte Application for Order Allowing Exhibit 9 to Plaintiffs Supplemental Brief on Claim Construction for the '790 Patent to be Filed Under Seal, filed Jan. 8, 2003.
Scantibodies Clinical Laboratory, Inc. and Scantibodies Laboratory Inc.'s Supplemental Brief in Advance of Claim Construction Hearing on U.S. Patent No. 6,030,790, filed Jan. 8, 2003.
Declaration of M. Andrew Woodmansee in Support of Scantibodies Clinical Laboratory, Inc. and Scantibodies Laboratory, Inc.'s Supplemental Claim Construction Brief for U.S. Patent No. 6,030,790, filed Jan. 8, 2003.
Parties Joint Claim Construction Chart, filed Jan. 8, 2003.
Notice of Document Discrepancies, filed Jan. 10, 2003.
Scantibodies Clinical Laboratory Inc. and Scantibodies Laboratory Inc.'s Brief in Advance of Jan. 30, 2003 Hearing on the Terms "Suitable Carrier" and "Peptide" for U.S. Patent No. 6,030,790, filed Jan. 22, 2003.
Declaration of M. Andrew Woodmansee in Support of Scantibodies Clinical Laboratory, Inc. and Scantibodies Laboratory, Inc.'s Brief in Advance of Jan. 30, 2003 Hearing on the Terms "Suitable Carrier" and "Peptide" for the U.S. Patent No. 6,030,790, filed Jan. 22, 2003.
Plaintiff Nichols Institute Diagnostics, Inc.'s Second Supplemental Claim Construction Brief, filed Jan. 22, 2003.
Declaration of Vicki G. Norton in Support of Plaintiffs Second Supplemental Brief on Claim Construction for the '790 Patent, filed Jan. 22, 2003.
Declaration of Dr. Leonard J. Deftos in Support of Plaintiff Nichols Institute Diagnostics, Inc.'s Second Supplemental Claim Construction Brief, filed Jan. 22, 2003.
Notice of Motion and Motion for Summary Judgment Pursuant to 35 U.S.C. § 102(b), filed Feb. 25, 2003.
Memorandum of Points and Authorities in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Statement of Undisputed Material Facts in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of Richard A. Lerner, M.D., in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of J. Stuart Woodhead, Ph.D., in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of Andrew William Smith in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of Kimberly L. Briggs in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Declaration of Hans H. Linden in Support of Motion for Summary Judgment Pursuant to 35 U.S.C. § 102(b) by Defendants Scantibodies Clinical Laboratory, Inc. and Scantibodies Laboratory, Inc., filed Feb. 25, 2003.
Order Construing Patent Claims and Terms for Jury Trial, filed Mar. 10, 2003.
Scantibodies Clinical Laboratory, Inc. and Scantibodies Laboratory, Inc.'s Notice of Motion and Motion for Reconsideration of Court's Mar. 10, 2003 Order Construing Patent Claims and Terms for Jury Trial, filed Mar. 24, 2003.
Scantibodies Clinical Laboratory, Inc. and Scantibodies Laboratory, Inc.'s Motion for Reconsideration of Court's Mar. 10, 2003 Order Construing Patent Claims and Terms for Jury Trial, filed Mar. 24, 2003.
Declaration of M. Andrew Woodmansee in Support of Scantibodies Clinical Laboratory, Inc. and Scantibodies Laboratory, Inc.'s Motion for Reconsideration of Court's Mar. 10, 2003 Order Construing Patent Claims and Terms for Jury Trial, filed Mar. 24, 2003.
Re-Notice of Motion and Motion for Summary Judgment Pursuant to 35 U.S.C. § 102(b), or in the Alternative, 35 U.S.C. § 103(a), filed Apr. 2, 2003.
Scantibodies Clinical Laboratory, Inc. and Scantibodies Laboratory, Inc.'s Supplemental Memorandum of Points and Authorities in Support of Motion for Summary Judgment Pursuant to 35 U.S.C. § 102(b), or in the Alternative, 35 U.S.C. § 102(a), filed Apr. 2, 2003.

Nichols Institute Diagnostics, Inc. Opposition to Defendants' Motion for Reconsideration of the Court's Mar. 10, 2003 Order Construing Patent Claims and Terms for Jury Trial, filed Apr. 8, 2003.
Declaration of Julia A. Miller in Support of Nichols Institute Diagnostics, Inc. Opposition to Defendants' Motion for Reconsideration of the Court's Mar. 10, 2003 Order Construing Patent Claims and for Jury Trial, filed Apr. 8, 2003.
Declaration of Dr. Leonard J. Deftos in Support of Nichols Institute Diagnostics, Inc. Opposition to Defendants' Motion for Reconsideration of Court's Mar. 10, 2003 Order Construing Patent Claims and Terms for Jury Trial, filed Apr. 8, 2003.
Scantibodies Clinical Laboratory, Inc. and Scantibodies Laboratory, Inc.'s Reply to Opposition to Motion for Reconsideration of Court's Mar. 10, 2003 Order Construing Patent Claims and Terms for Jury Trial, filed Apr. 14, 2003.
Order Granting Motion for Reconsideration and Confirming Original Order Construing Patent Claims Filed Mar. 10, 2003, filed Apr. 29, 2003.
Nichols Institute Diagnostics, Inc.'s Opposition to Motion for Summary Judgment Pursuant to 35 U.S.C. § 102(b) or in the Alternative 35 U.S.C. § 103(a) by Defendants Scantibodies Clinical Laboratory, Inc. and Scantibodies Laboratory, Inc., filed May 7, 2003.
Declaration of Julia A. Miller in Support of Nichols Institute Diagnostics, Inc.'s Opposition to Motion for Summary Judgment Pursuant to 35 U.S.C. § 102(b) or in the Alternative 35 U.S.C. § 103(a) by Defendants Scantibodies Clinical Laboratory, Inc. and Scantibodies Laboratory, Inc, filed May 7, 2003.
Declaration of Leonard J. Deftos in Support of Nichols Institute Diagnostics' Opposition to Motion for Summary Judgment Pursuant to 35 U.S.C. § 102(b), or in the Alternative, 35 U.S.C. § 103(a), filed May 7, 2003.
Declaration of Douglas E. Olson in Support of Nichols' Application Under Federal Rule of Civil Procedure 56(f), filed May 7, 2003.
Declaration of Peter R. Munson in Support of Nichols Institute Diagnostics, Inc.'s Opposition to Motion for Summary Judgment Pursuant to 35 U.S.C. § 102(b) or in the Alternative 35 U.S.C. § 103(a) by Defendants Scantibodies Clinical Laboratory, Inc. and Scantibodies Laboratory, Inc., filed May 8, 2003.
Nichols Institute Diagnostics, Inc.'s Response to Defendants' Statement of Undisputed Material Facts in Support of Motion for Summary Judgment Pursuant to 35 U.S.C. § 102(b) or Alternatively Under 35 U.S.C. § 103(a), filed May 8, 2003.
Nichols Institute Diagnostics, Inc.'s Notice of Motion and Motion to Strike the Briggs, Linden, and Smith Declarations Submitted by Defendants in Support of Motion for Summary Judgment, filed May 8, 2003.
Nichols Institute Diagnostics, Inc.'s Memorandum in Support of Motion to Strike the Briggs, Linden, and Smith Declarations Submitted by Defendants in Support of Motion for Summary Judgment, filed May 8, 2003.
Scantibodies Clinical Laboratory, Inc. and Scantibodies Laboratory, Inc.'s Reply in Support of Motion for Summary Judgment Pursuant to 35 U.S.C. § 102(b), or in the Alternative, 35 U.S.C. § 102(a), filed May 14, 2003.
Reply Declaration of M. Andrew Woodmansee in Support of Motion for Summary Judgment Pursuant to 35 U.S.C. § 102(b), or in the Alternative 35 U.S.C. § 103(a), filed May 14, 2003.
Declaration of Paul Ayris in Support of Motion for Summary Judgment Pursuant to 35 U.S.C. § 102(b) by Defendants Scantibodies Clinical Laboratory, Inc. and Scantibodies Laboratory, Inc., filed May 14, 2003.
Declaration of Marianne Kranenborg in Support of Motion for Summary Judgment Pursuant to 35 U.S.C. § 102(b) by Defendants Scantibodies Clinical Laboratory, Inc. and Scantibodies Laboratory, Inc., filed May 14, 2003.
Declaration of Roderick Morrison in Support of Motion for Summary Judgment Pursuant to 35 U.S.C. § 102(b) by Defendants Scantibodies Clinical Laboratory, Inc. and Scantibodies Laboratory Inc, filed May 14, 2003.
Scantibodies Clinical Laboratory, Inc. and Scantibodies Laboratory, Inc.'s Opposition to Nichols' Motion to Strike Affidavits of Briggs, Linden, and Smith, filed May 14, 2003.
Scantibodies Clinical Laboratory, Inc's and Scantibodies Laboratory, Inc.'s Evidentiary Objections to Declaration of Julia Miller, filed May 14, 2003.
Nichols Institute Diagnostics, Inc.'s Notice of Motion and Motion to Strike the Kranenborg Declaration Submitted by Defendants in Support of Reply to Nichols' Opposition to Motion for Summary Judgment, filed May 16, 2003.
Nichols Institute Diagnostics, Inc.'s Memorandum in Support of Motion to Strike the Kranenborg Declaration Submitted by Defendants in Support of their Reply to Nichols' Opposition to Motion for Summary Judgment, filed May 16, 2003.
Nichols Institute Diagnostics, Inc.'s Errata Sheet Regarding Responses to Scantibodies' Undisputed Fact Nos. 6 and 41, filed May 20, 2003.
Scantibodies Clinical Laboratory, Inc. and Scantibodies Laboratory Inc.'s Objections to Nichols Institute Diagnostics, Inc's Errata Sheet Regarding Responses to Scantibodies' Undisputed Fact Nos. 6 and 41, filed May 21, 2003.
Order Denying Defendants' Motion for Summary Judgment and Granting Summary Adjudication, filed Jun. 2, 2003.
Scantibodies' Notice of Motion and Motion for Judgment on the Pleadings for Lack of Standing and Failure to Join an Indispensable Party or, in the Alternative, to Join a Necessary Party Pursuant to FRCP 19, filed Jul. 16, 2003.
Memorandum of Points and Authorities in Support of Scantibodies' Motion for Judgment on the Pleadings for Lack of Standing and Failure to Join an Indispensable Party or, in the Alternative, to Join a Necessary Party Pursuant to FRCP 19, filed Jul. 16, 2003.
Nichols Institute Diagnostics, Inc.'s Opposition to Scantibodies' Motion for Judgment on the Pleadings for Lack of Standing and Failure to Join an Indispensable Party or, in the Alternative, to Join a Necessary Party Pursuant to FRCP 19, filed Sep. 18, 2003.
Declaration of K. Ramakrishnan, filed Sep. 18, 2003.
Declaration of Randall Ringold, filed Sep. 18, 2003.
Declaration of Dr. Michael Harder, filed Sep. 18, 2003.
Reply in Support of Scantibodies' Motion for Judgment on the Pleadings for Lack of Standing and Failure to Join an Indispensable Party or, in the Alternative, to Join a Necessary Party Pursuant to FRCP 19, filed Sep. 24, 2003.
Declaration of Thomas Cantor in Support of Scantibodies' Motion for Judgment on the Pleadings for Lack of Standing and Failure to Join an Indispensable Party or, in the Alternative, to Join a Necessary Party Pursuant to FRCP 19, filed Sep. 24, 2003.
Nichols Institute Diagnostics, Inc.'s Notice of Motion and Motion to Permit Service of its Supplemental Amended Complaint Under F.R.C.P. 15(d), filed Nov. 24, 2003.
Memorandum of Points and Authorities in Support of Nichols Institute Diagnostics, Inc.'s Motion to Permit Service of its Supplemental Amended Complaint Under F.R.C.P. 15(d), filed Nov. 24, 2003.
Order Granting Defendants' Motion on the Pleadings and Dismissing Case with Leave to Amend, filed Dec. 1, 2003.
Nichols Institute Diagnostics, Inc.'s Notice of Motion and Motion for Leave to File Amended Complaint, filed Jan. 26, 2004.
Nichols Institute Diagnostics, Inc.'s Memorandum of Points and Authorities in Support of its Motion for Leave to File Amended Complaint, filed Jan. 26, 2004.
Nichols Institute Diagnostics, Inc's Notice of Application and Ex Parte Application for Order Sealing Exhibit 2 to its Second Amended Complaint, Exhibit A to the Declaration of Julia A. Miller in Support of Nichols Institute Diagnostics, Inc.'s Motion for Leave to File Amended Complaint, filed Jan. 26, 2004.
Declaration of Julia A. Miller in Support of Nichols' Ex Parte Application for Order Sealing Exhibit 2 to its Second Amended Complaint, Exhibit A to the Declaration of Julia A. Miller in Support of Nichols Institute Diagnostics, Inc.'s Motion for Leave to File Amended Complaint, filed Jan. 26, 2004.
Scantibodies' Notice of Motion and Motion for Judgment on the Pleadings for Lack of Standing and for Attorneys' Fees, filed Jan. 26, 2004.
Memorandum of Points and Authorities in Support of Scantibodies' Motion for Judgment on the Pleadings for Lack of Standing and for Attorneys' Fees, filed Jan. 26, 2004.

Scantibodies Laboratory, Inc., and Scantibodies Clinical Laboratory, Inc.'s Opposition to Nichols Institute Diagnostics, Inc.'s Motion to Amend Complaint, filed Feb. 9, 2004.
Nichols Institute Diagnostics, Inc.'s Reply to Scantibodies Laboratory, Inc. and Scantibodies Clinical Laboratory, Inc.'s Opposition to Motion for Leave to File Amended Complaint, filed Feb. 23, 2004.
Declaration of Julia A. Miller in Support of Nichols Institute Diagnostics, Inc.'s Reply to Scantibodies Laboratory, Inc. and Scantibodies Clinical Laboratory, Inc's Opposition to Motion for Leave to File Amended Complaint, filed Feb. 23, 2004.
Scantibodies' Reply to Nichols Institute Diagnostics, Inc.'s Opposition to Motion for Judgment on the Pleadings for Lack of Standing and for Attorneys' Fees, filed Feb. 23, 2004.
Order Granting Plaintiff's Motion for Leave to File a Supplemental Amended Complaint, filed Mar. 8, 2004.
Order Denying Defendant's Motion for Judgment on the Pleadings and Denying Defendant's Motion for Attorneys' Fees, filed Mar. 8, 2004.
Answer and Counterclaims of Defendants Scantibodies Clinical Laboratory, Inc. and Scantibodies Laboratory, Inc. to Nichols' Second Amended Complaint for Patent Infringement, filed Apr. 6, 2004.
Plaintiff/Counter-defendant Nichols Institute Diagnostics, Inc.'s Reply to Defendants' Counterclaim, filed Apr. 26, 2004.
Scantibodies' Notice of Motion and Motion for Summary Judgment of Invalidity and Noninfringement, filed Feb. 18, 2005.
Declaration of Randolph Wall, PHD in Support of Scantibodies' Memorandum of Points and Authorities in Support of Motion for Summary Judgment of Invalidity and Noninfringement, filed Feb. 18, 2005.
Declaration of Dr. Wolf Grosskopf in Support of Motion for Summary Judgment of Invalidity and Noninfringement, filed Feb. 18, 2005.
[Proposed] Order Granting Scantibodies' Motion for Summary Judgment of Invalidity and Noninfringement, filed Feb. 18, 2005.
Notice of Motion and Motion for Nichols Institute Diagnostics, Inc.'s Motion for Summary Judgment That the '790 Patent Claims are Valid and Infringed, filed Feb. 28, 2005.
Memorandum of Points and Authorities in Support of Nichols Institute Diagnostics, Inc.'s Motion for Summary Judgment that the '790 Patent Claims are Valid and Infringed, filed Feb. 28, 2005.
Declaration of John E. Peterson in Support of Nichols Institute Diagnostics, Inc.'s Motion for Summary Judgment that the '790 Patent Claims are Valid and Infringed, filed Feb. 28, 2005.
Declaration of Shelby J. Hall, Ph.D., in Support of Nichols Institute Diagnostics, Inc.'s Motion for Summary Judgment that the '790 Patent Claims are Valid and Infringed, filed Feb. 28, 2005.
Declaration of Joseph O. Falkinham III, Ph.D., in Support of Nichols Institute Diagnostics, Inc.'s Motion for Summary Judgment that the '790 Patent Claims are Valid and Infringed, filed Feb. 28, 2005.
Nichols Institute Diagnostics, Inc.'s Notice of and Ex Parte Application for Order to File Documents Under Seal with Motion for Summary Judgment, filed Feb. 28, 2005.
Declaration of April M. Alex in Support of Nichols' Ex Parte Application for Order to File Documents Under Seal with Motion for Summary Judgment, filed Feb. 28, 2005.
Declaration of K. Ramakrishan, Ph.D. in Support of Nichols Institute Diagnostics, Inc.'s Opposition to Motion for Summary Judgment of Invalidity and Non-Infringement, filed Mar. 7, 2005.
Declaration of Eva Guthrie in Support of Nichols Institute Diagnostics, Inc.'s Opposition to Motion for Summary Judgment of Invalidity and Non-Infringement, filed Mar. 7, 2005.
Declaration of John E. Peterson in Support of Nichols Institute Diagnostics, Inc.'s Opposition to Motion for Summary Judgment of Invalidity and Non-Infringement, filed Mar. 7, 2005.
Reply Memorandum of Points and Authorities in Support of Scantibodies' Motion for Summary Judgment of Invalidity and Noninfringement, filed Mar. 14, 2005.
Notice of Decisions on Plaintiff's and Defendants' Cross Motions for Summary Judgment Regarding United States Patent No. 6,030,790 and Defendants' Motion to Stay the Trial and Defendants' Motion to Sequence Evidence of Liability and Damages at Trial, filed Mar. 30, 2005.

Scantibodies' Notice of Motion and Motion for Reconsideration of Order Denying Motion to Stay, or in the Alternative, Motion for Certification Under 28 U.S.C. § 1292(b), filed Apr. 1, 2005.
Memorandum of Points and Authorities in Support of Scantibodies' Motion for Reconsideration of Order Denying Motion to Stay, or in the Alternative, Motion for Certification Under 28 U.S.C. § 1292(b), filed Apr. 1, 2005.
Declaration of M. Andrew Woodmansee in Support of Scantibodies' Motion for Reconsideration of Order Denying Motion to Stay, or in the Alternative, Motion for Certification Under 28 U.S.C. § 1292(b), filed Apr. 1, 2005.
Expert Report of Michael R. Hamrell, Ph.D.
Defendants Scantibodies Clinical Laboratory, Inc., and Scantibodies Laboratory, Inc.'s Rebuttal Expert Witness Report by Steven Jones.
Rebuttal Expert Report of Richard A. Lerner, M.D.
Initial Expert Report of Randolph Wall, Ph.D.
Rebuttal Expert Report of Randolph Wall, Ph.D.
Expert Report of Thomas G. Wiseman, Esq.
Supplemental Expert Report of Thomas G. Wiseman, Esq.
Rebuttal Expert Report of Thomas G. Wiseman, Esq.
Expert Report of J. Stuart Woodhead Ph.D., FRCPath.
Supplemental Report of J. Stuart Woodhead Ph.D., FRCPath.
Rebuttal Expert Report of Claude Arnaud, M.D., FACE.
Rebuttal Expert Report of Gerald Bjorge.
Expert Report of Larry W. Evans Pursuant to Rule 26(A)(2)(B), Fed. R. Civ. P.
Expert Report of L.J. Deftos, MD, JD, LLM.
Order Denying Defendants' Motion for Summary Judgment of Invalidity of United States Patent No. 6,030,790 and Granting Summary Adjudication That the Patent is Not Anticipated or Rendered Obvious by Certain Prior Art References, filed May 3, 2005.
Order Denying Defendants' Motion for Summary Judgment of Noninfringement and Denying Plaintiff's Motion for Summary Judgment of Infringement of United States Patent No. 6,030,790, filed May 3, 2005.
Subpoena in a Civil Case for Dr. Claude Arnaud, filed May 4, 2005.
Subpoena in a Civil Case for Dr. Ellen Vitetta, filed May 4, 2005.
Subpoena in a Civil Case for Joseph O. Falkinham, III, filed May 4, 2005.
Subpoena in a Civil Case for Gerald Bjorge, filed May 4, 2005.
Subpoena in a Civil Case for Larry W. Evans, filed May 4, 2005.
Subpoena in a Civil Case for Dr. Wolf-Georg Forsmann, filed May 4, 2005.
Subpoena in a Civil Case for Dr. Knut Adermann, filed May 4, 2005.
Subpoena in a Civil Case for Dr. Dieter Hock, filed May 4, 2005.
Subpoena in a Civil Case for Dr. Markus Magerlein, filed May 4, 2005.
Subpoena in a Civil Case for Dr. Thomas Godemeyer, filed May 4, 2005.
Subpoena in a Civil Case for Dr. Michael Harder, filed May 4, 2005.
Subpoena in a Civil Case for Dr. Randy Ringold, filed May 4, 2005.
Subpoena in a Civil Case for Dr. K. Ramakrishan, filed May 4, 2005.
Subpoena in a Civil Case for Eva Guthrie, filed May 4, 2005.
Subpoena in a Civil Case for Julie Lu, filed May 4, 2005.
Nichols' Opposition to Scantibodies' Motion in Limine No. 1 (That Seeks to Exclude Dr. Hall's Experiments), filed May 5, 2005.
Nichols Institute Diagnostics, Inc.'s Opposition to Scantibodies' Motion in Limine No. 2, Nichols' Opposition to Scantibodies Motion in Limine to Exclude Expert Opinion and Other Evidence Regarding Opinion of Counsel, filed May 5, 2005.
Nichols Institute Diagnostics, Inc.'s Opposition to Scantibodies' Motion in Limine No. 3 to Preclude Nichols' Reliance on Doctrine of Equivalents, filed May 5, 2005.
Declaration of Jane Babin in Support of Nichols Institute Diagnostics, Inc.'s Opposition to Scantibodies' in Limine Motion No. 3, filed May 5, 2005.
Nichols Institute Diagnostics, Inc.'s Opposition to Scantibodies' in Limine Motion No. 5, Opposition to Scantibodies' Motion to Preclude Evidence of a Hypothetical Negotiation Between Scantibodies and Nichols, filed May 5, 2005.
Declaration of April Alex in Support of Nichols Institute Diagnostics, Inc.'s Opposition to Scantibodies' in Limine Motion No. 5, filed May 5, 2005.

Nichols Institute Diagnostics, Inc.'s Opposition to Scantibodies' Motion in Limine No. 7 to Exclude Evidence Regarding Medicare Billing, filed May 5, 2005.
Order Granting Nichols Institute Diagnostics Inc.'s Ex Parte Application to Accept Nichols' in Limine Motion No. 21 as Timely Filed, filed May 5, 2005.
Scantibodies' Opposition to Nichols' Motion in Limine No. 1, filed May 5, 2005.
Scantibodies' Opposition to Nichols' Motion in Limine No. 2, filed May 5, 2005.
Scantibodies' Opposition to Nichols' Motion in Limine No. 3, filed May 5, 2005.
Scantibodies' Opposition to Nichols' Motion in Limine No. 4, filed May 5, 2005.
Scantibodies' Opposition to Nichols' Motion in Limine No. 5, filed May 5, 2005.
Scantibodies' Opposition to Nichols' Motion in Limine No. 6, filed May 5, 2005.
Scantibodies' Opposition to Nichols' Motion in Limine No. 7, filed May 5, 2005.
Scantibodies' Opposition to Nichols' Motion in Limine No. 8, filed May 5, 2005.
Scantibodies' Opposition to Nichols' Motion in Limine No. 10, filed May 5, 2005.
Scantibodies' Opposition to Nichols' Motion in Limine No. 11, filed May 5, 2005.
Scantibodies' Opposition to Nichols' Motion in Limine No. 13, filed May 5, 2005.
Scantibodies' Opposition to Nichols' Motion in Limine No. 14, filed May 5, 2005.
Scantibodies' Opposition to Nichols' Motion in Limine No. 15, filed May 5, 2005.
Scantibodies' Opposition to Nichols' Motion in Limine No. 16, filed May 5, 2005.
Scantibodies' Opposition to Nichols' Motion in Limine No. 17, filed May 5, 2005.
Scantibodies' Opposition to Nichols' Motion in Limine No. 18, filed May 5, 2005.
Scantibodies' Opposition to Nichols' Motion in Limine No. 19, filed May 5, 2005.
Scantibodies' Opposition to Nichols' Motion in Limine No. 20, filed May 5, 2005.
Stipulation and Notice of Withdrawal Regarding Four Motions in Limine, filed May 5, 2005.
Supplemental Subpoena in a Civil Case for Ping Gao, filed May 6, 2005.
Supplemental Subpoena in a Civil Case for Scantibodies Laboratory, Inc., filed May 6, 2005.
Supplemental Subpoena in a Civil Case for Scantibodies Clinical Laboratory, Inc., filed May 6, 2005.
Scantibodies' Ex Parte Application Requesting Correction of Order Denying Defendants' Motion for Summary Judgment of Invalidity, filed May 9, 2005.
Declaration of Katherine L. Parker in Support of Scantibodies' Ex Parte Application Requesting Correction of Order Denying Defendants' Motion for Summary Judgment of Invalidity, filed May 9, 2005.
[Proposed] Order Granting Scantibodies' Ex Parte Application Requesting Correction of Order Denying Defendants' Motion for Summary Judgment of Invalidity, filed May 9, 2005.
Transcript of Motion in Limine Hearing/Pretrial Conference, May 9, 2005.
Transcript of Motions in Limine Hearing, May 10, 2005.
Transcript of Motions in Limine Hearing, May 11, 2005.
Scantibodies Clinical Laboratory, Inc., and Scantibodies Laboratory, Inc.'s Second Supplemental Exhibit List, filed May 11, 2005.
Objections to Nichols' Subpoena in a Civil Case and Request for Production of Documents to Vivian Shen, filed May 11, 2005.
Objections to Nichols' Subpoena in a Civil Case and Request for Production of Documents to Stephen Scheibel, filed May 11, 2005.
Objections to Nichols' Subpoena in a Civil Case and Request for Production of Documents to Dr. Richard Lerner, filed May 11, 2005.
Objections to Nichols' Subpoena in a Civil Case and Request for Production of Documents to Randolph Wall, Ph.D., filed May 11, 2005.
Objections to Nichols' Subpoena in a Civil Case and Request for Production of Documents to Mark Gray, filed May 11, 2005.
Objections to Nichols' Subpoena in a Civil Case and Request for Production of Documents to Allen Garrett, filed May 11, 2005.
Objections to Nichols' Subpoena in a Civil Case and Request for Production of Documents to Steven Jones, filed May 11, 2005.
Objections to Nichols' Subpoena in a Civil Case and Request for Production of Documents to Zan Yang, filed May 11, 2005.
Objections to Nichols' Subpoena in a Civil Case and Request for Production of Documents to Thomas G. Wiseman, filed May 11, 2005.
Objections to Nichols' Subpoena in a Civil Case and Request for Production of Documents to Damon Cook, filed May 11, 2005.
Objections to Nichols' Subpoena in a Civil Case and Request for Production of Documents to Frank Hall, filed May 11, 2005.
Objections to Nichols' Subpoena in a Civil Case and Request for Production of Documents to Janet Sharp, filed May 11, 2005.
Objections to Nichols' Subpoena in a Civil Case and Request for Production of Documents to Michael Nordstrom, filed May 11, 2005.
Objections to Nichols' Subpoena in a Civil Case and Request for Production of Documents to Thomas Cantor, filed May 11, 2005.
Objections to Nichols' Subpoena in a Civil Case and Request for Production of Documents to Dr. J. Stuart Woodhead, filed May 11, 2005.
Objections to Nichols' Subpoena in a Civil Case and Request for Production of Documents to Ping Gao, filed May 11, 2005.
Objections to Nichols' Subpoena in a Civil Case and Request for Production of Documents to Scantibodies Laboratory, Inc., filed May 11, 2005.
Objections to Nichols' Subpoena in a Civil Case and Request for Production of Documents to Scantibodies Clinical Laboratory, Inc., filed May 11, 2005.
Objections to Nichols' Supplemental Subpoena in a Civil Case and Request for Production of Documents to Ping Gao, filed May 11, 2005.
Objections to Nichols' Supplemental Subpoena in a Civil Case and Request for Production of Documents to Scantibodies Laboratory Inc., filed May 11, 2005.
Objections to Nichols' Supplemental Subpoena in a Civil Case and Request for Production of Documents to Scantibodies Clinical Laboratory Inc., filed May 11, 2005.
Stipulation and [Proposed] Order RE Early Access to Courtroom 2 and Set Up of Audio Visual Equipment, filed May 11, 2005.
Scantibodies' Proposed Voir Dire Questions, filed May 12, 2005.
Nichols Proposed Voir Dire Questions, filed May 12, 2005.
Transcript of Status Conference, May 12, 2005.
Scantibodies' Supplemental Briefing in Support of Scantibodies' Motion in Limine No. 5 RE Timing and Parties to Hypothetical Negotiation, filed May 13, 2005.
Plaintiff's Memorandum Concerning Freedom of Contract and Retroactivity (In Connection with Defendant's Motion in Limine #5), filed May 13, 2005.
Nichols' Amended Exhibit List to Memorandum of Fact and Law, filed May 13, 2005.
Scantibodies' Trial Brief on Inequitable Conduct, filed May 13, 2005.
Response to Trial Subpoena Request for Production for Claude Arnaud, M.D., filed May 16, 2005.
Response to Trial Subpoena Request for Production for Larry W. Evans, filed May 16, 2005.
Response to Trial Subpoena Request for Production for Gerald H. Bjorge, filed May 16, 2005.
Response to Trial Subpoena Request for Production for Ellen S. Vitetta, filed May 16, 2005.
Response to Trial Subpoena Request for Production for Joseph O. Falkinham, filed May 16, 2005.
Scantibodies Clinical Laboratory, Inc., and Scantibodies Laboratory, Inc.'s Third Supplemental Exhibit List, filed May 16, 2005.
Notice of Deposition of Allan Garret, filed May 16, 2005.
Notice of Deposition of Stephen Jones, filed May 16, 2005.

Notice of Document Discrepancies, Supplemental Exhibit List, filed by Scantibodies, May 17, 2005.
Notice of Document Discrepancies, Supplemental Briefing, filed by Scantibodies, May 17, 2005.
Scantibodies' Objections to Nichols' Amended Exhibit List, filed May 17, 2005.
Bench Trial Transcript—vol. I, May 16, 2005.
Bench Trial Transcript—vol. II, May 17, 2005.
Bench Trial Transcript—vol. III, May 18, 2005.
Bench Trial Transcript—vol. IV, May 19, 2005.
Bench Trial Transcript—vol. V, May 23, 2005.
Bench Trial Transcript—vol. VI, May 24, 2005.
Bench Trial Transcript—vol. VII, May 25, 2005.
Bench Trial Transcript—vol. VIII, May 27, 2005.
Order on Motion in Limine Nichols No. 3, filed May 19, 2005.
Nichols' Objections to Scantibodies' Amended Exhibit Lists, filed May 20, 2005.
[Proposed] Jury Instructions of Plaintiff Nichols, filed May 25, 2005.
Nichols Institute Diagnostics, Inc.'s [Proposed] Verdict Form Regarding Infringement and Validity, filed May 25, 2005.
Nichols Institute Diagnostics, Inc.'s [Proposed] Verdict Form Regarding Damages and Willfulness, filed May 25, 2005.
Scantibodies' Notice of Motion and Motion for Judgment on Inequitable Conduct and Invalidity, filed May 25, 2005.
Scantibodies' Memorandum of Points and Authorities in Support of Motion for Judgment on Inequitable Conduct and Invalidity, filed May 25, 2005.
Declaration of Katherine L. Parker in Support of Scantibodies' Motion for Judgment on Inequitable Conduct and Invalidity, filed May 25, 2005.
Scantibodies' Proposed Jury Instructions, filed May 25, 2005.
Scantibodies' Proposed Jury Instructions on Damages and Willfulness, filed May 25, 2005.
Scantibodies' Proposed Special Verdict Form, filed May 25, 2005.
Scantibodies' Proposed Special Verdict Form on Damages and Willfulness, filed May 25, 2005.
Notice of Document Discrepancies, Supplemental Exhibit List filed by Scantibodies, May 26, 2005.
Scantibodies' Brief Regarding Materiality of Rejection by Foreign Patent Office, filed May 26, 2005.
Scantibodies' Bench Memorandum Requesting Corrective Jury Instruction, filed May 26, 2005.
Nichols' Second Amended Exhibit List to Memorandum of Fact and Law, filed May 27, 2005.
Jury Trial Transcript—Day 1, May 25, 2005.
Jury Trial Transcript—Day 2, May 26, 2005.
Jury Trial Transcript—Day 3, May 31, 2005.
Jury Trial Transcript—Day 4, Jun. 1, 2005.
Jury Trial Transcript—Day 5, Jun. 2, 2005.
Jury Trial Transcript—Day 6, Jun. 6, 2005.
Jury Trial Transcript—Day 7, Jun. 7, 2005.
Jury Trial Transcript—Day 8, Jun. 8, 2005.
Jury Trial Transcript—Day 9, Jun. 9, 2005.
Jury Trial Transcript—Day 10, Jun. 13, 2005.
Jury Trial Transcript—Day 11, Jun. 14, 2005.
Jury Trial Transcript—Day 12, Jun. 15, 2005.
Jury Trial Transcript—Day 13, Jun. 16, 2005.
Jury Trial Transcript—Day 14, Jun. 20, 2005.
Jury Trial Transcript—Day 15, Jun. 21, 2005.
Jury Trial Transcript—Day 16, Jun. 22, 2005.
Jury Trial Transcript—Day 17, Jun. 23, 2005.
Jury Trial Transcript—Day 18, Jun. 27, 2005.
Scantibodies' Proposed Supplemental Jury Instruction Regarding "Idea" of a Patent, filed Jun. 2, 2005.
Notice of Document Discrepancies, Second Amended Exhibit List, filed by Nichols Institute, Jun. 3, 2005.
Nichols' Third Amended Exhibit List to Memorandum of Fact and Law, filed Jun. 5, 2005.
Nichols Institute Diagnostics, Inc.'s Notice of and Ex Parte Application for Order to File Third Amended Exhibit List to Memorandum of Fact and Law, filed Jun. 6, 2005.
Declaration of April M. Alex in Support of Nichols' Ex Parte Application for Order to File Third Amended Exhibit List to Memorandum of Fact and Law, filed Jun. 6, 2005.
[Proposed] Order Granting Nichols Institute Diagnostics, Inc.'s Ex Parte Application to File Its Third Amended Exhibit List to Memorandum of Fact and Law, filed Jun. 6, 2005.
Scantibodies Clinical Laboratory, Inc. and Scantibodies Laboratory, Inc.'s Fourth Supplemental Exhibit List, filed Jun. 6, 2005.
Scantibodies' Second Proposed Supplemental Jury Instruction (Regarding Inventorship), filed Jun. 8, 2005.
Scantibodies' Amended Proposed Special Verdict Form, filed Jun. 8, 2005.
Nichols Institute Diagnostics, Inc.'s Notice of and Ex Parte Application for Order to File Its [Proposed] Second Supplemental Jury Instructions of Plaintiff Nichols, filed Jun. 9, 2005.
Declaration of Joshua G. Gigger in Support of Nichols' Ex Parte Application for Order to File [Proposed] Second Supplemental Jury Instructions of Plaintiff Nichols, filed Jun. 9, 2005.
[Proposed] Second Supplemental Jury Instructions of Plaintiff Nichols, filed Jun. 9, 2005.
[Proposed] Order Granting Nichols Institute Diagnostics, Inc.'s Ex Parte Application to File [Proposed] Second Supplemental Jury Instructions of Plaintiff Nichols, filed Jun. 9, 2005.
Deposition of Knut Adermann, Exhibit No. 11.
Deposition of James T. Carmichael, Exhibit No. 15.
Deposition of Roger T. Frost, Exhibit No. 18.
Deposition of Allen Garrett, Exhibit 20.
Deposition of Allen Garrett vol. 2, Exhibit No. 21.
Deposition of Michael Harder, Exhibit No. 23.
Deposition of Dieter Hock, Exhibit No. 24.
Deposition of Hartmut H. Malluche, No. 27.
Deposition of Vivian Shen, Exhibit No. 34.
Deposition of Ellen S. Vitetta, Exhibit No. 35.
Judgment Following Court and Jury Trial, Filed Jun. 29, 2005.
Notice of Motion and Motion for Nichols Institute Diagnostics, Inc.'s Renewed Motion for Judgment as a Matter of Law, filed Jul. 13, 2005.
Memorandum of Points and Authorities in Support of Nichols Institute Diagnostics, Inc.'s Renewed Motion for Judgment as a Matter of Law, filed Jul. 13, 2005.
Declaration of April M. Alex in Support of Nichols Institute Diagnostics, Inc.'s Renewed Motion for Judgment as a Matter of Law, filed Jul. 13, 2005.
[Proposed] Order Granting Nichols Institute Diagnostics, Inc.'s Renewed Motion for Judgment as a Matter of Law, filed Jul. 13, 2005.
Memorandum of Points and Authorities in Support of Nichols Institute Diagnostics, Inc.'s Motion for a New Trial, filed Jul. 13, 2005.
Declaration of Charles B. Cohler in Support of Nichols Institute Diagnostics, Inc.'s Motion for a New Trial, filed Jul. 13, 2005.
Declaration of Julia A. Miller in Support of Nichols Institute Diagnostics, Inc.'s Motion for a New Trial, filed Jul. 13, 2005.
Scantibodies' Notice of Motion and (1) Motion for Relief From Judgment of Infringement as to Claims 17 and 21 and (2) Renewed Motion for Judgment as a Matter of Law, filed Jul. 14, 2005.
Scantibodies' Memorandum of Points and Authorities in Support of (1) Motion for Relief From Judgment of Infringement as to Claims 17 and 21 and (2) Renewed Motion for Judgment as a Matter of Law, filed Jul. 14, 2005.
Declaration of M. Andrew Woodmansee in Support of (1) Motion for Relief From Judgment of Infringement as to Claims 17 and 21 and (2) Renewed Motion for Judgment as a Matter of Law, filed Jul. 14, 2005.
Declaration of M. Andrew Woodmansee in Support of Scantibodies' Application to Tax Costs, filed Jul. 14, 2005.
Scantibodies' Consolidated Opposition to Nichols' Motion for Judgment as a Matter of Law and Nichols' Motion for New Trial, filed Aug. 1, 2005.
Declaration of M. Andrew Woodmansee in Support of Scantibodies' Consolidated Opposition to Nichols' Motion for Judgment As a Matter of Law and Nichols' Motion for New Trial, filed Aug. 1, 2005.
Nichols Institute Diagnostics, Inc.'s Opposition to Scantibodies' (1) Motion for Relief From Judgment of Infringement as to Claims 17 and 21 and (2) Motion for Judgment as a Matter of Law, filed Aug. 1, 2005.

Declaration of April M. Alex in Support of Nichols Institute Diagnostics, Inc.'s Opposition to Scantibodies' (1) Motion for Relief From Judgment of Infringement as to Claims 17 and 21 and (2) Motion for Judgment as a Matter of Law, filed Aug. 1, 2005.
[Proposed] Order Denying Scantibodies' Motion for Judgment as a Matter of Law, filed Aug. 1, 2005.
Opposition of Nichols Institute Diagnostics, Inc. To Application to Tax Costs, filed Aug. 1, 2005.
Scantibodies' Reply Brief in Support of (1) Motion for Relief From Judgment of Infringement as to Claims 17 and 21 and (2) Renewed Motion for Judgment as a Matter of Law, filed Aug. 8, 2005.
Declaration of M. Andrew Woodmansee in Support of Scantibodies' Reply Brief in Support of (1) Motion for Relief From Judgment of Infringement as to Claims 17 and 21 and (2) Renewed Motion for Judgment as a Matter of Law, filed Aug. 8, 2005.
Nichols Institute Diagnostics, Inc.'s Reply to Scantibodies' Opposition to Nichols Renewed Motion for Judgment as a Matter of Law, filed Aug. 8, 2005.
Declaration of April M. Alex in Support of Nichols Institute Diagnostics, Inc.'s Reply to Scantibodies' Opposition to Nichols Renewed Motion for Judgment as a Matter of Law, filed Aug. 8, 2005.
Reply to Scantibodies' Opposition to Nichols Motion for a New Trial, filed Aug. 8, 2005.
Declaration of Katherine L. Parker in Support of Scantibodies' Opposition to Nichols' Motion to Retax Costs, filed Aug. 23, 2005.
Reply Memorandum in Support of Nichols Institute Diagnostics, Inc.'s Motion to Retax Costs, filed Aug. 29, 2005.
Order Re: Post-Verdict Motions, filed Aug. 30, 2005.
Declaration of John E. Peterson in Support of Nichols Institute Diagnostics. Inc.'s Motion for Permanent Injunction, filed Sep. 22, 2005.
Settled Findings of Fact and Conclusions of Law on Inequitable Conduct and Order Adjudicating Patent Enforceable, filed Oct. 14, 2005.
Scantibodies' Memorandum of Points and Authorities in Support of Opposition to Nichols' Motion for Permanent Injunction, filed Oct. 14, 2005.
Declaration of Katherine L. Parker in Support of Scantibodies' Opposition to Nichols' Motion for Permanent Injunction, filed Oct. 14, 2005.
Declaration of Allen Garrett in Support of Scantibodies' Opposition to Nichols' Motion for Permanent Injunction, filed Oct. 14, 2005.
Declaration of Dr. Hartmut Malluche in Support of Scantibodies' Opposition to Nichols' Motion for Permanent Injunction, filed Oct. 14, 2005.
Declaration of Dr. Richard Amerling in Support of Scantibodies' Opposition to Nichols' Motion for Permanent Injunction, filed Oct. 14, 2005.
Declaration of Dr. James Tumlin in Support of Scantibodies' Opposition to Nichols' Motion for Permanent Injunction, filed Oct. 14, 2005.
Declaration of Dr. Hassan Fehmi in Support of Scantibodies' Opposition to Nichols' Motion for Permanent Injunction, filed Oct. 14, 2005.
Declaration of Dr. Clarence Wheeler in Support of Scantibodies' Opposition to Nichols' Motion for Permanent Injunction, filed Oct. 14, 2005.
Nichols Institute Diagnostics, Inc.'s Reply Motion for a Permanent Injunction, filed Oct. 24, 2005.
Declaration of Dr. Delbert A. Fisher in Support of Nichols Institute Diagnostics, Inc.'s Reply Motion for a Permanent Injunction, filed Oct. 24, 2005.
Declaration of Dr. Claude Arnaud in Support of Nichols Institute Diagnostics, Inc.'s Reply Motion for a Permanent Injunction, filed Oct. 24, 2005.
Declaration of Katherine L. Parker in Support of Opposition to Nichols' Motion for Clarification of the Court's Order Dated Aug. 30, 2005 Regarding Motion in Limine No. 5, filed Oct. 24, 2005.
Nichols Institute Diagnostics, Inc.'s Objections to and Ex Parte Application to Strike Statements Filed in Support of Scantibodies' Opposition to Nichols' Motion for a Permanent Injunction, filed Oct. 25, 2005.
Scantibodies' Opposition to Nichols' Objections to and Ex Parte Application to Strike Statements Filed in Support of Scantibodies' Opposition to Nichols' Motion for a Permanent Injunction, filed Oct. 27, 2005.
Scantibodies' Emergency Motion to Stay Injunction and Damages/Willfulness Trial Pending Appeal, filed Nov. 17, 2005.
Appellant's Appendix to Scantibodies' Emergency Motion to Stay Injunction and Trial Pending Appeal, filed Nov. 17, 2005.
Federal Circuit Appeal Information Sheet, filed Nov. 17, 2005.
Petition for Writ of Mandamus, filed Nov. 23, 2005.
Nichols Institute Diagnostics, Inc.'s Proposed Single Paragraph Informing Jury of Posture of the Case, filed Nov. 29, 2005.
[Proposed] Jury Instructions of Plaintiff Nichols Institute Diagnostics, Inc., filed Nov. 29, 2005.
Scantibodies' Proposed Jury Instructions for Dec. 5, 2005 Damages and Willfulness Trial, filed Nov. 29, 2005.
Declaration of April M. Alex in Support of Plaintiff's Statement of Position on Scantibodies' Claims of Privilege, as the Result of the Court's Statements About Knorr-Bremse at the Hearing of Nov. 7, 2005, filed Nov. 30, 2005.
Nichols' Response to Scantibodies' Emergency Motion to Stay Injunction Pending Appeal, field Dec. 1, 2005.
Appendix to Nichols' Response to Scantibodies' Emergency Motion to Stay Injunction Pending Appeal, field Dec. 1, 2005.
Nichols' Seventh Amended Exhibit List to Memorandum of Fact and Law, filed Dec. 4, 2005.
Nichols' Eighth Amended Exhibit List to Memorandum of Fact and Law, filed Dec. 4, 2005.
Scantibodies' Reply in Support of Its Emergency Motion to Stay Injunction Pending Appeal, filed Dec. 5, 2005.
Scantibodies Clinical Laboratory, Inc. and Scantibodies Laboratory, Inc.'s Witness List & Sixth Supplemental Exhibit List for Damages/Willfulness Trial, filed Dec. 5, 2005.
Nichols' Ninth Amended Exhibit List to Memorandum of Fact and Law, filed Dec. 6, 2005.
Plaintiff Nichols Institute Diagnostics, Inc.'s First Proposed Supplemental Jury Instructions to the Court's Instructions for the Damages Phase of the Trial, filed Dec. 13, 2005.
Order Granting Nichols' Motion for Entry of Permanent Injunction and Staying Injunction Pending Appeal, filed Nov. 16, 2005.
Transcript of Trial Before the Honorable Rudi M. Brewster, vol. VIII Dec. 16, 2005.
Deposition of Knut Adermann, taken on Jun. 26, 2003.
Deposition of James T. Carmichael, taken on Jun. 26, 2003.
Deposition of Roger T. Frost, taken on Jun. 25, 2003.
Deposition of Allen Garrett, taken on Nov. 6, 2002.
Deposition of Allen Garrett (30(b)(6)), taken on Sep. 19, 2003.
Deposition of Frank Hall, M.D., taken on Sep. 9, 2003.
Deposition of Michael R. Hamrell, taken on Jan. 26, 2005.
Deposition of Michael Harder, taken Jun. 27, 2003.
Deposition of Dieter Hock, Ph.D., taken on Nov. 18, 2002.
Deposition of Hartmut Malluche, M.D., taken on Sep. 26, 2003.
Deposition of Vivian Shen, taken on Jun. 25, 2003.
Deposition of Ellen Vitetta, taken on Jan. 20, 2005.
Deposition of Thomas Wiseman, taken on Jan. 25, 2005.
Scantibodies' Motion to Dismiss Nichols' Cross-Appeal, filed Jan. 10, 2006.
Appellant's Appendix to Scantibodies' Motion to Dismiss Nichols' Cross-Appeal, filed Jan. 10, 2006.
Final Judgment and Stay of Enforcement, filed Jan. 19, 2006.
Declaration of Katherine L. Parker in Support of Scantibodies' Supplemental Brief in Support of Emergency Motion to Stay Injunction Pending Appeal, filed Jan. 19, 2006.
Nichols' Response to Scantibodies' Motion to Dismiss Nichols' Cross-Appeal, filed Jan. 23, 2006.
Plaintiff-Cross Appellant's Appendix to Nichols' Response to Scantibodies' Motion to Dismiss Nichols' Cross-Appeal, filed Jan. 23, 2006.
Scantibodies' Reply in Support of Motion to Dismiss Nichols' Cross-Appeal, filed Jan. 25, 2006.
Declaration of John E. Peterson in Support of Nichols Institute Diagnostics, Inc.'s Motion for Judgment as a Matter of Law on Damages, filed Jan. 27, 2006.

Notice of Motion and Motion for Nichols Institute Diagnostics, Inc.'s Motion for Judgment as a Matter of Law on Damages, filed Jan. 27, 2006.

Memorandum of Points and Authorities in Support of Nichols Institute Diagnostics, Inc.'s Motion for Judgment as a Matter of Law on Damages, filed Jan. 27, 2006.

Nichols Institute Diagnostics, Inc.'s Notice of Motion and Motion for Judgment as a Matter of Law Re: Willfulness and in the Alternative for a New Trial, filed Jan. 27, 2006.

Nichols Institute Diagnostics, Inc.'s Motion for Judgment as a Matter of Law Re: Willfulness and in the Alternative for a New Trial, filed Jan. 27, 2006.

Declaration of April M. Alex in Support of Nichols Institute Diagnostics, Inc.'s Motion for Judgment as a Matter of Law Re: Willfulness and in the Alternative for a New Trial, filed Jan. 27, 2006.

Nichols Institute Diagnostics, Inc.'s Notice of Motion and Motion for Enhancement of Damages, filed Jan. 27, 2006.

Nichols Institute Diagnostics, Inc.'s Memorandum of Points and Authorities in Support of Motion for Enhancement of Damages, filed Jan. 27, 2006.

Declaration of April M. Alex in Support of Motion for Enhancement of Damages, filed Jan. 27, 2006.

Order Granting Stay Pending Appeal and Dismissing Nichols' Cross-Appeal, filed Feb. 1, 2006.

Declaration of April M. Alex in Support of Nichols Institute Diagnostics, Inc.'s Application for Award of Attorney's Fees and Expenses, filed Feb. 2, 2006.

Notice of Motion and Motion in Support of Nichols Institute Diagnostics, Inc.'s Memorandum of Points and Authorities in Support of Application for Award of Attorneys' Fees and Expenses, filed Feb. 2, 2006.

Nichols Institute Diagnostics, Inc.'s Memorandum of Points and Authorities in Support of Application for Award of Attorneys' Fees, filed Feb. 2, 2006.

Declaration of April M. Alex in Support of Nichols Institute Diagnostics, Inc.'s Memorandum in Support of Application to Tax Costs, filed Feb. 2, 2006.

Scantibodies' Memorandum of Points and Authorities in Support of Opposition to Nichols' Motion for Prejudgment Interest, filed Feb. 17, 2006.

Consolidated Declaration of Katherine L. Parker in Support of Scantibodies' Oppositions to Nichols' Motions Re 1) Willfulness; 2)Enhanced Damages; and 3) Attorneys' Fees, filed Feb. 17, 2006.

Scantibodies' Memorandum of Points and Authorities in Support of Opposition to Nichols' Motion for Judgment as a Matter of Law Re: Willfulness and in the Alternative for a New Trial, filed Feb. 17, 2006.

Scantibodies' Memorandum of Points and Authorities in Support of Opposition to Nichols' Motion for Application for Award of Attorneys' Fees and Expenses, filed Feb. 17, 2006.

Nichols Institute Diagnostics, Inc.'s Reply in Support of its Application for Award of Attorneys' Fees and Expenses, filed Feb. 27, 2006.

Nichols Institute Diagnostics, Inc.'s Reply Memorandum of Points and Authorities in Support of Motion for Enhancement of Damages, filed Feb. 27, 2006.

Nichols Institute Diagnostics, Inc.'s Reply Motion for Prejudgment Interest, filed Feb. 27, 2006.

Nichols Institute Diagnostics, Inc.'s Reply Motion for Judgment as a Matter of Law Re: Willfulness and in the Alternative for a New Trial, filed Feb. 27, 2006.

Court Docket from PACER for *Nichols Institute Diagnostics, Inc.* v. *Scantibodies Clinical Laboratory, Inc.*, from the US District Court for the Southern District of California, docket accessed May 25, 2006.

Court Docket from PACER for *Nichols Institute Diagnostics, Inc.* v. *Scantibodies Clinical Laboratory, Inc.*, from the US District Court for the Southern District of California, docket accessed Sep. 8, 2006 (for 2006 dates only).

Court Docket from PACER for *Nichols Institute Diagnostics, Inc.* v. *Scantibodies Clinical Laboratory, Inc.*, from the US District Court for the Southern District of California, accessed May 23, 2007.

Appellants Scantibodies' Opening Brief, filed Jan. 30, 2006.

Appellee Nichols' Brief, filed Mar. 27, 2006.

Appellants Scantibodies' Reply Brief, filed Apr. 21, 2006.

Court Docket from PACER for *Nichols Institute Diagnostics, Inc.* v. *Scantibodies Clinical Laboratory, Inc.*, from the US Court of Appeals for the Federal Circuit, docket accessed May 25, 2006.

Transcription of the Aug. 9, 2006 Oral Argument, US Court of Appeals for the Federal Circuit, Case No. 06-1087.

Appellant Nichols Institute of Diagnostics, Inc.'s Opening Brief, US Court of Appeals for the Federal Circuit, Case No. 06-1443, filed Aug. 22, 2006.

Appellant Nichols Institute of Diagnostics, Inc.'s Corrected Opening Brief, US Court of Appeals for the Federal Circuit, Case No. 06-1443, filed Aug. 30, 2006.

Court Docket from PACER for *Nichols Institute Diagnostics, Inc.* v. *Scantibodies Clinical Laboratory, Inc.*, from the US Court of Appeals for the Federal Circuit, Case No. 06-1087, docket accessed Sep. 8, 2006.

Court Docket from PACER for *Nichols Institute Diagnostics, Inc.* v. *Scantibodies Clinical Laboratory, Inc.*, from the US Court of Appeals for the Federal Circuit, Case No. 06-1443, docket accessed Sep. 8, 2006.

Decision from the US Court of Appeals for the Federal Circuit, Case No. 06-1087, *Nichols Institute Diagnostics, Inc.*, v. *Scantibodies Clinical Laboratory, Inc., and Scantibodies Laboratory, Inc.*, Decided Sep. 20, 2006.

Order Granting Stay, filed Oct. 12, 2006, US Court of Appeals for the Federal Circuit, Case No. 2006-1443.

Order Denying Petition for Panel Rehearing and Petition for Rehearing En Banc, United States Court of Appeals for the Federal Circuit, *Nichols Institute Diagnostics, Inc.* v. *Scantibodies Clinical Laboratory, Inc., and Scantibodies Laboratory, Inc.*, Case No. 06-1087, order issued on Nov. 20, 2006.

Court Docket from PACER for *Nichols Institute Diagnostics, Inc.* v. *Scantibodies Clinical Laboratory, Inc.*, from the US Court of Appeals for the Federal Circuit, Case No. 06-1087, docket accessed May 23, 2007.

Court Docket from PACER for *Nichols Institute Diagnostics, Inc.* v. *Scantibodies Clinical Laboratory, Inc.*, from the US Court of Appeals for the Federal Circuit, Case No. 06-1443, docket accessed May 23, 2007.

Request for Reexamination Under 37 C.F.R. § 1.510 for US Patent No. 6,030,790, filed Feb. 4, 2005.

Ex Parte Reexamination Communication Transmittal Form for US Patent No. 6,030,790, and Order Granting Reexamination, mailed Mar. 30, 2005.

Certificate of Correction pertaining to inventorship for U.S. Patent No. 6,030,790, dated Aug. 6, 2002.

Certificate of Correction pertaining to text for U.S. Patent No. 6,030,790, dated Aug. 27, 2002.

Office Action in Ex Parte Reexamination of U.S. Patent 6,030,790, Control No. 90/007,412, mailed on Sep. 28, 2005.

First Amendment and Response to Reexamination Office Action, filed Nov. 28, 2005.

Information Disclosure Statement for Rexamination No. 90/007,412, filed Nov. 28, 2005.

Miscellaneous Communication for Reexam Control No. 90/007,412, filed Mar. 1, 2006.

Supplemental Amendment to Reexam Control No. 90/007,412, filed Mar. 7, 2006.

Miscellaneous Communication for Reexam Control No. 90/007,412, filed Mar. 9, 2006.

Response to Notice of Defective Paper in Ex Parte Reexamination, mailed on Mar. 14, 2006, in the Reexamination of U.S. Patent No. 6,030,790, Control No. 90/007,412.

EX Parte Reexamination Interview Summary dated Apr. 20, 2006, in the Reexamination of U.S. Patent No. 6,030,790, Control No. 90/007,412.

Statement of Substance of Interview Under 37 C.F.R. § 1.560(b), dated May 8, 2006, in the Reexamination of U.S. Patent No. 6,030,790, Control No. 90/007,412.

Final Office Action mailed on May 11, 2006, in the Reexamination of U.S. Patent No. 6,030,790, Control No. 90/007,412.

Amendment and Reply Under 37 C.F.R. § 1.116, filed Jul. 10, 2006, from the Reexamination of U.S. Patent No. 6,030,790, Control No. 90/007,412.

Ex Parte Reexamination Advisory Action, mailed Aug. 3, 2006.
Communication and Request for an Interview, filed Aug. 8, 2006.
Petition for an Extension of Time, filed Aug. 8, 2006.
Statement of Substance of Interview Under 37 CFR § 1.560(b), filed Aug. 9, 2006.
Miscellaneous Communication, filed Aug. 11, 2006.
Amendment and Reply Under 37 CFR 1.116 and Statement of Substance of Interview Under 37 CFR § 1.560(b), filed Aug. 16, 2006.
Ex Parte Reexamination Interview Summary, mailed Aug. 16, 2006.
Petition for Extension of Time, Control No. 90/007,412, filed Sep. 7, 2006.
Statement of Substance of Interview, Control No. 90/007,412, filed Sep. 11, 2006.
Decision Granting Petition for Extension of Time, Control No. 90/007,412, mailed on Sep. 12, 2006.
Ex Parte Reexamination Advisory Action, Control No. 90/007,412, mailed on Sep. 19, 2006.
Miscellaneous Communication—Notice of Concurrent Proceeding, Control No. 90/007,412, filed Sep. 22, 2006.
Ex Parte Reexamination Interview Summary, Control No. 90/007,412, mailed on Oct. 10, 2006.
Notice of Appeal From the Examiner to the Board of Patent Appeals and Interferences, Control No. 90/007,412, filed Oct. 10, 2006.
Statement of Substance of Interview Under 37 CFR 1.560(b), from Reexamination Control No. 90/007,412, filed on Nov. 8, 2006.
Appeal Brief, from Reexamination Control No. 90/007,412, filed on Dec. 11, 2006.
Examiner's Answer to Appeal Brief, from Reexamination Control No. 90/007,412, filed on Feb. 28, 2007.
Reply Brief, from Reexamination Control No. 90/007,412, filed on Apr. 30, 2007.
Request for Oral Hearing, from Reexamination Control No. 90/007,412, filed on Apr. 30, 2007.
Record of Oral Hearing from Reexamination Control No. 90/007,412, dated Oct. 1, 2008.
Opposition Documents against EP Patent No. 0 783 522, dated Sep. 4, 2002.
Opposition Documents against EP Patent No. 0 783 522, dated Sep. 5, 2002.
Opposition Documents against EP Patent No. 0 783 522, dated Dec. 10, 2003.
Official communication issued by the EPO on Jul. 8, 2004 in the opposition against EP Patent No. 0 783 522.
English translation of the official communication issued by the EPO on Jul. 8, 2004 in the opposition against EP Patent No. 0 783 522.
Summons to Oral Proceedings—Patent No. 95934629.7-2405/0783522—Ref. G1263 EP/OPP OPPO.01, mailed Mar. 18, 2005.
Certified English translation of Summons to Oral Proceedings—Patent No. 95934629.7-2405/0783522—Ref. G1263 EP/OPP OPPO.01, mailed Mar. 18, 2005.
Written Submissions in Preparation of the Oral Proceedings Scheduled for Nov. 15, 2005, submissions dated Sep. 15, 2005.
Petition Filed by Von Kreisler Selting Werner with the European Patent Office on Sep. 15, 2005.
English Translation of the Petition Filed by Von Kreisler Selting Werner with the European Patent Office on Sep. 15, 2005.
Official Communication by the European Patent Office on Sep. 29, 2005.
English Translation of the Official Communication by the European Patent Office on Sep. 29, 2005.
Petition filed by Patentee in response to the Official Communication dated Sep. 29, 2005 (in German).
Brief Communication from the Opposition Division dated Oct. 5, 2005 (in German).
Decision of the European Patent Office regarding revocation of European Patent No. 0 783 522, dated Jan. 10, 2007.
Response to the Grounds of Appeal, from Opposition to EP 0 783 522, filed Oct. 9, 2007.
Declaration of Hans H. Linden (D22), dated Oct. 9, 2007.
Concession Report for 1994 of the Dutch Mailing Service KPN (D23).
Opposition Documents against JP Patent No. 3457004, Opposition No. 2003-73801, dated Dec. 29, 2003.
Opposition Documents against JP Patent No. 3457004, Opposition No. 2003-73801, dated Apr. 13, 2004.
Notification of Reasons for Revocation, dated Jul. 9, 2004.
Notification of Invalid Judgment of Patent 3457004 by Japanese Patent Office, Mar. 2005.
English translation of Notification of Invalid Judgment of Patent 3457004 by Japanese Patent Office, Mar. 2005.
Judgment for the Invalidation of Japanese Patent No. 3457004, cover letter dated Dec. 7, 2005.
Case concerning petition for revocation of court ruling No. 10406, 2006, Plaintiff's Brief, Nov. 9, 2006 (Japanese litigation document and English translation, requesting withdrawal of the Japanese Patent Office's invalidation of JP Patent No. 3457004).
Written Answer, Nov. 9, 2006 (Japanese litigation document and English translation, requesting withdrawal of the Japanese Patent Office's invalidation of JP Patent No. 3457004).
Description of Evidence, Nov. 9, 2006 (Japanese litigation document and English translation, requesting withdrawal of the Japanese Patent Office's invalidation of JP Patent No. 3457004).
Brief (The first), Nov. 14, 2006 (Japanese litigation document and English translation, requesting withdrawal of the Japanese Patent Office's invalidation of JP Patent No. 3457004).
Minutes (Decision) from the Supreme Judicial Court of Japan, 2007 Case # 333 and 371, dated Feb. 5, 2008 (with English translation).
Complaint for Direct Patent Infringement, 35 U.S.C. § 271(a); and Inducing Patent Infringement, 35 U.S.C. § 271(b), filed Oct. 26, 2004 in *Scantibodies Laboratory, Inc.* v. *Immutopics, Inc.*, Case No. CV04-8871 GPS (MANx) United States District Court for the Central District of California.
Plaintiff Scantibodies Laboratory, Inc.'s Certificate of Interested Parties and Corporate Disclosure Statement (Fed. R. Civ. Proc. 7.1 and Central District Local Rule 7.1-1), filed Oct. 26, 2004.
Plaintiff Scantibodies Laboratory, Inc.'s Notice of Related Cases Pursuant to Central District Local Rule 83-1.3, filed Oct. 26, 2004.
Report on the Filing or Determination of an Action Regarding a Patent, Filed Oct. 26, 2004.
Defendants' Answer to Plaintiffs Complaint and Counterclaims, filed Dec. 3, 2004.
Certification and Notice of Interested Parties, filed Dec. 3, 2004.
Defendants' First Amended Answer to Plaintiff's Complaint and Counterclaims, filed Dec. 21, 2004.
Defendants' Second Amended Answer to Plaintiff's Complaint and Counterclaims, filed Dec. 31, 2004.
Plaintiff's Reply to Defendants' Counterclaims, filed Jan. 27, 2005.
Joint Report of Rule 26(f) Conference of Counsel, filed Feb. 7, 2005.
Civil Minutes—General, filed Feb. 14, 2005.
Initial Rule 26(A) Disclosure by Plaintiff Scantibodies Laboratory, Inc., filed Feb. 28, 2005.
Defendant's Initial Disclosures Pursuant to Fed. R. Civ. P. 26(a), filed Feb. 28, 2005.
Why Nichols is our PTH Vendor, submitted in Defendant's Supplemental Initial Disclosures.
Scantibodies' First Set of Interrogatories to Defendants/Counterclaimants Immutopics, Inc. and Immutopics International, LLC (Nos. 1-14), filed Mar. 7, 2005.
Scantibodies' First Request for Production of Documents to Defendants/Counterclaimants Immutopics, Inc. and Immutopics International, LLC (Nos. 1-63), filed Mar. 7, 2005.
Defendants' First Set of Interrogatories to Plaintiff Pursuant to Fed. R. Civ. P. 33 (Nos. 1-4), filed Mar. 9, 2005.
Defendants' First Request for Admissions to Plaintiff Pursuant to Fed. R. Civ. P. 36 (Nos. 1-11), filed Mar. 9, 2005.
Defendants' First Requests for Production of Documents and Things Pursuant to Fed. R. Civ. P. 34 (Nos. 1-51), filed Mar. 9, 2005.
Stipulation and Protective Order Regarding Confidential Information, filed Mar. 18, 2005.
Plaintiff's Responses to Defendants' First Set of Interrogatories Pursuant to Fed. R. Civ. P. 33 (Nos. 1-4), filed Apr. 22, 2005.
Plaintiff's Responses to Defendants' First Set of Requests for Admissions Pursuant to Fed. R. Civ. P. 36 (Nos. 1-11), filed Apr. 22, 2005.
Defendants' Second Request for Admissions to Plaintiff Pursuant to Fed. R. Civ. P. 36 (No. 12-21), filed Jun. 8, 2005.

Application for an Order for the Issuance of Letter Rogatory; Memorandum of Points and Authorities; Declaration of Dan P. Sedor, filed Jun. 9, 2005.
Letter Rogatory, filed Jun. 9, 2005.
Scantibodies' Second Set of Interrogatories to Defendants/Counterclaimants Immutopics, Inc. and Immutopics International, LLC (Nos. 15-19) filed Jun. 10, 2005.
Scantibodies' Second Request for Production of Documents to Defendants/Counterclaimants Immutopics, Inc. and Immutopics International, LLC (Nos. 6469) filed Jun. 10, 2005.
Scantibodies' First Request for Admissions to Defendants/Counterclaimants Immutopics, Inc. and Immutopics International, LLC )Nos. 1-110), filed Jun. 10, 2005.
Objections of Third-party Respondent Richard E. Reitz. M.D., filed Jun. 13, 2005.
Notice of Deposition of Scantibodies Laboratory, Inc. Pursuant to F.R.C.P. 30(b)(6), filed Jun. 17, 2005.
Scantibodies' Third Request for Production of Documents to Defendants/Counterclaimants Immutopics, Inc. and Immutopics International, LLC (No. 70) filed Jul. 1, 2005.
Plaintiff/Counterdefendant's Objections to Defendant/Counterclaimant's Deposition Notice Pursuant to F.R.C.P. 30(B)(6), filed Jul. 8, 2005.
Plaintiff's Responses to Defendants' Second Set of Interrogatories Pursuant to Fed. R. Civ. P. 33 (No. 5), filed Jul. 12, 2005.
Responses to Defendants' Second Request for Admissions to Plaintiff Pursuant to Fed. R. Civ. P. 36 (Nos. 12-21), filed Jul. 12, 2005.
Defendants' Third Request for Admissions to Plaintiff Pursuant to Fed. R. Civ. p. 36 (Nos. 22-23), filed Jul. 12, 2005.
Defendants/Counterclaimants' Response to Scantibodies' First Requests for Admissions (Nos. 1-110), filed Jul. 12, 2005.
Defendants/Counterclaimants' Response to Scantibodies' Second Request for Production of Documents (Nos. 64-69), filed Jul. 13, 2005.
Defendants' Fourth Request for Admissions to Plaintiff Pursuant to Fed. R. Civ. p. 36 (Nos. 24-37), filed Jul. 15, 2005.
Objections to Subpoena and Notice of Deposition of Peng Chen, filed Jul. 25, 2005.
Defendants' Fifth Request for Admissions to Plaintiff Pursuant to Fed. R. Civ. p. 36 (Nos. 38-47), filed Jul. 27, 2005.
Scantibodies' Third Set of Interrogatories to Defendants/Counterclaimants Immutopics, Inc. and Immutopics International, LLC (Nos. 20-24), filed Aug. 1, 2005.
Scantibodies' Second Request for Admissions to Defendants/Counterclaimants Immutopics, Inc. and Immutopics International, LLC (Nos. 111-276), filed Aug. 1, 2005.
Scantibodies' Fourth Request for Production of Documents and Things to Defendants/Counterclaimants Immutopics, Inc. and Immutopics International, LLC (Nos. 7188), filed Aug. 1, 2005.
Defendants/Counterclaimants' Response to Scantibodies' Third Request for Production of Documents (No. 70), filed Aug. 1, 2005.
Letter from Immutopics' counsel to Scantibodies' counsel dated Aug. 5, 2005.
Plaintiff's Response to Defendants' Third Request for Admissions Pursuant to Fed. R. Civ. p. 36 (Nos. 22-23), filed Aug. 11, 2005.
Plaintiff's Response to Defendants' Fourth Request for Admissions Pursuant to Fed. R. Civ. p. 36 (Nos. 24-37), filed Aug. 15, 2005.
Notice of Service Deposition Subpoena and Subpoena Duces Tecum on Michael A. Levine, filed Aug. 16, 2005.
Notice of Service Subpoena Duces Tecum on Lori J. Sokoll, filed Aug. 16, 2005.
Notice of Service of Subpoena Duces Tecum on Diasorin Inc., filed Aug. 16, 2005.
Notice of Service of Subpoena Duces Tecum on the Johns Hopkins Medical Institutions, filed Aug. 16, 2005.
Defendants/Counterclaimants' Response to Scantibodies' Second Set of Interrogatories (Nos. 15-19), filed Aug. 16, 2005.
Notice of Service of Deposition Subpoena and Subpoena Duces Tecum on John W. Colford, filed Aug. 17, 2005.
Notice of Service of Deposition Subpoena and Subpoena Duces Tecum on Michael Salvati, filed Aug. 17, 2005.
Declaration of M. Andrew Woodmansee in Support of Motion to Quash Immutopics' Subpoena to Third-Party Dr. Richard Lerner and for Attorneys' Fees, filed Aug. 18, 2005.
Notice of Service of Deposition Subpoena and Subpoena Duces Tecum on Gordon D. Macfarlane, filed Aug. 18, 2005.
Declaration of John Colford, dated Aug. 18, 2005.
Memorandum of Points and Authorities in Support of Plaintiff's Motion to Stay Action Pending Resolution of Plaintiff's Request to Patent and Trademark Office for Reexamination of Patent-In-Suit, filed Aug. 22, 2005.
Declaration of Brian W. Kasell in Support of Plaintiff's Motion to Stay Action Pending Resolution of Plaintiff's Request to Patent and Trademark Office for Reexamination of Patent-In-Suit, filed Aug. 22, 2005.
Stipulation Regarding Briefing Schedule for Plaintiff's Motion to Stay Action Pending Resolution of Plaintiff's Request to Patent and Trademark Office for Reexamination of Patent-In-Suit [Proposed] Order Thereon, filed Aug. 22, 2005.
Notice of Service of Subpoena Duces Tecum on Diasorin Inc., filed Aug. 24, 2005.
Notice of Service of Subpoena Duces Tecum on Todd Jensen, filed Aug. 24, 2005.
Notice of Service of Subpoena Duces Tecum on Jon Spring, filed Aug. 24, 2005.
Plaintiff's Response to Defendants' Fifth Request for Admissions Pursuant to Fed. R. Civ. p. 36 (Nos. 38-47), filed Aug. 25, 2005.
Defendants/Counterclaimants' Response to Scantibodies' Third Set of Interrogatories (Nos. 20-24), filed Aug. 31, 2005.
Defendants/Counterclaimants' Response to Scantibodies' Fourth Request for Production of Documents (Nos. 71-88), filed Aug. 31, 2005.
Defendant/Counterclaimants' Response to Scantibodies' Second Request for Admissions (Nos. 111-276), filed Aug. 31, 2005.
Defendant's Opposition to Motion to Stay Action Pending Resolution of Re-examination of Patent-In-Suit, filed Sep. 2, 2005.
Declaration of Matthew Newboles in Support of Defendant's Opposition for Motion to Stay, filed Sep. 2, 2005.
Declaration of Richard Zahradnik in Support of Defendants' Opposition for Motion to Stay, filed Sep. 2, 2005.
Plaintiff's Evidentiary Objections to and Request to Strike the Declarations of Matthew Newboles and Richard Zahradnik and a Portion of Defendants' Opposition Memorandum in Support of Defendants' Opposition to Plaintiff's Motion for Stay, filed Sep. 12, 2005.
Declaration of David Cantor in Support of Plaintiff's Reply to Defendants' Opposition to Plaintiff's Motion to Stay, filed Sep. 12, 2005.
Supplemental Declaration of Richard Zahradnik in Support of Defendants' Opposition for Motion to Stay, filed Sep. 15, 2005.
Request for Judicial Notice of Recently Discovered Ruling, Re: Motion for Stay, filed Sep. 15, 2005.
Plaintiff's Evidentiary Objections to and Request to Strike the Supplemental Declaration of Richard Zahradnik in Support of Defendants' Opposition to Plaintiff's Motion for Stay, filed Sep. 19, 2005.
Order Granting Plaintiff's Motion to Stay Proceedings, filed Sep. 20, 2005.
Notice of Patent and Trademark Office's Grant of Plaintiff's Request for Reexamination, filed Sep. 22, 2005.
Bate Stamped Documents Index.
BioActive Intact PTH Assays, bate stamped IMU-2839-2840.
Human BioActive Intact PTH ELISA Kit, bate stamped IMU-2841-2844.
Human BioActive PTH 1-84 ELISA Kit, bate stamped IMU-2845-2846.
PTH (1-84) Specific Label, bate stamped SC 010159.
Human BioActive PTH 1-84 ELISA Kit Label, bate stamped SC 010163.
Whole PTH (1-84) Specific Label, bate stamped SC 010168.
NKF 2004 PTH Abstracts, bate stamped SC 01483-01496.
The Rise in Adynamic Bone Disease in ERSD Patients and the Changing Spectrum of Renal Osteodystrophy, bate stamped SC 001268-001276.

Court Docket from PACER for *Scantibodies Laboratory, Inc.*, v. *Immutopics, Inc.*, from the US District Court for the Central District of California, docket accessed May 25, 2006.
Court Docket from PACER for *Scantibodies Laboratory, Inc.*, v. *Immutopics, Inc.*, from the US District Court for the Central District of California, docket accessed Sep. 8, 2006.
Joint Notice of Status of Reexamination of Patent-In-Suit, filed Sep. 29, 2006 in *Scantibodies* v. *Immutopics*, USDC for the Central District of California, Case No. CV 04-8871 GPS (MANx).
Court Docket from PACER for *Scantibodies Laboratory, Inc.*, v. *Immutopics, Inc.*, from the US District Court for the Central District of California, docket accessed May 23, 2007.
Memorandum of Points and Authorities in Support of Plaintiff's Motion for Partial Summary Judgment on Defendants' Counterclaim of Patent Invalidity Under 35 U.S.C. §§ 102 and 103, filed Nov. 14, 2007.
Plaintiff's Statement of Uncontroverted Facts and Conclusions of Law in Support of Its Motion for Partial Summary Judgment on Defendants' Counterclaim of Patent Invalidity Under 35 U.S.C. §§ 102 and 103, filed Nov. 14, 2007.
Declaration of Brian W. Kasell in Support of Plaintiff's Motion for Partial Summary Judgment on Defendants' Counterclaim of Patent Invalidity Under 35 U.S.C. §§ 102 and 103, filed Nov. 14, 2007.
Court Docket From PACER for *Scantibodies Laboratory, Inc.* v. *Immutopics, Inc.*, currently pending at the United States District Court for the Central District of California (Western Division), Case No. CV 04-08871 MRP (MANx), docket accessed Nov. 29, 2007.
Memorandum of Points and Authorities in Support of Plaintiff's Opposition to Defendants' Motion for Summary Judgment of Patent Invalidity for Lack of Enablement, filed Dec. 18, 2007.
Memorandum of Points and Authorities in Support of Plaintiff's Opposition to Defendants' Motion for Summary Judgment of Patent Invalidity for Violation of on Sale Bar and for Obviousness Over the Prior Art, filed Dec. 18, 2007.
Memorandum of Points and Authorities in Support of Plaintiff's Opposition to Defendants' Motion for Summary Judgment for Failing to Disclose the Best Mode, filed Dec. 18, 2007.
Declaration of Brian W. Kasell in Support of Plaintiff's Oppositions to Defendants' Summary Judgment Motions for: 1. Failing to Disclose the Best Mode; 2. Violation of on Sale Bar and for Obviousness; 3. Lack of Enablement; and 4. Non-Infringement, filed Dec. 18, 2007.
Declaration of Thomas L. Cantor in Support of Plaintiff's Opposition to Defendants' Motions for Summary Judgment, filed Dec. 18, 2007.
Plaintiff's Statement of Genuine Issues of Material Fact in Support of its Opposition to Defendants' Motion for Summary Judgment of Patent Invalidity for Violation of on Sale Bar and Obviousness Over the Prior Art, filed Dec. 18, 2007.
Plaintiff's Statement of Genuine Issues of Material Fact in Support of its Opposition to Defendants' Motion for Summary Judgment of Patent Invalidity for Lack of Enablement, filed Dec. 18, 2007.
Plaintiff's Statement of Genuine Issues of Material Fact in Support of its Opposition to Defendants' Motion for Summary Judgment for Failing to Disclose the Best Mode, filed Dec. 18, 2007.
Order Denying Scantibodies' Motion for Partial Summary Judgment on Defendants' Counterclaim of Patent Invalidity, filed Dec. 28, 2007.
Court Docket From PACER for *Scantibodies Laboratory, Inc.* v. *Immutopics, Inc.*, currently pending at the United States District Court for the Central District of California (Western Division), Case No. CV 04-08871 MRP (MANx), docket accessed Jan. 5, 2008.
Plaintiff's Amendment to Statement of Genuine Issues of Material Fact in Support of its Opposition to Defendants' Motion for Summary Judgment for Failing to Disclose the Best Mode, filed Jan. 30, 2008.
Immutopics' Response to Plaintiff's Amendment to Statement of Genuine Issues of Material Fact in Support of its Opposition to Defendants' Motion for Summary Judgment for Failing to Disclose the Best Mode and Request for Sanctions, filed Jan. 31, 2008.
Court Docket From PACER for *Scantibodies Laboratory, Inc.* v. *Immutopics, Inc.*, currently pending at the United States District Court for the Central District of California (Western Division), Case No. CV 04-08871 MRP (MANx), docket accessed Feb. 5, 2008.
Joint Statement of Contentions Re Meaning of Terms in Reexamination Claims of U.S. Patent No. 6,689,566; Proposed Schedule Re Markman Hearing, filed Feb. 11, 2008.
Plaintiff's Ex Parte Application Regarding Handling and Use of Documents Filed Under Seal; Memorandum of Points and Authorities; Declaration of Brian W. Kasell, filed Feb. 12, 2008.
[Corrected] Plaintiff's Ex Parte Application Regarding Handling and Use of Documents Filed Under Seal; Memorandum of Points and Authorities; Declaration of Brian W. Kasell, filed Feb. 12, 2008.
Defendants' Opposition Memorandum to Plaintiff's Ex Parte Application Regarding Handling and Use of Documents Filed Under Seal, filed Feb. 12, 2008.
Declaration of Matthew A. Newboles in Support of Defendants' Opposition to Plaintiff's Ex Parte Application Regarding Handling and Use of Documents Filed Under Seal, filed Feb. 12, 2008.
Plaintiff's Response to Defendants' Opposition to Plaintiff's Ex Parte Application Regarding Handling and Use of Documents Filed Under Seal; Supplemental Declaration of Brian W. Kasell, filed Feb. 13, 2008.
Court Docket From PACER for *Scantibodies Laboratory, Inc.* v. *Immutopics, Inc.*, currently pending at the United States District Court for the Central District of California (Western Division), Case No. CV 04-08871 MRP (MANx), docket accessed Feb. 27, 2008.
Immutopics, Inc. and Immutopics International, LLC's Claim Construction Brief, filed Mar. 19, 2008.
Declaration of Matthew A. Newboles in Support of Immutopics, Inc. and Immutopics International, LLC's Claim Construction Brief, filed Mar. 19, 2008.
Plaintiff's Brief in Support of Construction of Terms in Reexamination Claims of U.S. Patent No. 6,689,566, filed Mar. 19, 2008.
Declaration of Brian W. Kasell in Support of Plaintiff's Brief in Support of Construction of Terms in Reexamination Claims of U.S. Patent No. 6,689,566, filed Mar. 19, 2008.
Declaration of Monica Ranes-Goldberg, Ph.D., filed Mar. 19, 2008.
Court Docket From PACER for *Scantibodies Laboratory, Inc.* v. *Immutopics, Inc.*, currently pending at the United States District Court for the Central District of California (Western Division), Case No. CV 04-08871 MRP (MANx), docket accessed Mar. 20, 2008.
Claim Construction Order from *Scantibodies Laboratory, Inc.*, v. *Immutopics, Inc.*, filed May 1, 2008.
Order Granting Immutopics' Motion for Summary Judgment of Non-Infringement of the '566 Patent; Denying Immutopics' Motions for Summary Judgment Based on Invalidity of the '566 Patent, filed May 16, 2008.
Court Docket From PACER for *Scantibodies Laboratory, Inc.* v. *Immutopics, Inc.*, currently pending at the United States District Court for the Central District of California (Western Division), Case No. CV 04-08871 MRP (MANx), docket accessed Jul. 1, 2008.
Plaintiff's Notice of Motion and Motion for Relief Under Protective Order Regarding Confidential Information, filed Jul. 11, 2008.
Rule 37 Joint Stipulation Re Plaintiff's Motion for Relief Under Protective Order Regarding Confidential Information, filed Jul. 11, 2008.
Declaration of Brian W. Kasell in Support of Rule 37 Joint Stipulation Re Plaintiff's Motion for Relief Under Protective Order Regarding Confidential Information, filed Jul. 11, 2008.
Declaration of Matthew A. Newboles in Support of Defendants' and Counterclaimants' Opposition to Joint Stipulation Re Plaintiff's Motion for Relief Under Protective Order Regarding Confidential Information, filed Jul. 11, 2008.
Minutes of Status Conference, filed Jul. 18, 2008.
Plaintiff's Supplemental Memorandum in Support of Its Motion for Relief Under Protective Order Regarding Confidential Information, filed Jul. 22, 2008.
Judgment, filed Jul. 30, 2008.
Report on the Determination of an Action Regarding a Patent or Trademark, filed Jul. 31, 2008.
Court Docket From PACER for *Scantibodies Laboratory, Inc.* v. *Immutopics, Inc.*, currently pending at the United States District Court for the Central District of California (Western Division), Case No. CV 04-08871 MRP (MANx), docket accessed Aug. 4, 2008.
Notice of Appeal, filed Aug. 4, 2008.
Notice of Docketing, filed Aug. 22, 2008.

Court Docket From PACER for *Scantibodies Laboratory, Inc.* v. *Immutopics, Inc.*, the United States District Court for the Central District of California (Western Division), Case No. CV 0408871 MRP (MANx), docket accessed Aug. 26, 2008.
Amended Notice of Appeal, filed Aug. 28, 2008.
Stipulation Regarding Amendment of Judgment Nunc Pro Tunc to Include Determination of "No Just Reason for Delay" Pursuant to Rule 54(b), filed Nov. 5, 2008.
Amended Claim Construction Order, filed Nov. 26, 2008.
Court Docket From PACER for *Scantibodies Laboratory, Inc.* v. *Immutopics, Inc.*, the United States District Court for the Central District of California (Western Division), Case No. CV 04-08871 MRP (MANx), docket accessed Dec. 1, 2008.
Court Docket From PACER for *Scantibodies Laboratory, Inc.* v. *Immutopics, Inc.*, the United States District Court for the Central District of California (Western Division), Case No. CV 04-08871 MRP (MANx), docket accessed Jan. 7, 2009.
Immutopics, Inc. and Immutopics International, LLC's Comments to Amended Claim Construction Order, filed Jan. 16, 2009.
Declaration of Matthew A. Newboles in Support of Immutopics, Inc. and Immutopics International, LLC's Comments to Amended Claim Construction Order, filed Jan. 16, 2009.
Plaintiff's Memorandum on its Positions Concerning the Nov. 26, 2008 Amended Claim Construction Order, filed Jan. 16, 2009.
Court Docket From PACER for *Scantibodies Laboratory, Inc.* v. *Immutopics, Inc.*, the United States District Court for the Central District of California (Western Division), Case No. CV 04-08871 MRP (MANx), docket accessed Jan. 20, 2009.
Court Docket From PACER for *Scantibodies Laboratory, Inc.* v. *Immutopics, Inc.*, currently pending at the United States Court of Appeals for the Federal Circuit, Case No. 2008-1522, docket accessed Aug. 26, 2008.
Court Docket From PACER for *Scantibodies Laboratory, Inc.* v. *Immutopics, Inc.*, currently pending at the United States Court of Appeals for the Federal Circuit, Case No. 2008-1522, docket accessed Dec. 1, 2008.
Court Docket From PACER for *Scantibodies Laboratory, Inc.* v. *Immutopics, Inc.*, currently pending at the United States Court of Appeals for the Federal Circuit, Case No. 2008-1522, docket accessed Jan. 7, 2009.
Notice of Intent to Issue Ex Parte Reexamination Certificate from Control No. 90/007,412, mailed on Aug. 14, 2009.
Office Action from Canadian Patent Application No. 2,360,020, dated Jul. 16, 2009.
Second Amended Claim Construction Order, filed Feb. 9, 2009.
Amendment in Response to Non-Final Office Action from U.S. Appl. No. 10/760,091, filed Feb. 19, 2009.
Final Office Action from U.S. Appl. No. 11/437,428, mailed on Feb. 5, 2009.
Notice of Allowance from U.S. Appl. No. 10/617,489, mailed on Mar. 23, 2009.
Petition Decision from U.S. Appl. No. 10/617,489, mailed on Apr. 3, 2009.
First Preliminary Amendment and Request for Continued Examination from U.S. Appl. No. 11/799,726, filed Mar. 31, 2009.
Office Action from EP Application No. 06008181.7, dated Feb. 9, 2009.
Decision on Appeal from Control No. 90/007,412, decided Mar. 30, 2009.
Interview Summary from U.S. Appl. No. 10/168,185, mailed on Mar. 9, 2009.
Amendment in Response to Non-Final Office Action from U.S. Appl. No. 10/168,185, filed Apr. 13, 2009.
Declaration of Thomas L. Cantor in Support of Plaintiff's Opposition to Defendants' Motion for Summary Judgment of Non-Infringement in View of the Court's Second Amended Claim Construction Order, filed Mar. 30, 2009.
Notice of Errata Regarding Declaration of Thomas L. Cantor in Support of Plaintiff's Opposition to Defendants' Motion for Summary Judgment of Non-Infringement in View of the Court's Second Amended Claim Construction Order, filed Apr. 1, 2009.
Immutopics' Objections to the Declaration of Thomas L. Cantor in Support of Plaintiff's Opposition to Defendants' Motion for Summary Judgment of Non-Infringement in View of the Court's Second Amended Claim Construction Order, filed Apr. 13, 2009.
Court Docket From PACER for *Scantibodies Laboratory, Inc.* v. *Immutopics, Inc.*, the United States District Court for the Central District of California (Western Division), Case No. CV 0408871 MRP (MANx), docket accessed Apr. 21, 2009.
Wood, Ann. Clin. Biochem. (1992) 29:11-21.
Decision Returning Improper Papers from Control No. 90/007,685 and 90/007,732, mailed on Apr. 21, 2009.
Petition Decision from U.S. Appl. No. 10/641,780, mailed on May 8, 2009.
Final Office Action from U.S. Appl. No. 10/760,091, mailed on May 7, 2009.
Petition Decision from U.S. Appl. No. 10/760,091, mailed on May 8, 2009.
Notice of Non-Compliant Information Disclosure Statement from U.S. Appl. No. 10/945,608, mailed on May 7, 2009.
Petition Decision from U.S. Appl. No. 10/945,608, mailed on May 8, 2009.
Opposition Decision (with English summary) from Opposition against JP patent No. 3457004, dated Sep. 8, 2008.
Declaration of Julia A. Miller in Support of Nichols Institute Diagnostics, Inc.'s Motion for Leave to File Amended Complaint, filed Jan. 26, 2004.
Nichols Institute Diagnostics, Inc.'s Notice of Lodgement of Corrected Copy of Proposed Second Amended Complaint, Exhibit A to Declaration of Julia A. Miller in Support of Nichols' Jan. 26, 2004 Motion for Leave to File Amended Complaint, filed Feb. 23, 2004.
Declaration of Julia A. Miller in Support of Nichols Institute Diagnostics, Inc.'s Motion for Summary Judgment that the '790 Patent Claims are Valid and Infringed, filed Feb. 28, 2005.
Declaration of M. Andrew Woodmansee in Support of Motion for Summary Judgment Pursuant to 35 U.S.C. § 102(b) by Defendants *Scantibodies Clinical Laboratory, Inc.* and *Scantibodies Laboratory, Inc.*, filed Feb. 25, 2003.
Declaration of Brigham A. Fordham in Support of Scantibodies' Motion for Judgment on the Pleadings for Lack of Standing and Failure to Join an Indispensable Party or, in the Alternative, to Join a Necessary Party Pursuant to FRCP 19, filed Jul. 16, 2003.
Declaration of Peter R. Munson in Support of Nichols Institute Diagnostics, Inc.'s Opposition to Scantibodies' Motion for Judgment on the Pleadings for Lack of Standing and Failure to Join an Indispensable Party or, in the Alternative, to Join a Necessary Party Pursuant to FRCP 19, filed Sep. 18, 2003.
Declaration of M. Andrew Woodmansee in Support of Scantibodies' Motion for Judgment on the Pleadings for Lack of Standing and Failure to Join an Indispensable Party or, in the Alternative, to Join a Necessary Party Pursuant to FRCP 19, filed Sep. 24, 2003.
Declaration of Julia A. Miller in Support of Nichols Institute Diagnostics, Inc.'s Motion to Permit Service of its Supplemental Amended Complaint Under F.R.C.P. 15(d), filed Nov. 24, 2003.
Declaration of Katherine L. Parker in Support of Scantibodies' Reply to Nichols' Opposition to Motion for Judgment on the Pleadings and for Attorneys' Fees, filed Feb. 23, 2004.
Supplemental Expert Report of Larry W. Evans Pursuant to Rule 26(A)(2)(B), Fed. R. Civ. P.
Supplemental Expert Report of L. J. Deftos, MD, JD, LLM.
Expert Report of Joseph O. Falkinham, III, Ph.D. Adopting Supplemental Expert Report of L. J. Deftos, MD, JD, LLM.
Rebuttal Expert Report of Joseph O. Falkinham, III, Ph.D.
Rubuttal Expert Report of Ellen S. Vitetta, Ph.D.
Order Granting Scantibodies' Ex Parte Application for Leave to File Documents Under Seal, filed May 4, 2005.
Nichols Institute Diagnostics, Inc.'s Notice of and Ex Parte Application for Order to File Its Confidential Consolidated Declaration of April Alex in Support of Nichols' Opposition to Scantibodies' in Limine Motion Nos. 2 and 5 Under Seal, filed May 5, 2005.
Declaration of April Alex in Support of Nichols' Ex Parte Application for Order Sealing Its Confidential Consolidated Declaration of April Alex in Support of Nichols' Opposition to Scantibodies' in Limine Motion Nos. 2 and 5 Under Seal, filed May 5, 2005.

Confidential Consolidated Declaration of April Alex in Support of Nichols Institute Diagnostics, Inc.'s Opposition to Scantibodies' in Limine Motion Nos. 2 and 5, filed May 5, 2005.
Scantibodies' Ex Parte Application for Leave to File Documents Under Seal With Oppositions to Nichols' Motions in Limine, Filed May 5, 2005.
Declaration of Katherine L. Parker in Support of Scantibodies' Ex Parte Application for Leave to File Documents Under Seal, filed May 5, 2005.
Declaration of M. Andrew Woodmansee in Support of Scantibodies' Oppositions to Nichols' Motions in Limine, filed May 5, 2005.
Supplemental Exhibits to Joint Trial Brief [vol. 1 of 5], filed May 4, 2005.
Nichols Institute Diagnostics, Inc.'s Notice of and Ex Parte Application for Order to File Exhibits 12-14, 16-17, 19, 22, 25-26 and 28-33 of the Supplemental Exhibits to Joint Trial Brief Under Seal, filed May 4, 2005.
Declaration of April M. Alex in Support of Nichols' Ex Parte Application for Order to File Exhibits 12-14, 16-17, 19, 22, 25-26 and 28-33 of the Supplemental Exhibits to Joint Trial Brief Under Seal, filed May 4, 2005.
[Proposed] Order Granting Nichols Institute Diagnostics, Inc.'s Ex Parte Application to File Exhibits 12-14, 16-17, 19, 22, 25-26 and 28-33 of the Supplemental Exhibits to Joint Trial Brief Under Seal, filed May 4, 2005.
Deposition of Claude Arnaud, Exhibit No. 12.
Deposition of Thomas Cantor, Exhibit No. 13.
Deposition of Thomas Cantor, Exhibit No. 14.
Deposition of Damon Cook, Exhibit No. 16.
Deposition of Wolf-Georg Forssmann, Exhibit No. 17.
Deposition of Ping Gao, Exhibit No. 19.
Deposition of Thomas Godemeyer, Exhibit No. 22.
Deposition of Markus Magerlein, Exhibit No. 25.
Deposition of Markus Magerlein, Exhibit No. 26.
Deposition of Michael Nordstrom, Exhibit No. 28.
Deposition of K. Ramakrishan, Exhibit No. 29.
Deposition of K. Ramakrishan, Exhibit No. 30.
Deposition of Randall Ringold, Exhibit No. 31.
Deposition of Stephen Scheibel, Exhibit No. 32.
Deposition of Janet Sharp, Exhibit No. 33.
Order Granting Nichols Institute Diagnostics, Inc.'s Ex Parte Application to File the Declaration of James V. Fazio, III in Support of Nichols Institute Diagnostics, Inc.'s Motion in Limine No. 10 to Preclude Counsel From Objecting to Rule 30(B)(6) Designations Under Seal, filed May 4, 2004.
Order Granting Nichols Institute Diagnostics, Inc.'s Ex Parte Application to File Exhibits A, B, C, D, F, G, H, and J to the Consolidated Declaration of April Alex in Support of Nichols Institute Diagnostics, Inc.'s in Limine Motions Nos. 15-17 Under Seal, filed May 4, 2005.
Order Granting Nichols Institute Diagnostics, Inc.'s Ex Parte Application to File Exhibits B and C of the Consolidated Declaration of Jane K. Babin in Support of Nichols Institute Diagnostics, Inc.'s in Limine Motions Nos. 19-20 Under Seal, filed May 4, 2005.
Memorandum of Points and Authorities in Support of Scantibodies' Motion for Summary Judgment of Invalidity and Noninfringement, filed Feb. 18, 2005.
Declaration of Katherine L. Parker in Support of Scantibodies' Motion for Summary Judgment of Invalidity and Noninfringement, with Exhibits 1-39, filed Feb. 18, 2005.
Nichols Institute Diagnostics, Inc.'s Opposition to Motion for Summary Judgment of Invalidity and Non-Infringement, filed Mar. 7, 2005.
Declaration of Julia A. Miller in Support of Nichols Institute Diagnostics, Inc.'s Opposition to Motion for Summary Judgment of Invalidity and Non-Infringement, with Exhibits A-E, filed Mar. 7, 2005.
Declaration of Katherine L. Parker in Support of Scantibodies' Reply Motion for Summary Judgment of Invalidity and Noninfringement, with Exhibits 1-4, filed Mar. 14, 2005.
Deposition of Claude D. Arnaud, taken on Feb. 1, 2005.
Deposition of Gerald Bjorge, taken on Jan. 27, 2005.
Deposition of Thomas Cantor, taken on Aug. 27, 2003.
Deposition of Thomas Cantor (30(B)(6)), taken on Sep. 11, 2003.
Deposition of Damon Cook, taken on Jun. 16, 2003.
Deposition of Damon Cook (30(B)(6)), taken on Sep. 12, 2003.
Deposition of Joseph O. Falkinham, taken on Jan. 21, 2005.
Deposition of Wolf-Georg Forssmann, Ph.D., taken on Aug. 25, 2003.
Deposition of Ping Gao, M.D., taken on Jun. 18, 2003.
Deposition of Allen Garrett, taken on May 20, 2005.
Deposition of Thomas Godemeyer, taken on Oct. 6, 2004.
Deposition of Mark Gray, taken on Jun. 16, 2003.
Deposition of Dr. Richard Lerner, taken on Jan. 13, 2005.
Deposition of Dr. Richard Lerner, taken on Mar. 16, 2005.
Deposition of Markus Magerlein, Ph.D., taken on May 28, 2003.
Deposition of Markus Magerlein, Ph.D., taken on Aug. 10, 2004.
Deposition of Michael Nordstrom (30(B)(6)), taken on Sep. 17, 2003.
Deposition of K. Ramakrishan, Ph.D., (30(B)(6)), taken on Aug. 13, 2003.
Deposition of K. Ramakrishan, Ph.D., (30(8)(6)), taken on Sep. 3, 2003.
Deposition of Stephen Scheibe!, taken Aug. 8, 2003.
Deposition of Janet Sharp, taken on Aug. 19, 2003.
Deposition of Randolph Wall, taken Jan. 31, 2005.
Deposition of J. Stuart Woodhead, taken Jan. 18, 2005.
Deposition of Zan Yang, Ph.D., taken on Jun. 16, 2003.
Nichols Institute Diagnostics, Inc.'s Notice of and Ex Parte Application for Order to File Its Consolidated Confidential Declaration of April M. Alex in Support of (1) Nichols Institute Diagnostics, Inc.'s Motion for Judgment as a Matter of Law Re: Willfulness and in the Alternative for a New trial and (2) Nichols Institute Diagnostics, Inc.'s Motion for Enhanced Damages Under Seal, filed Jan. 27, 2006.
Consolidated Confidential Declaration of April M. Alex in Support of (1) Nichols Institute Diagnostics, Inc.'s Motion for Judgment as a Matter of Law Re: Willfulness and in the Alternative for a New trial and (2) Nichols Institute Diagnostics, Inc.'s Motion for Enhanced Damages, filed Jan. 27, 2006.
[Proposed] Order Granting Nichols Institute Diagnostics, Inc.'s Ex Parte Application to File Its Consolidated Confidential Declaration of April M. Alex in Support of (1) Nichols Institute Diagnostics, Inc.'s Motion for Judgment as a Matter of Law Re: Willfulness and in the Alternative for a New trial and (2) Nichols Institute Diagnostics, Inc.'s Motion for Enhanced Damages Under Seal, filed Jan. 27, 2006, order signed Judge Brewster on Jan. 31, 2006.
Confidential Deposition of Tom Cantor, taken on Jul. 11, 2005.
Memorandum of Points and Authorities in Support of Defendants' and Counterclaimants' Motion for Summary Judgment for Failing to Disclose the Best Mode, filed Nov. 13, 2007.
Declaration of Matthew A. Newboles in Support of Defendants' and Counterclaimants' Motion for Summary Judgment for Failing to Disclose the Best Mode, filed Nov. 13, 2007.
Memorandum of Points and Authorities in Support of Defendants' and Counterclaimants' Motion for Summary Judgment of Patent Invalidity for Violation of on Sale Bar and for Obviousness over the Prior Art, filed Nov. 13, 2007.
Declaration of Matthew A. Newboles in Support of Defendants' and Counterclaimants' Motion for Summary Judgment of Patent Invalidity for Violation of on Sale Bar and for Obviousness over the Prior Art, filed Nov. 13, 2007.
Memorandum of Points and Authorities in Support of Defendants' and Counterclaimants' Motion for Summary Judgment of Patent Invalidity for Lack of Enablement, filed Nov. 13, 2007.
Declaration of Matthew A. Newboles in Support of Defendants' and Counterclaimants' Motion for Summary Judgment of Patent Invalidity for Lack of Enablement, filed Nov. 13, 2007.
Memorandum of Points and Authorities in Support of Defendants' and Counterclaimants' Motion for Summary Judgment of Non-Infringement of the '566 Patent, filed Nov. 13, 2007.
Declaration of Jeffrey Lavigne in Support of Defendants' and Counterclaimants' Motion for Summary Judgment Based on Non-Infringement of the '566 Patent, filed Nov. 13, 2007.
Declaration of John W. Colford, M.D. in Opposition to Plaintiffs Motion for Partial Summary Judgment on Defendants' Counterclaim of Patent Invalidity Under 35 U.S.C. §§ 102 and 103, filed Dec. 17, 2007.
Defendants and Counterclaimants' Memorandum of Points and Authorities in Opposition to Plaintiffs Motion for Partial Summary Judgment on Defendants' Counterclaim of Patent Invalidity Under 35 U.S.C. §102 and 103, filed Dec. 17, 2007.
Declaration of Matthew A. Newboles in Opposition to Plaintiffs Motion for Partial Summary Judgment on Defendants' Counterclaim of Patent Invalidity Under 35 U.S.C. §§ 102 and 103, filed Dec. 14, 2007.
Defendant and Counterclaimants Immutopics, Inc.'s and Immutopics International, LLC's Statement of Genuine Issues in Opposition to Plaintiffs Motion for Partial Summary Judgment on Defendants' Counterclaim of Patent Invalidity Under 35 U.S.C. §§ 102 and 103, filed Dec. 14, 2007.
Confidential Declaration of Brian W. Kasell in Support of Plaintiffs Opposition to Defendant's Motion for Summary Judgment Based on Non-Infringement, filed Dec. 18, 2007.
Defendants and Counterclaimants Immutopics, Inc. and Immutopics International, LLC's Objections to the Declaration of Brian W. Kasell, filed Jan. 18, 2008.
Defendant's and Counterclaimant's Immutopics, Inc. and Immutopics International, LLC's Objections to the Declaration of Thomas L. Cantor, filed Jan. 18, 2008.
[Proposed] Statement of Uncontroverted Facts and Conclusion of Law in Support of Defendants' and Counterclaimants' Motion for Summary Judgment for Failing to Disclose the Best Mode, filed Jan. 18, 2008.
Immutopics' Reply Memorandum of Points and Authorities in Support of its Motion for Summary Judgment for Failure to Disclose the Best Mode, filed Jan. 18, 2008.
Supplemental Declaration of Matthew A. Newboles in Support of Defendants' and Counterclaimants' Reply for Motion for Summary Judgment of Patent Invalidity for Violation of Best Mode, filed Jan. 18, 2008.
Immutopics' Reply to Plaintiffs Statement of Genuine Issues of Material Fact in Support of its Opposition to Defendants' Motion for Summary Judgment for Failing to Disclose the Best Mode, filed Jan. 18, 2008.
Immutopics' Response to Plaintiffs Objections to the Declaration of Matthew A. Newboles in Support of Defendants' Motion for Summary Judgment of Patent Invalidity for Violation of Best Mode, filed Jan. 18, 2008.
Statement of Uncontroverted Facts and Conclusions of Law in Support of Defendants' and Counterclaimants' Motion for Summary Judgment of Patent Invalidity for Lack of Enablement, filed Jan. 18, 2008.
Immutopics Reply Memorandum of Points and Authorities in Support of its Motion for Summary Judgment of Patent Invalidity for Lack of Enablement, filed Jan. 18, 2008.
Supplemental Declaration of Matthew A. Newboles in Support of Defendants' and Counterclaimants' Reply for Motion for Summary Judgment of Patent Invalidity for Lack of Enablement, filed Jan. 18, 2008.
Immutopics' Reply to Plaintiffs Statement of Genuine Issues of Material Fact in Support of its Opposition to Defendants' Motion for Summary Judgment of Patent Invalidity for Lack of Enablement, filed Jan. 18, 2008.
Immutopics' Response to Plaintiffs Objections to the Declaration of Matthew A. Newboles in Support of Defendants' Motion for Summary Judgment of Patent Invalidity for Lack of Enablement, filed Jan. 18, 2008.
Declaration of Matthew A. Newboles in Support of Immutopics, Inc.'s Motion for Summary Judgment of Non-Infringement, filed Nov. 12, 2007.
[Proposed] Statement of Uncontroverted Facts and Conclusions of Law in Support of Defendants' Motion for Summary Judgment Based on Non-Infringement of the '566 Patent, filed Nov. 12, 2007.
Memorandum of Points and Authorities in Support of Plaintiffs Opposition to Defendants' Motion for Summary Judgment of Non-Infringement of the '566 Patent, filed Dec. 18, 2007.
Plaintiff's Statement of Genuine Issues of Material Fact in Support of Its Opposition to Defendants' Motion for Summary Judgment Based on Non-Infringement of the '566 Patent, filed Dec. 18, 2007.
Immutopics Reply Memorandum of Points and Authorities in Support of Its Motion for Summary Judgment of Non-Infringement of the '566 Patent, filed Jan. 18, 2008.

Supplemental Declaration of Matthew A. Newboles in Support of Reply for Defendants' Motion for Summary Judgment of Non-Infringement, filed Jan. 18, 2008.
Immutopics' Response to Plaintiffs Objections to the Declaration of Matthew A. Newboles in Support of Defendants' Motion for Summary Judgment of Non-Infringement of the '566 Patent, filed Jan. 18, 2008.
Immutopics' Reply to Plaintiffs Statement of Genuine Issues of Material Fact in Support of Its Motion for Summary Judgment Based on Non-Infringement of the '566 Patent, filed Jan. 18, 2008.
[Proposed] Statement of Uncontroverted Facts and Conclusions of Law in Support of Defendants' and Counterclaimants' Motion for Summary Judgment of Patent Invalidity for Violation of on Sale Bar and Obviousness Over the Prior Art, filed Nov. 13, 2007.
Immutopics Reply Memorandum of Points and Authorities in Support of Its Motion for Summary Judgment of Patent Invalidity for Violation of the of on Sale Bar and Obviousness Over the Prior Art, filed Jan. 18, 2008.
Supplemental Declaration of Matthew A. Newboles in Support of Defendants' and Counterclaimants' Reply for Motion for Summary Judgment of Patent Invalidity for Violation of on Sale Bar and Obviousness Over the Prior Art, filed Jan. 18, 2008.
Immutopics' Reply to Plaintiffs Statement of Genuine Issues of Material Fact in Support of its Opposition to Defendants' Motion for Summary Judgment of Patent Invalidity for Violation of on Sale Bar and Obviousness Over the Prior Art, filed Jan. 18, 2008.
Immutopics' Response to Plaintiffs Objections to the Declaration of Matthew A. Newboles in Support of Defendants' Motion for Summary Judgment of Patent Invalidity for Violation of on Sale Bar and Obviousness Over the Prior Art, filed Jan. 18, 2008.
Memorandum of Points and Authorities in Support of Immutopics' Motion for Summary Judgment of Non-Infringement of the '566 Patent in View of the Court's Second Amended Claim Construction Order, dated Mar. 6, 2009.
Declaration of Matthew A. Newboles in Support of Immutopics' Motion for Summary Judgment Based on Non-Infringement of the '566 Patent in View of the Court's Second Amended Claim Construction Order, dated Mar. 6, 2009.
Declaration of Jeffrey Lavigne in Support of Immutopics' Motion for Summary Judgment Based on Non-Infringement of the '566 Patent in View of the Court's Second Amended Claim Construction Order, dated Mar. 6, 2009.
Declaration of Thomas L. Cantor with Exhibit A, executed on Apr. 7, 2005.
Revised Order for Summary Judgment of Non-Infringement, filed Apr. 23, 2009.
Court Docket From PACER for *Scantibodies Laboratory, Inc.* v. *Immutopics, Inc.*, the United States District Court for the Central District of California (Western Division), Case No. CV 0408871 MRP (MANx), docket accessed Jun. 11, 2009.
Order—Bd.R. 104(a), filed Jun. 9, 2009, Patent Interference No. 105,575 (MPT).
Non-Final Office Action from U.S. Appl. No. 11/799,726, mailed on Jun. 11, 2009.
Barbier et al., J. Med. Chem. (1997) 40:1373-1380.
Nussbaum et al., J. Biol. Chem. (1980) 255:10183-10187.
Jameson and Wolf, The Antigenic Index: A Novel Algorithm for Predicting Antigenic Determinants, CABIOS 4, 1988, pp. 181-186.
Communication pursuant to Article 94(3) EPC for European Patent Application No. 06008181.7, mailed on Feb. 9, 2009, 1 page.
Response to Communication pursuant to Article 94(3) EPC for European Patent Application No. 06008181.7, dated Jun. 18, 2009, 20 pages.
Zahradnik Notification of Court Decision in Related Litigation, filed Jun. 16, 2009, from Patent Interference No. 105,575 (MPT).
Letter from Leonard Svensson regarding Patent Interference No. 105,575 (MPT), dated Jun. 17, 2009.
Restriction Requirement for U.S. Appl. No. 11/894,367, mailed on Jun. 12, 2009, 7 pages.
Declaration of Brian W. Kasell in Support of Plaintiff's Opposition to Immutopics' Motion to Declare Case Exceptional Pursuant to 35 U.S.C. § 285 and for Leave to Submit Detailed Description of Attorney Fees, filed on Jun. 15, 2009.

Memorandum of Points and Authorities in Opposition to Immutopics' Motion to Declare Case Exceptional Pursuant to 35 U.S.C. § 285 and for Leave to Submit Detailed Description of Attorney Fees, filed on Jun. 15, 2009.
Cantor Response to Zahradnik Notification of Court Decision in Related Litigation, from Patent Interference No. 105,575 (MPT), filed Jun. 23, 2009.
Summons to Attend Oral Proceedings, from an Opposition Against EP Patent No. 1 151 307, dated Jun. 29, 2009.
Final Judgment of Non-Infringement of the '566 Patent in View of the Court's Second Amended Claim Construction Order, filed Jul. 9, 2009.
Court Docket From PACER for *Scantibodies Laboratory, Inc. v. Immutopics, Inc.*, the United States District Court for the Central District of California (Western Division), Case No. CV 04-08871 MRP (MANx), docket accessed Jul. 15, 2009.
Petition Decision from U.S. Appl. No. 11/799,726, mailed on Jun. 26, 2009.
Petition Decision from U.S. Appl. No. 11/894,367, mailed on Jun. 29, 2009.
Response to Restriction Requirement and Amendment from U.S. Appl. No. 11/894,367, filed Jul. 13, 2009.
Statement of Substance of Interview from U.S. Appl. No. 10/617,489, filed Jul. 15, 2009.
Statement of Substance of Interview from U.S. Appl. No. 10/945,608, filed Jul. 15, 2009.
Non-Final Office Action from U.S. Appl. No. 12/286,620, mailed on May 1, 2009.
Response to Office Action from U.S. Appl. No. 12/286,620, filed Jul. 1, 2009.
Supplementary European Search Report for EP Application No. 04786049.9-2402, mailed on May 11, 2009, 5 pages.
Statement of Substance of Interview from U.S. Appl. No. 10/945,608, filed Aug. 13, 2009.
Response to the Summons to Attend Oral Proceedings from an Opposition Against EP Patent No. 1 151 307, dated Jul. 8, 2009 (with English translation).
Amendment in Response to Non-Final Office Action from U.S. Appl. No. 11/799,729, filed Aug. 31, 2009.
Memorandum Opinion and Order, Decision on Motions, from Patent Interference No. 105,575 (MPT), filed Sep. 30, 2009.
Judgment—Bd. R. 127, from Patent Interference No. 105,575 (MPT), filed Sep. 30, 2009.
Petition Decision from U.S. Appl. No. 10/617,489, mailed on Aug. 28, 2009.
Written Submissions of the Patentee in Respect of Opposition Against EP-B-1151307, filed Oct. 7, 2009, European Patent Office.
Communication to the European Patent Office from Opposition Against EP-B-1151307, dated Oct. 14, 2009.
Petition to Withdraw Application From Issue Pursuant to 37 CFR 1.313(c)(2) from U.S. Appl. No. 10/945,608, filed Oct. 1, 2009.
Decision on Petition from U.S. Appl. No. 10/945,608, mailed on Oct. 5, 2009.
Petition to Withdraw Application From Issue Pursuant to 37 CFR 1.313(c)(2) from U.S. Appl. No. 10/617,489, filed Oct. 1, 2009.
Decision on Petition from U.S. Appl. No. 10/617,489, mailed on Oct. 5, 2009.
Brief Communication from EP Opposition Against EP-B-1151307, dated Oct. 14, 2009.
Brief Communication from EP Opposition Against EP-B-1151307, dated Oct. 15, 2009.
NonConfidential Brief of Plaintiff-Appellant Scantibodies Laboratory, Inc., filed Oct. 26, 2009, United States Court of Appeals for the Federal Circuit, Case No. 2009-1481.
Court Docket from PACER for *Scantibodies Laboratory, Inc. v. Immutopics, Inc.*, currently pending at the United States Court of Appeals for the Federal Circuit, Case No. 2009-1481, docket accessed Oct. 28, 2009.
Preliminary Amendment from U.S. Appl. No. 10/617,489, filed Oct. 27, 2009.
Office Action from Australian patent application No. 2004266128, dated Sep. 10, 2009.
Request for Continued Examination and Preliminary Amendment from U.S. Appl. No. 10/760,091, filed Nov. 5, 2009.
Final Office Action from U.S. Appl. No. 11/799,726, mailed on Nov. 2, 2009.
Confidential Brief of Plaintiff-Appellant Scantibodies Laboratory, Inc., filed Oct. 26, 2009, United States Court of Appeals for the Federal Circuit, Case No. 2009-1481.
Communication to the European Patent Office from Opposition Against EP-B-1151307, dated Nov. 26, 2009 (with English Translation).
John et al., Journal of Clinical Endocrinology and Metabolism (1999) 84(11):4287-4290.
Slatopolsky et al., Journal of the American Society of Nephrology (1999) 10:625A.
Gao et al., J. Bone Miner. Res. (1999) 14:SU057, S446.
Decision Revoking European Patent No. 1 151 307, dated Jan. 14, 2010.
Notice of Allowance from U.S. Appl. No. 10/617,489, mailed on Nov. 30, 2009.
Notice of Allowance from U.S. Appl. No. 10/945,608, mailed on Dec. 1, 2009.
Statement of Substance of Interview from U.S. Appl. No. 10/945,608, filed Feb. 2, 2010.
Amendment After Final Action Under 37 CFR 1.116 from U.S. Appl. No. 11/799,726, filed Dec. 30, 2009.
Advisory Action from U.S. Appl. No. 11/799,726, mailed on Jan. 21, 2010.
Amendment in Response to Official Action from Canadian Patent Application No. 2,360,020, filed Jan. 14, 2010.
Non-Final Office Action from U.S. Appl. No. 10/760,091, mailed on Jan. 15, 2010.
Office Action from EP Patent Application No. 04786049.9 dated Dec. 30, 2009.
Non-Confidential Brief for Defendants-Appellees, filed Dec. 22, 2009, United States Court of Appeals for the Federal Circuit, Case No. 2009-1481.
Corrected Non-Confidential Brief for Defendants-Appellees, filed Jan. 8, 2010, United States Court of Appeals for the Federal Circuit, Case No. 2009-1481.
Reply Brief of Plaintiff-Appellant Scantibodies Laboratory, Inc., filed Jan. 12, 2010, United States Court of Appeals for the Federal Circuit, Case No. 2009-1481.
Non-Confidential Joint Appendix, vol. 1, filed Jan. 22, 2010, United States Court of Appeals for the Federal Circuit, Case No. 2009-1481.
Non-Confidential Joint Appendix, vol. 2, filed Jan. 22, 2010, United States Court of Appeals for the Federal Circuit, Case No. 2009-1481.
Confidential Brief for Defendants-Appellees, filed Dec. 22, 2009, United States Court of Appeals for the Federal Circuit, Case No. 2009-1481.
Corrected Confidential Brief for Defendants-Appellees, filed Jan. 8, 2010, United States Court of Appeals for the Federal Circuit, Case No. 2009-1481.
Confidential Joint Appendix, vol. 1, filed Jan. 22, 2010, United States Court of Appeals for the Federal Circuit, Case No. 2009-1481.
Confidential Joint Appendix, vol. 2, filed Jan. 22, 2010, United States Court of Appeals for the Federal Circuit, Case No. 2009-1481.
Bailie et al., Pharmacotherapy (2005) 25(12):1687-1707.
Second Supplemental Amendment from U.S. Appl. No. 10/641,780, filed Mar. 8, 2010.
Request for Continued Examination and Amendment Under 37 C.F.R. § 1.116 from U.S. Appl. No. 11/799,726, filed Mar. 2, 2010.
Response to Office Action from European Patent Application No. 04786049.9, filed Jul. 8, 2010, 29 pages.
Notice of Allowance from U.S. Appl. No. 10/641,780, mailed on Jul. 15, 2010.
Amendment in Response to Non-Final Office Action from U.S. Appl. No. 10/760,091, filed Jun. 14, 2010.
Amendment in Response to Non-Final Office Action from U.S. Appl. No. 11/799,726, filed Aug. 23, 2010.
Miscellaneous Communication from U.S. Appl. No. 10/641,780, mailed on Aug. 25, 2010.
Statement of Substance of Interviews from U.S. Appl. No. 10/641,780, filed Aug. 30, 2010.

Statement of Substance of Interview from U.S. Appl. No. 10/760,091, filed Aug. 30, 2010.
Notice of Allowance from U.S. Appl. No. 10/760,091, mailed on Sep. 8, 2010.
Final Office Action from U.S. Appl. No. 11/799,726, mailed on Sep. 30, 2010.
Notice of Appeal of Decision Revoking European Patent No. 1 151 307, dated Mar. 8, 2010.
Commencement of Proceedings Before the Board of Appeal for EP Patent No. 1 151 307, dated Mar. 30, 2010.
Recording of Oral Arguments on Apr. 7, 2010 from *Scantibodies* v. *Immutopics*, United States Court of Appeals for the Federal Circuit, Case No. 2009-1481, available online at: http://oralarguments.cafc.uscourts.gov/mp3/2009-1481.mp3.
Decision on Appeal of Summary Judgment, dated May 6, 2010, United States Court of Appeals for the Federal Circuit, Case No. 2009-1481.
Non-Final Office Action from U.S. Appl. No. 11/799,726, mailed on Apr. 22, 2010.
Statement of Substance of Interview from U.S. Appl. No. 10/641,780, filed May 14, 2010.
Statement of Grounds of Appeal under Article 108 EPC, filed May 21, 2010, from Opposition proceedings against EP Patent No. 1 151 307.
Statement of Substance of Interview from U.S. Appl. No. 10/760,091, filed Dec. 8, 2010.
Interview Summary from U.S. Appl. No. 10/760,091, mailed on Dec. 13, 2010.
Amendment in Response to Final Office Action from U.S. Appl. No. 11/799,726, filed Nov. 30, 2010.
Advisory Action from U.S. Appl. No. 11/799,726, mailed on Dec. 23, 2010.
Request for Continued Examination and Amendment from U.S. Appl. No. 11/799,726, filed Feb. 28, 2011.
Non-Final Office Action from U.S. Appl. No. 11/799,726, mailed on Mar. 23, 2011.
Amendment in Response to Non-Final Office Action from U.S. Appl. No. 11/799,726, filed Jul. 25, 2011.
Neugebauer et al., Biochemistry (1995) 34:8835-8842.
Communication from the European Patent Office from application No. 00902406.8, appealed as case No. T 0610/10-3.3.08, dated Sep. 8, 2010.
Minutes from the Oral Hearing in the Opposition Against EP Patent No. 783522, Appeal No. T0496/07-3304, dated Apr. 4, 2011.
Final Office Action from U.S. Appl. No. 11/799,726, mailed on Aug. 11, 2011.
Office Action from European Patent Application No. 04 786 049.9-2406, dated Jan. 17, 2012.
Brossard et al., Clinical Chemistry (2000) 46(5):697-703.
Ratcliffe et al., Clinical Chemistry (1989) 35(9):1957-1961.
Request for Continued Examination and Preliminary Amendment from U.S. Appl. No. 11/799,726, filed May 14, 2012.
Non-Final Office Action from U.S. Appl. No. 13/009,759, mailed on Jul. 10, 2012.
Notice of Allowance from Canadian Patent Application No. 2,360,020, dated Nov. 2, 2011.
Applicant Initiated Interview Summary from U.S. Appl. No. 11/799,726, filed Jun. 6, 2012.
Statement of Substance of Interview from U.S. Appl. No. 11/799,726, filed Jun. 29, 2012.
Statement of Substance of Interview from U.S. Appl. No. 11/799,726, filed Jul. 9, 2012.
Request for Continued Examination from U.S. Appl. No. 13/009,759, filed Feb. 2, 2012.
Second Preliminary Amendment from U.S. Appl. No. 13/009,759, filed Feb. 6, 2012.
Applicant Initiated Interview Summary from U.S. Appl. No. 13/009,759, filed Feb. 14, 2012.
Statement of Substance of Interview from U.S. Appl. No. 13/009,759, filed Mar. 6, 2012.
Request for Continued Examination from U.S. Appl. No. 11/799,726, filed Nov. 11, 2011.
Final Office Action and Applicant Initiated Interview Summary from U.S. Appl. No. 11/799,726, mailed on Feb. 13, 2012.
Statement of Substance of Interview from U.S. Appl. No. 11/799,726, filed Mar. 6, 2012.
Invalidation Request for Japanese Patent No. 4132677, dated Jan. 26, 2012 (in Japanese).
D'Amour et al., J. Clin. Invest. (1979) 63:89-98.
D'Amour et al., Am. J. Physiol. (1981) E208-E214.
Garner et al., Surgery (1999) 126(6):1132-1138.
Hackeng et al., Journal of Clinical Endocrinology and Metabolism (1986) 63(2):447-453.
Harman et al., Arch. Surg. (1999) 134:651-656.
Libutti et al., Surgery (1999) 1145-1151.
MacGregor et al., Bone and Mineral (1986) 41-50.
Martin et al., Medicina Clinica (1997) 109(6):201-206.
Newman and Ashby, Ann. Clin. Biochem. (1988) 25:654-660.
Rude, Otolaryngologic Clinics of North America (1996) 29(4):663-679.
Whole PTH, in Japanese (reference 23 from invalidation request).
Winer et al., Journal of Clinical Endocrinology and Metabolism (1998) 83(10):3480-3486.
Kousaka et al., Nuclear Medicine (1988) 28(8):813-820.
Schar et al., Rapid Communications in Mass Spectrometry (1991) 5:319-326.
Written Answer filed on May 17, 2012 in the invalidation proceeding against Japanese Patent No. 4132677, Appeal No. 2012-800004 (in Japanese).
Amendment in Response to Final Office Action from U.S. Appl. No. 11/799,726, filed Oct. 11, 2011.
Advisory Action from U.S. Appl. No. 11/799,726, mailed on Oct. 19, 2011.
Notice of Allowance from U.S. Appl. No. 13/009,759, mailed on Nov. 2, 2011.
Notice of Allowance and Examiner Initiated Interview Summary from U.S. Appl. No. 11/799,726, mailed on Jul. 13, 2012.
Heinrich et al., The Journal of Biological Chemistry (1984) 259(5):3820-3829.
Written Statement for Oral Proceeding, filed Sep. 18, 2012 in the invalidation proceeding against Japanese Patent No. 4132677, Appeal No. 2012-800004 (in Japanese).
Amendment in Response to Non-Final Office Action from U.S. Appl. No. 13/009,759, filed Oct. 10, 2012.
Non-Final Office Action from U.S. Appl. No. 13/009,759, mailed on Oct. 18, 2012.

* cited by examiner

Whole Human PTH (1-84)

Whole PTH

Big PTH 7-84 Fragment

METHODS, KITS, AND ANTIBODIES FOR DETECTING PARATHYROID HORMONE

I. CROSS-REFERENCE TO RELATED APPLICATIONS

The present application is continuation of U.S. patent application Ser. No. 11/799,726, filed on May 1, 2007, which is a divisional application of U.S. patent application Ser. No. 10/617,489, filed on Jul. 10, 2003, now allowed, which is a continuation-in-part of U.S. patent application Ser. No. 09/344,639, filed on Jun. 26, 1999, now U.S. Pat. No. 6,743,590 issued Jun. 1, 2004, which is a continuation-in-part of U.S. patent application Ser. No. 09/231,422, filed on Jan. 14, 1999, now U.S. Pat. No. 6,689,566 issued Feb. 10, 2004. The contents of the above patent applications are incorporated by reference herein in their entireties.

II. TECHNICAL FIELD

The present invention relates to novel compositions, methods and kits for differentiating parathyroid diseases in a subject. These compositions, methods and kits can be used, for example to differentiate hyperparathyroidism, high bone turnover, and adynamic bone disease from normal or non-disease states.

III. BACKGROUND OF THE INVENTION

Calcium plays an indispensable role in cell permeability, the formation of bones and teeth, blood coagulation, transmission of nerve impulse, and normal muscle contraction. The concentration of calcium ions in the blood is, along with calcitrol and calcitonin, regulated mainly by parathyroid hormone (PTH). Although calcium intake and excretion may vary, PTH serves through a feedback mechanism to maintain a steady concentration of calcium in cells and surrounding fluids. When serum calcium lowers, the parathyroid glands secrete PTH, affecting the release of stored calcium. When serum calcium increases, stored calcium release is retarded through lowered secretions of PTH.

The complete form of human PTH, (hPTH), is a unique 84 amino acid peptide (SEQ ID NO: 1), as is shown in FIG. 1. Researchers have found that this peptide has an anabolic effect on bone that involves a domain for protein kinase C activation (amino acid residues 28 to 34) as well as a domain for adenylate cyclase activation (amino acid residues 1 to 7). However, various catabolic forms of clipped or fragmented PTH peptides also are found in circulation, most likely formed by intraglandular or peripheral metabolism. For example, whole PTH can be cleaved between amino acids 34 and 35 to produce a (1-34) PTH N-terminal fragment and a (35-84) PTH C-terminal fragment. Likewise, clipping can occur between either amino acids 36 and 37 or 37 and 38. Recently, a large PTH fragment referred to as "non-(1-84) PTH" has been disclosed which is clipped closer to the N-terminal end of PTH. (See LePage, R., et al., *Clin. Chem.* 44: 805-810(1998).

The clinical need for accurate measurement of PTH is well demonstrated. Serum PTH level is one of the most important index for patients with the following diseases: familial hypocalciuric hypercalcemia; multiple endocrine neoplasia types I and II; osteoporosis; Paget's bone disease; primary hyperparathyroidism—caused by primary hyperplasia or adenoma of the parathyroid glands; pseudohypoparathyroidism; and renal failure, which can cause secondary hyperparathyroidism.

PTH plays a role in the course of disease in a patient with chronic renal failure. Renal osteodystrophy (RO) is a complex skeletal disease comprising osteitis fibrosa cystica (caused by PTH excess), osteomalacia—unmineralized bone matrix (caused by vitamin D deficiency), extraskeletal calcification/ossification (caused by abnormal calcium and phosphorus metabolism), and adynamic bone disease (contributed to by PTH suppression). Chronic renal failure patients can develop RO. Failing kidneys increase serum phosphorus (hyperphosphoremia) and decrease 1,25-dihydroxyvitamin D (1,25-D) production by the kidney. The former results in secondary hyperparathyroidism from decreased gastrointestinal calcium absorption and osteitis fibrosa cystica from increased PTH in response to an increase in serum phosphorus. The later causes hypocalcemia and osteomalacia. With the onset of secondary hyperparathyroidism, the parathyroid gland becomes less responsive to its hormonal regulators because of decreased expression of its calcium and vitamin D receptors. Serum calcium drops. RO can lead to digital gangrene, bone pain, bone fractures, and muscle weakness.

Determining circulating biologically active PTH levels in humans has been challenging. One major problem is that PTH is found at low levels, normally 10 pg/mL to 40 pg/mL (i.e., 1 pmol/L to 4 pmol/L). Coupled with extremely low circulating levels is the problem of the heterogeneity of PTH and its many circulating fragments. In many cases, immunoassays have faced substantial and significant interference from circulating PTH fragments. For example, some commercially available PTH kits have almost 100% cross-reactivity with the non-(1-84) PTH fragment. See the LePage article supra.

PTH immunoassays have varied over the years. One early approach is a double antibody precipitation immunoassay found in U.S. Pat. No. 4,369,138, issued to Arnold W. Lindall et alia. A first antibody has a high affinity for a (65-84) PTH fragment. A radioactive labeled (65-84) PTH peptide is added to the sample with the first antibody to compete for the unlabeled peptide. A second antibody is added which binds to any first antibody and radioactive labeled PTH fragment complex, thereby forming a precipitate. Both precipitate and supernatant can be measured for radioactive activity, and PTH levels can be calculated therefrom.

In an effort to overcome PTH fragment interference, immunoradiometric two-site assays for intact PTH (I-PTH) have been introduced, such as Allegro® Intact PTH assay by the Nichols Institute of San Juan Capistrano, Calif. In one version, a capture antibody specifically binds to the C-terminal portion of hPTH while a labeled antibody specifically binds to the N-terminal portion of the captured hPTH. In another, two monoclonal antibodies were used, both of which attached to the N-terminal portion of hPTH. (For the purposes of the present disclosure, the complete form of human PTH is referred to as "whole PTH" or "wPTH" as distinguished from "intact PTH" or "I-PTH" which can include not only wPTH, but also a large PTH fragment cleaved about amino acids 5 to 8.) Unfortunately, these assays have problems in that they measure but do not discriminate between w-PTH and I-PTH. This inability comes to the fore in hyperparathyroid patients and renal failure patients who have significant endogenous concentrations of large, non-whole PTH fragments.

Recently, researchers have made a specific binding assay directed to the large N-terminal PTH fragments. See Gao, P., et al., *Clinica Chimica Acta* 245: 39-59 (1996). This immunochemiluminometric assay uses two monoclonal antibodies to detect N-terminal (1-34) PTH fragments but not mid-portion PTH fragments or C-terminal PTH fragments. A key factor in the design of these assays is to eliminate any reaction with C-terminal PTH fragments.

Nevertheless, specific whole PTH assays have not been able to measure whole PTH at physiological levels. See, e.g., Magerlein, M., et al., *Drug Res.* 48:197-204 (1998). The present invention is intended to meet these and other needs in the art.

An important discovery leading to the present invention is that adynamic bone loses its capacity to buffer calcium and phosphate as the bones are shut down. In subjects afflicted with such conditions, they are unable to effectively buffer calcium as it enters their bodies through their diet. This calcium enters the blood stream and is thereafter shuttled to the soft tissues. The parathyroid gland is particularly subject to, and detrimentally affected by, this influx of calcium and thereby produces PTH fragments rather than, or in addition to, the active form of PTH. Accordingly, in subjects with adynamic bone, the concentration and production of PTH fragments is increased. In light of this and other related information, the measurement of PTH fragment levels, and particularly in conjunction with the measurement of whole PTH, can be used effectively to differentiate subjects having adynamic bone versus those having normal bone and high bone turnover rates.

There is a tremendous need to be able to non invasively separate the dialysis patients with ADN from those suffering from high bone turnover to avoid over treatment of ADN dialysis patients. Over treatment of dialysis patients with ADN is a frequent occurrence under presently utilized methods. For example, package inserts that proscribe the use of Zemplar® and Calcijex® (Abbott Laboratories), for example, are being used to treat thousands of dialysis patients that stand a great risk of over treatment under the proscribed protocols that do not account for circulating total PTH fragment levels. The present invention addresses these and other need in the art.

IV. DISCLOSURE OF THE INVENTION

In one embodiment, the present disclosure provides an isolated antibody that specifically binds to an N-terminal sequence of whole parathyroid hormone (PTH) and is capable of detecting said whole PTH at a physiological level in a mammalian sample, with a proviso that said isolated antibody avoids binding to a non-whole PTH fragment. Frequently, the isolated antibody is a monoclonal or polyclonal antibody. Also frequently, the binding between the antibody and the N-terminal sequence of whole PTH is dependent on the presence of amino acid residues 2-5 or 3-6 of the PTH.

In one aspect an isolated antibody of the present disclosure specifically binds to an epitope comprised in $PTH_{1-6}$, $PTH_{1-8}$, $PTH_{1-9}$, $PTH_{1-12}$, or $PTH_{3-12}$. Frequently, an isolated antibody of the present disclosure specifically binds to the parathyroid hormone peptide $PTH_{1-15}$ or $PTH_{1-8}$, wherein at least four amino acids in said peptide sequence are part of a reactive portion with the antibody. On occasion, an isolated antibody of the present disclosure specifically binds to an epitope comprised in $PTH_{1-5}$, $PTH_{1-7}$, $PTH_{1-8}$, $PTH_{1-10}$, $PTH_{1-11}$, $PTH_{1-13}$, $PTH_{1-14}$, $PTH_{1-15}$, $PTH_{1-16}$, $PTH_{1-17}$, $PTH_{1-18}$, $PTH_{1-19}$, $PTH_{1-20}$, $PTH_{1-21}$, $PTH_{1-22}$, $PTH_{1-24}$, $PTH_{1-25}$, $PTH_{1-26}$, $hPTH_{1-27}$, $PTH_{1-28}$, $PTH_{1-29}$, $PTH_{1-30}$, $PTH_{1-31}$, $PTH_{1-32}$, $PTH_{1-33}$, $PTH_{1-34}$, $PTH_{1-35}$, $PTH_{1-36}$, $PTH_{1-37}$, $PTH_{2-5}$, $PTH_{2-6}$, $PTH_{2-7}$, $PTH_{2-8}$, $PTH_{2-9}$, $PTH_{2-10}$, $PTH_{2-11}$, $PTH_{2-12}$, $PTH_{2-13}$, $PTH_{2-14}$, $PTH_{2-15}$, $PTH_{2-16}$, $PTH_{2-17}$, $PTH_{2-18}$, $PTH_{2-19}$, $PTH_{2-20}$, $PTH_{2-21}$, $PTH_{2-22}$, $PTH_{2-23}$, $PTH_{2-24}$, $PTH_{2-25}$, $PTH_{2-26}$, $PTH_{2-27}$, $PTH_{2-28}$, $PTH_{2-29}$, $PTH_{2-30}$, $PTH_{2-31}$, $PTH_{2-32}$, $PTH_{2-33}$, $PTH_{2-34}$, $PTH_{2-35}$, $PTH_{2-36}$, $PTH_{2-37}$, $PTH_{3-6}$, $PTH_{3-7}$, $PTH_{3-8}$, $PTH_{3-9}$, $PTH_{3-10}$, $PTH_{3-11}$, $PTH_{3-13}$, $PTH_{3-14}$, $PTH_{3-15}$, $PTH_{3-16}$, $PTH_{3-7}$, $PTH_{3-18}$, $PTH_{3-19}$, $PTH_{3-20}$, $PTH_{3-21}$, $PTH_{3-22}$, $PTH_{3-23}$, $PTH_{3-24}$, $PTH_{3-25}$, $PTH_{3-26}$, $PTH_{3-27}$, $PTH_{3-28}$, $PTH_{3-29}$, $PTH_{3-30}$, $PTH_{3-31}$, $PTH_{3-32}$, $PTH_{3-33}$, $PTH_{3-34}$, $PTH_{3-35}$, $PTH_{3-36}$, $PTH_{3-37}$, $PTH_{4-7}$, $PTH_{4-8}$, $PTH_{4-9}$, $PTH_{4-10}$, $PTH_{4-11}$, $PTH_{4-12}$, $PTH_{4-13}$, $PTH_{4-14}$, $PTH_{4-15}$, $PTH_{4-16}$, $PTH_{4-17}$, $PTH_{4-18}$, $PTH_{4-19}$, $PTH_{4-20}$, $PTH_{4-21}$, $PTH_{4-22}$, $PTH_{4-23}$, $PTH_{4-24}$, $PTH_{4-25}$, $PTH_{4-26}$, $PTH_{4-27}$, $PTH_{4-28}$, $PTH_{4-29}$, $PTH_{4-30}$, $PTH_{4-31}$, $PTH_{4-32}$, $PTH_{4-33}$, $PTH_{4-34}$, $PTH_{4-35}$, $PTH_{4-36}$, $PTH_{4-37}$, $PTH_{5-8}$, $PTH_{5-9}$, $PTH_{5-10}$, $PTH_{5-11}$, $PTH_{5-12}$, $PTH_{5-13}$, $PTH_{5-14}$, $PTH_{5-15}$, $PTH_{5-16}$, $PTH_{5-17}$, $PTH_{5-18}$, $PTH_{5-19}$, $PTH_{5-20}$, $PTH_{5-21}$, $PTH_{5-22}$, $PTH_{5-23}$, $PTH_{5-24}$, $PTH_{5-25}$, $PTH_{5-26}$, $PTH_{5-27}$, $PTH_{5-28}$, $PTH_{5-29}$, $PTH_{5-30}$, $PTH_{5-31}$, $PTH_{5-32}$, $PTH_{5-33}$, $PTH_{5-34}$, $PTH_{5-35}$, $PTH_{5-36}$, or $PTH_{5-37}$. Frequently, however, the non-whole PTH fragment is a peptide having an amino acid sequence from between $PTH_{3-84}$ and $PTH_{34-84}$.

In a further embodiment a multiple antigenic peptide (MAP) is provided, which MAP comprises a branched oligolysine core conjugated with a plurality of a PTH peptide as described herein. On occasion, the branched oligolysine core comprises 3, 7 or 15 lysine residues, also on occasion, the MAP comprises 4, 8 or 16 copies of the PTH peptide. The plurality of the PTH peptide comprises the same or different PTH peptides. In one aspect, the plurality of the PTH peptide is conjugated to the branched oligolysine core via a spacer. Frequently, the spacer is an amino acid residue. Multiple antigenic peptides comprise generally known technology. See, e.g., Adermann, K., et al., Innovations and Perspectives in Solid Phase Synthesis 429-32 (R. Epton, ed., Mayflower Worldwide 1994).

In another embodiment, the present disclosure provides a method for measuring a physiological level of whole parathyroid hormone in a mammalian sample, which method comprises: a) obtaining a sample from a mammal to be tested; b) contacting said sample with an isolated antibody that specifically binds to an N-terminal sequence of whole PTH and is capable of detecting said whole PTH at a physiological level in said mammalian sample, with a proviso that said isolated antibody avoids binding to a non-whole PTH fragment; and c) assessing a complex formed between said whole parathyroid hormone, if present in said sample, and said antibody, to measure physiological level of said whole parathyroid hormone in said mammalian sample. A variety of sample types may be utilized in accordance with the present methods including serum, plasma and blood samples. Frequently, the sample is a clinical sample and the mammal is a human. The non-whole PTH fragment may be any of the variety of non-whole PTH fragments as described herein.

In one aspect, the antibody specifically binds to an epitope comprised in $PTH_{1-6}$, $PTH_{1-8}$, $PTH_{1-9}$, $PTH_{1-12}$, or $PTH_{3-12}$, and/or the PTH peptide $PTH_{1-15}$. Frequently, the antibody specifically binds to a PTH epitope as discussed herein. On occasion, the binding between the antibody and the N-terminal sequence of whole PTH is dependent on the presence of amino acid residues 2-5 or 3-6 of the PTH.

Although a variety of assay types are contemplated, the present methods frequently assess the complex formed between the whole parathyroid hormone and the antibody via a sandwich or competitive assay format. On occasion, the complex is assessed in a homogeneous or a heterogeneous assay format. Also frequently, the complex is assessed by a format selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, plasmon resonance assay, chemiluminescence assay, lateral flow immunoassay, u-capture assay, inhibition assay and avidity assay. In a sandwich assay format, the antibody that specifically binds to an N-terminal sequence of whole PTH is used as a first antibody and antibody that is capable of binding to a portion of whole PTH other than the N-terminal sequence which binds to the first antibody is used as a second antibody. Either the first antibody or the second antibody is frequently attached to a surface and functions as a capture antibody. The attachment can be direct or indirect. In a preferred embodiment, the attachment is provided via a biotin-avidin (or streptavidin) linking pair.

In another aspect, the physiological level of whole parathyroid hormone is less than 4 pmol/L. Frequently, the physiological level of whole parathyroid hormone is from about 0.2 pmol/L to about 4 pmol/L. Also frequently, the physiological range of whole PTH ranges between about 2 pgm/ml to about 40 pgm/ml. On occasion, the physiological range of whole PTH ranges between about 7 pgm/ml to about 39 pgm/ml.

In a further embodiment, the present methods may be utilized to measure multiple PTH peptide components, such as a non-whole PTH peptide fragment level and/or a total PTH level, in addition to a whole PTH level. In such embodiments, the methods frequently further comprise comparing at least two parameters selected from the group consisting of the whole PTH level (wPTH), total PTH level, total PTH peptide fragment level, C-terminal PTH fragment level (cPTH), N-terminal PTH fragment level, and mid-terminal PTH fragment level (mPTH). The comparison of parameters is generally in the form of a ratio or proportion. Frequently, the results of said comparison are used to determine whether the mammal, often comprising a human patient, is afflicted with a bone turnover related disorder, or used to monitor bone disease related treatment. Also frequently, the present methods are used to determine or diagnose whether the mammal is afflicted with, or at risk for, adynamic bone disease or severe hyperparathyroidism. Frequently, the present methods are used for clinical management of renal disease subjects and subjects afflicted with osteoporosis, including dialysis patients. Also frequently, the present methods are used for diagnosing primary hyperparathyroidism. Moreover, the present methods are useful for clinical diagnosis and management of subjects having adynamic bone disease induced, in part, through the practice of inappropriate treatment protocols.

In preferred embodiments of the present comparison the comparison takes many forms. For example, the comparison can be in the form of a ratio or proportion between the whole PTH level versus the total PTH level (i.e., represented by the equation: wPTH/total PTH); between the whole PTH level versus the combined cPTH and mPTH fragment levels i.e., represented by the equation: wPTH/(cPTH+mPTH)); between the whole PTH level versus the combined cPTH and mPTH fragment levels, wherein double the whole PTH level is subtracted from the combined cPTH and mPTH fragment levels (i.e., represented by the equation: wPTH/((cPTH−wPTH)+(mPTH−wPTH))); between the whole PTH level versus the total of the combined cPTH and mPTH fragment levels subtracted by the whole PTH level (i.e., represented by the equation: wPTH/(cPTH+mPTH−wPTH)); between the whole PTH level versus the combined whole PTH level, cPTH and mPTH fragment levels (i.e., represented by the equation: wPTH/(wPTH+cPTH+mPTH)); between the whole PTH level versus the cPTH fragment level (i.e., represented by the equation: wPTH/cPTH); between the whole PTH level versus the mPTH fragment level (i.e., represented by the equation: wPTH/mPTH); between the whole PTH level versus the total PTH level minus the whole PTH level (i.e., represented by the equation: wPTH/(total PTH−wPTH)); or other combinations of the disclosed parameters, including, without limitation, the inverse of each comparison. Moreover, without limitation, in one aspect, the value obtained from determining the total PTH level and subtracting this level from the whole PTH level yields the total PTH fragment level in a sample/subject. The cutoff ranges for each of these comparisons as they are associated with a particular bone turnover, treatment, disease or disorder vary as provided herein (see e.g., Table 2 and accompanying discussion).

Frequently in the present methods the sample is contacted with one or more isolated antibodies, and wherein each of said one or more isolated antibodies specifically binds one or more PTH peptide fragments selected from the group consisting of: $PTH_{39-84}$, $PTH_{1-34}$, $PTH_{43-68}$, $PTH_{7-84}$, $PTH_{39-68}$, $PTH_{53-84}$, $PTH_{65-84}$, $PTH_{44-68}$, $PTH_{19-84}$, $PTH_{23-84}$, $PTH_{1-38}$, $PTH_{1-48}$, $PTH_{1-58}$, $PTH_{1-68}$, and $PTH_{1-78}$.

The present methods of measuring multiple PTH components provide a variety of uses. For example, such methods are used for differentiating between a person having substantially normal parathyroid function and having hyperparathyroidism, e.g., primary hyperparathyroidism; monitoring parathyroid related bone disease and treatment; monitoring effects of therapeutic treatment for hyperparathyroidism; diagnosing parathyroid related bone disease; clinical management of renal disease subjects and renal disease related treatments and subjects afflicted with osteoporosis and osteoporosis related treatments.

The present disclosure further provides kits for carrying out the presently described methods and utilizing the peptides and antibodies as described herein. In one embodiment, a kit for measuring a physiological level of whole parathyroid hormone in a mammalian sample, which kit comprises, in a container, an isolated antibody that specifically binds to an N-terminal sequence of whole parathyroid hormone (PTH) and is capable of detecting said whole PTH at a physiological level in a mammalian sample, with a proviso that said isolated antibody avoids binding to a non-whole PTH fragment.

In another embodiment, the present disclosure further provides kits for producing an antibody to a parathyroid hormone (PTH) or a PTH peptide, which kits comprise: a) an isolated PTH peptide; b) means for introducing said isolated PTH peptide to a mammal in an amount sufficient to produce an antibody to said PTH peptide; and c) means for recovering said antibody from said mammal. In further embodiment, a kit for producing an antibody to a parathyroid hormone (PTH) or a PTH peptide is provided which comprises: a) a MAP; b) a means for introducing said MAP to a mammal in an amount sufficient to produce an antibody to a PTH peptide comprised in said MAP; and b) a means for recovering said antibody from said mammal. In a still further embodiment, a kit is provided for producing an antibody to a parathyroid hormone (PTH) or a PTH peptide, which kit comprises: a) a PTH protein or peptide from between $PTH_{1-34}$ and $PTH_{1-84}$; b) means for introducing said PTH protein or peptide from between $PTH_{1-34}$ and $PTH_{1-84}$ to a mammal in an amount sufficient to produce an antibody to said PTH protein or peptide; c) means for recovering said antibody from said mammal; and c) another specific PTH peptide.

An isolated PTH peptide in such kits can be any of the variety of PTH peptides as described herein. Frequently, the PTH peptide are conjugated to a carrier to enhance the PTH peptide's immunogenecity, e.g., a carrier protein, which may together form a fusion protein. For example, such peptide is selected from the group consisting of $PTH_{1-11}$, $PTH_{1-13}$, $PTH_{1-14}$, $PTH_{1-15}$, $PTH_{1-16}$, $PTH_{1-17}$, $PTH_{1-18}$, $PTH_{1-19}$, $PTH_{1-20}$, $PTH_{1-21}$, $PTH_{1-22}$, $PTH_{1-23}$, $PTH_{1-24}$, $PTH_{1-25}$, $PTH_{1-26}$, $PTH_{1-27}$, $PTH_{1-28}$, $PTH_{1-29}$, $PTH_{1-30}$, $PTH_{1-30}$, $PTH_{1-31}$, $PTH_{1-32}$, $PTH_{1-33}$, $PTH_{1-34}$, $PTH_{1-35}$, $PTH_{1-36}$, $PTH_{2-5}$, $PTH_{2-6}$, $PTH_{2-8}$, $PTH_{2-9}$, $PTH_{2-10}$, $PTH_{2-11}$, $PTH_{2-12}$, $PTH_{2-13}$, $PTH_{2-14}$, $PTH_{2-15}$, $PTH_{2-16}$, $PTH_{2-17}$, $PTH_{2-18}$, $PTH_{2-19}$, $PTH_{2-20}$, $PTH_{2-21}$, $PTH_{2-22}$, $PTH_{2-23}$, $PTH_{2-24}$, $PTH_{2-25}$, $PTH_{2-26}$, $PTH_{2-27}$, $PTH_{2-28}$, $PTH_{2-29}$, $PTH_{2-30}$, $PTH_{2-31}$, $PTH_{2-32}$, $PTH_{2-33}$, $PTH_{2-34}$, $PTH_{2-35}$, $PTH_{2-36}$, $PTH_{3-6}$, $PTH_{3-7}$, $PTH_{3-9}$, $PTH_{3-10}$, $PTH_{3-11}$, $PTH_{3-12}$, $PTH_{3-13}$, $PTH_{3-14}$, $PTH_{3-15}$, $PTH_{3-16}$, $PTH_{3-17}$, $PTH_{3-18}$, $PTH_{3-19}$, $PTH_{3-20}$, $PTH_{3-21}$, $PTH_{3-22}$, $PTH_{3-23}$, $PTH_{3-24}$, $PTH_{3-25}$, $PTH_{3-26}$, $PTH_{3-27}$, $PTH_{3-28}$, $PTH_{3-29}$, $PTH_{3-30}$, $PTH_{3-31}$, $PTH_{3-32}$, $PTH_{3-33}$, $PTH_{3-34}$, $PTH_{3-35}$, $PTH_{3-36}$, $PTH_{4-7}$, $PTH_{4-8}$, $PTH_{4-9}$, $PTH_{4-10}$, $PTH_{4-11}$, $PTH_{4-13}$, $PTH_{4-14}$, $PTH_{4-15}$, $PTH_{4-16}$, $PTH_{4-17}$, $PTH_{4-18}$, $PTH_{4-19}$, $PTH_{4-20}$, $PTH_{4-21}$, $PTH_{4-22}$, $PTH_{4-23}$, $PTH_{4-24}$, $PTH_{4-25}$, $PTH_{4-26}$, $PTH_{4-27}$, $PTH_{4-28}$, $PTH_{4-29}$, $PTH_{4-30}$, $PTH_{4-31}$, $PTH_{4-32}$, $PTH_{4-33}$, $PTH_{4-34}$, $PTH_{4-35}$, $PTH_{4-36}$, $PTH_{5-8}$, $PTH_{5-9}$, $PTH_{5-11}$, $PTH_{5-12}$, $PTH_{5-13}$, $PTH_{5-14}$, $PTH_{5-15}$, $PTH_{5-16}$, $PTH_{5-17}$, $PTH_{5-18}$, $PTH_{5-19}$, $PTH_{5-20}$, $PTH_{5-21}$, $PTH_{5-22}$, $PTH_{5-23}$, $PTH_{5-24}$, $PTH_{5-25}$, $PTH_{5-26}$, $PTH_{5-27}$, $PTH_{5-28}$, $PTH_{5-29}$, $PTH_{5-30}$, $PTH_{5-31}$, $PTH_{5-32}$, $PTH_{5-33}$, $PTH_{5-34}$, $PTH_{5-35}$, $PTH_{5-36}$, and $PTH_{5-37}$.

The presently contemplated kits may also provide an immunogen comprising a PTH peptide as described herein, together with an immune response potentiator. On occasion, the immune response potentiator is selected from the group consisting of Bacille Calmette-Guerin (BCG), *Corynebacterium Parvum, Brucella abortus* extract, glucan, levamisole, tilorone, an enzyme and a non-virulent virus.

The present disclosure further provides methods for producing an antibody to a parathyroid hormone (PTH) or a PTH peptide. In one embodiment, such method comprises: a) introducing an isolated PTH peptide to a mammal in an amount sufficient to produce an antibody to said PTH peptide; and b) recovering said antibody from said mammal. Another frequent method for producing an antibody to a parathyroid hormone (PTH) or a PTH peptide comprises: a) introducing a MAP to a mammal in an amount sufficient to produce an antibody to a PTH peptide comprised in said MAP; and b) recovering said antibody from said mammal. In one aspect, the present disclosure provides antibodies to a PTH or a PTH peptide produced by these methods. In a related embodiment, a method is provided for producing an antibody to a parathyroid hormone (PTH) or a PTH peptide, which method comprises: a) introducing a PTH protein or peptide from between $PTH_{1-34}$ and $PTH_{1-84}$ to a mammal in an amount sufficient to produce an antibody to said PTH protein or peptide; b) recovering said antibody from said mammal; and c) affinity purifying a PTH antibody that specifically binds to an epitope comprised in a PTH peptide using said PTH peptide. In a further embodiment, the present disclosure provides an antibody to a PTH or a PTH peptide produced by such methods.

V. BRIEF DESCRIPTION OF THE DRAWINGS

Figure 14:
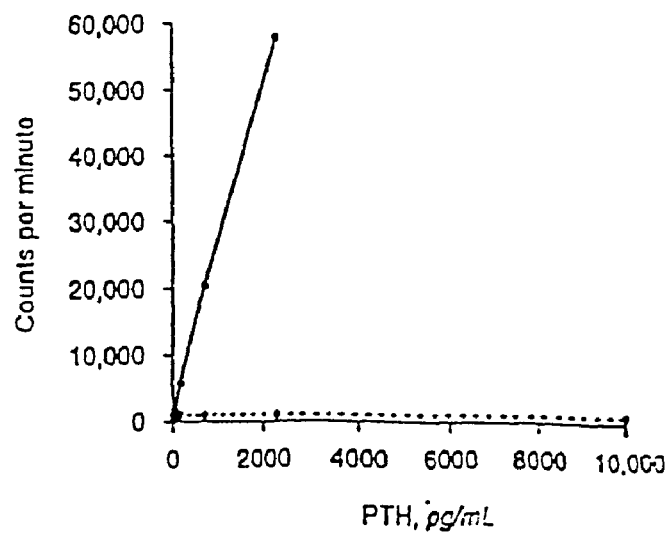

FIG. 14 illustrates comparison of the recognition of hPTH 1-84 and hPTH 7-84 by the Whole PTH assay. Unlike the Nichols I-PTH assay, the Whole PTH assay does discriminate between hPTH 1-84 (solid line) and hPTH 7-84 (dashed line). Concentrations of hPTH 7-84 as high as 10,000 pg were undetectable.

Figure 15:
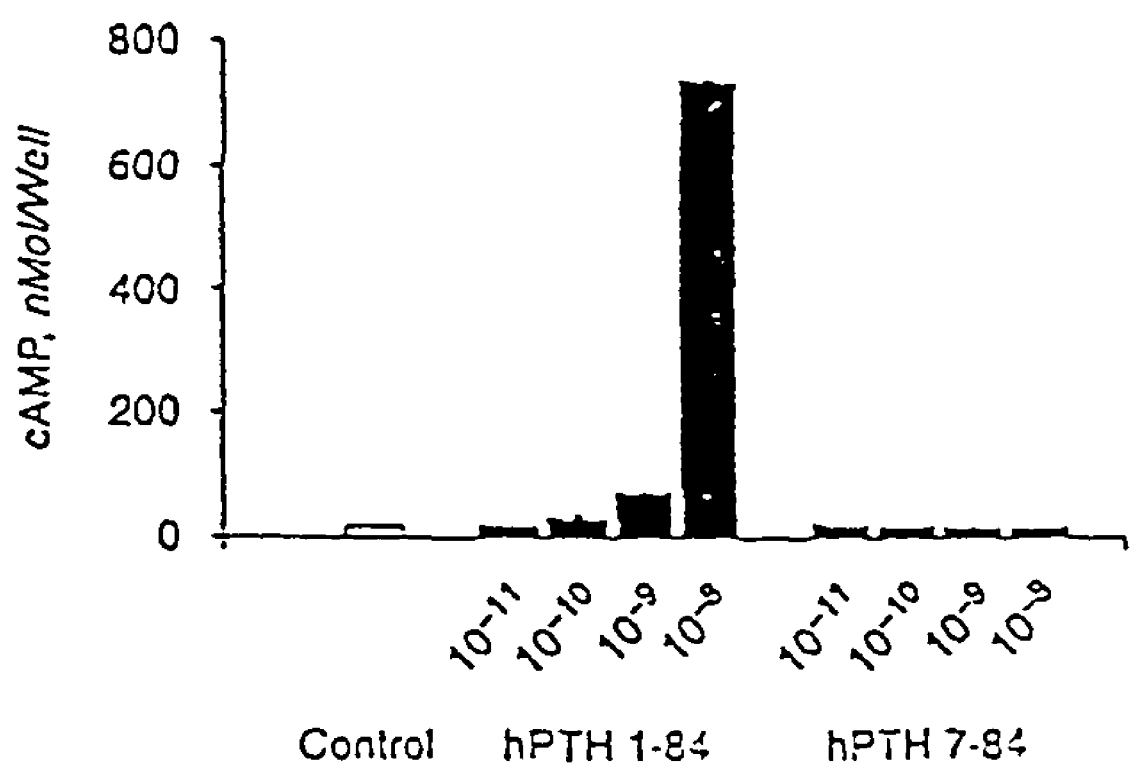

FIG. 15 illustrates comparison of the effect of hPTH 1-84 or hPTH 7-84 on cAMP production in ROS 17.2 cells. Unlike hPTH 7-84, hPTH 1-84 increased cAMP production in a dose-dependent manner. cAMP increased from $18.1 \pm 1.2$ to $738 \pm 4.1$ nmol/well after treatment with $10^{-8}$ mol/L hPTH 1-84. The same concentration of hPTH 7-84 had no effect.

Figure 16:
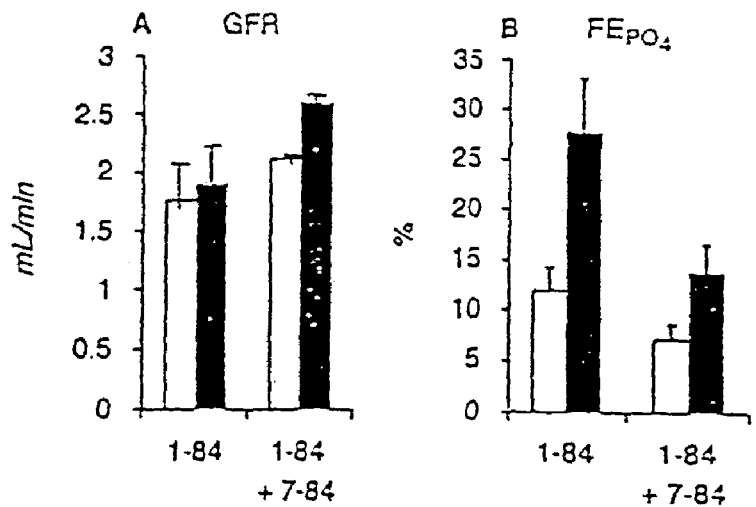

FIG. 16 illustrates comparison of the effects of hPTH 1-84 or hPTH 1-84 plus hPTH 7-84 on (A) glomerular filtration rate (GFR) and (B) fractional excretion of phosphorus ($FE_{po4}$). Control and treatment periods are denoted by open and closed bars, respectively. The phosphaturia induced by hPTH 1-84 was decreased by 50.2% ($P<0.05$) when animals were treated simultaneously with 7-84 PTH, despite a significant increase in GFR ($p<0.005$).

Figure 17:
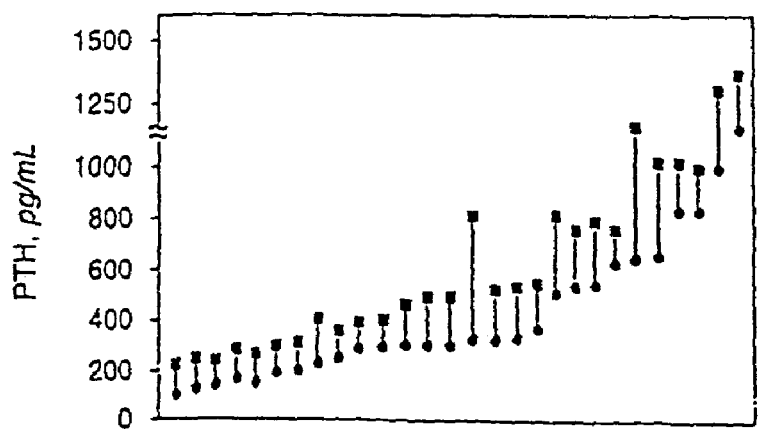

FIG. 17 illustrates comparison of PTH values in plasma from uremic patients using the Nichols "intact" PTH assay (■) versus the Whole PTH assay (●). Plasma PTH values are uniformly higher when measured with the Nichols "intact" PTH assay than with the Whole PTH assay. The median PTH values were 523 vs. 344 pg/mL, respectively ($P<0.001$).

Figure 18:
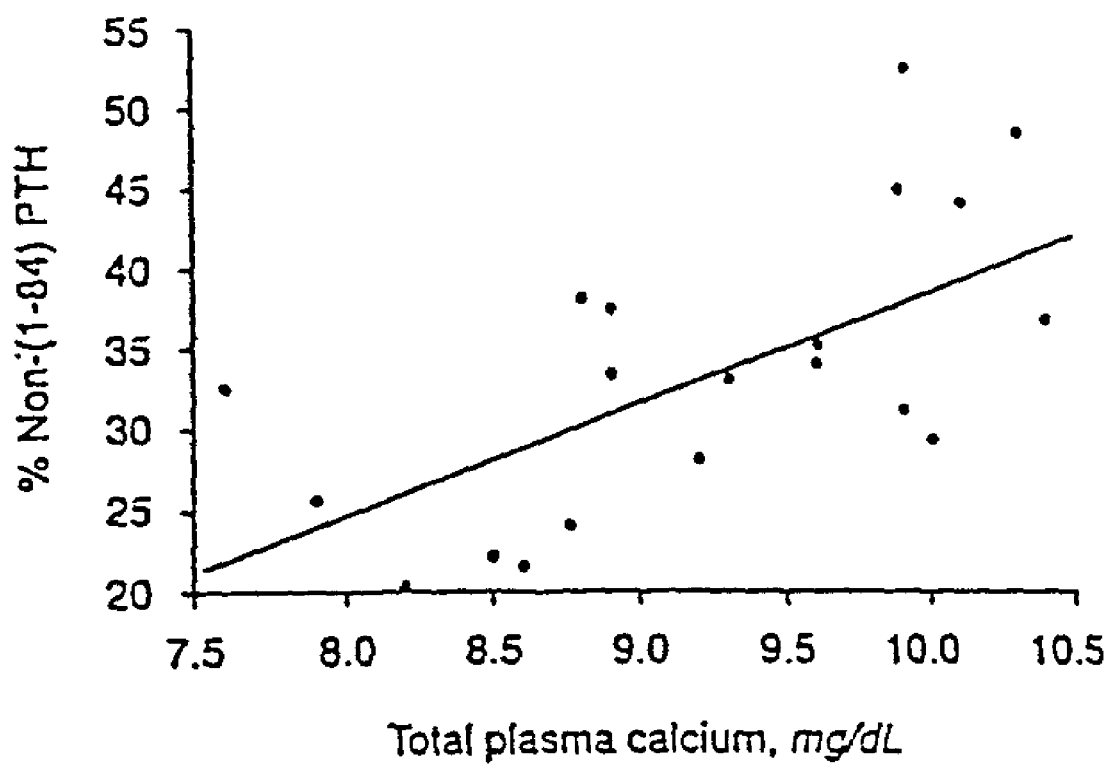

FIG. 18 illustrates effects of plasma calcium on PTH degradation in dialysis patients. The percentage of non-(1-84) PTH fragment (likely hPTH 7-84) correlates positively with plasma calcium ($P<0.02$) ($r=0.638$; $P=0.0025$; $N=20$).

Figure 19:
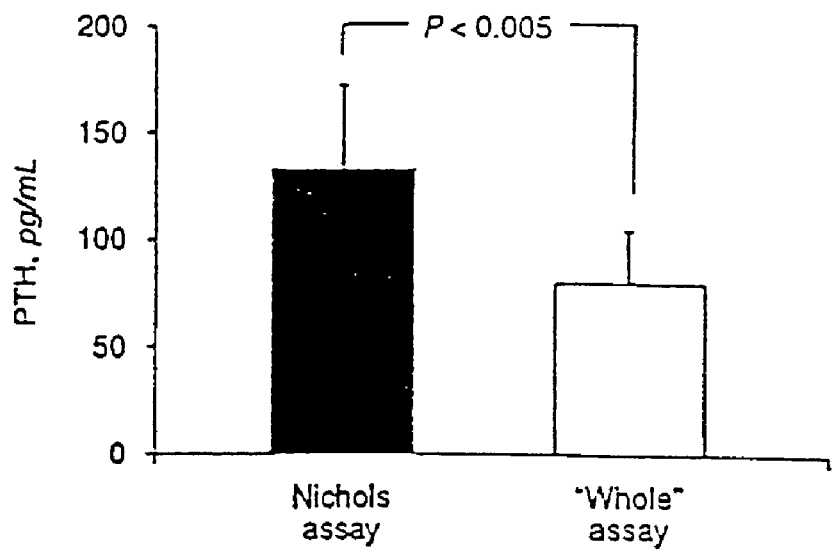

FIG. 19 illustrates comparison of plasma PTH levels in renal transplant patients using Nichols I-PTH and Whole PTH assays. PTH values are higher when measured with the Nichols I-PTH assay ($P>0.005$).

Figure 20:
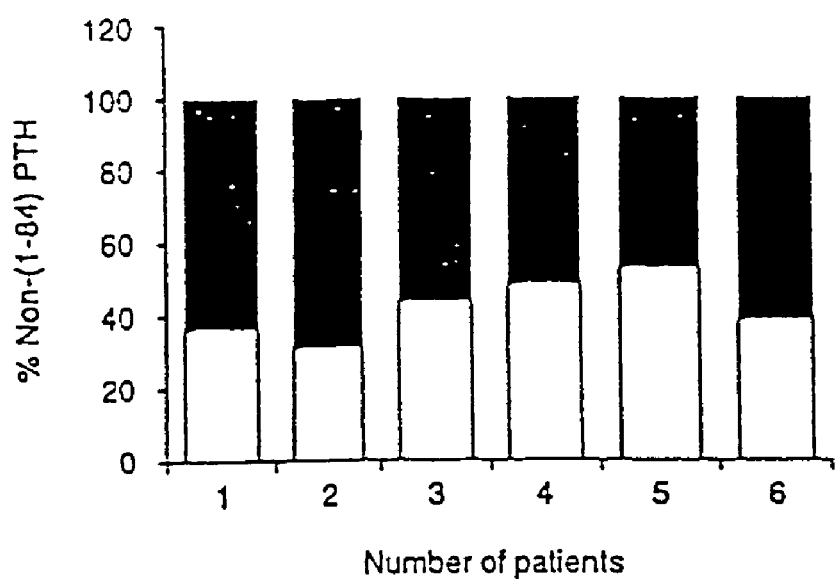

FIG. 20 illustrates intracellular PTH content on parathyroid glands from uremic patients. The $41.8 \pm 3.2\%$ of the total PTH, measured by the I-Nichols assay (expressed as 100%), represents the non-(1-84) PTH fragment "likely" hPTH 7-84 (□). the 1-84 PTH molecule was measured with the Whole PTH assay (■).

VI. DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, patent applications (published or unpublished), and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "antibody" is used in the broadest sense. Therefore, an "antibody" can be naturally occurring or man-made such as monoclonal antibodies produced by conventional hybridoma technology and/or a functional fragment thereof. Antibodies of the present invention comprise monoclonal and polyclonal antibodies as well as fragments containing the antigen-binding domain and/or one or more complementarity determining regions of these antibodies.

As used herein, "monoclonal antibody" refers to an antibody obtained from a population of substantially homogeneous antibodies, i.e., the antibodies comprising the population are identical except for possible naturally occurring mutations that are present in minor amounts. As used herein, a "monoclonal antibody" further refers to functional fragments of monoclonal antibodies.

As used herein, "mammal" refers to any of the mammalian class of species. Frequently, the term "mammal," as used herein, refers to humans, human subjects or human patients.

As used herein, "whole parathyroid hormone (PTH)" or "wPTH" refers to the complete molecule of PTH. This term is not species-specific unless otherwise designated. For purposes herein, the name "parathyroid hormone (PTH)" is used herein, although all other names are contemplated. It is intended to encompass whole PTH with conservative amino acid substitutions that do not substantially alter its biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., MOLECULAR BIOLOGY OF THE GENE, 4th Edition, 1987, The Bejamin/Cummings Pub. Co., p. 224).

As used herein, "parathyroid hormone (PTH) agonist," "cyclase activating PTH" or "CAP" refers to the complete molecule of PTH or a fragment, derivative or analog thereof that stimulates osteoclasts formation and bone turnover to increase blood calcium levels. PTH agonist further refers to peptides which have PTH agonist properties. Other names of PTH include parathormone and parathyrin. For purposes herein, the name "parathyroid hormone (PTH)" is used herein, although all other names are contemplated. It is intended to encompass PTH agonist with conservative amino acid substitutions that do not substantially alter its biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., MOLECULAR BIOLOGY OF THE GENE, 4th Edition, 1987, The Bejamin/Cummings Pub. co., p. 224). PTH agonist assay values may be obtained by measuring a sample with a Scantibodies Whole PTH Assay or a Scantibodies CAP Assay or a $3^{rd}$ generation PTH Assay or a Nichols BioIntact PTH assay or an Immutopics Human Bioactive PTH assay.

As used herein, the term "total PTH" refers to a total accounting of whole PTH levels in addition to PTH fragment levels. Moreover, this term is not species-specific unless otherwise designated.

As used herein, the term "PIN" refers to PTH fragments that have PTH antagonistic or inhibiting properties. Therefore, although occasionally of concurrent scope, a reference to PTH fragments, as provided herein, is not intended to be limited to PIN.

As used herein, a "PTH fragment" is a PTH peptide that comprises a non-whole contiguous portion of an entire PTH protein. A reference to a PTH fragment as herein includes C-terminal, mid-terminal fragments and PIN, unless otherwise indicated. Moreover, this term is not species-specific unless otherwise designated.

As used herein, "treatment" means any manner in which the symptoms of a condition, disorder or disease are ameliorated or otherwise beneficially altered. Treatment also encompasses any pharmaceutical use of the compositions herein.

As used herein, "disease or disorder" refers to a pathological condition in an organism resulting from, e.g., infection or genetic defect, and characterized by identifiable symptoms.

As used herein, "high bone turnover" refers to the bone turnover rate as being above a normal bone turnover rate in a subject and is one of the symptoms manifested in subjects having hyperparathyroidism. While not bound by theory, a subject afflicted with severe hyperparathyroidism has a higher bone turnover rate than the same subject afflicted with mild hyperparathoidism, however, both having a high bone turnover rate as compared with a normal subject and a subject afflicted with adynamic bone disease.

As used herein, the term "subject" is not limited to a specific species or sample type. For example, the term "subject" may refer to a patient, and frequently a human patient. However, this term is not limited to humans and thus encompasses a variety of mammalian species.

As used herein, "afflicted" as it relates to a disease or disorder refers to a subject having or directly affected by the designated disease or disorder.

As used herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein the term "avoids binding" refers to the specificity of particular antibodies or antibody fragments. Antibodies or antibody fragments that avoid binding a particular moiety generally contain a specificity such that a large percentage of the particular moiety would not be bound by such antibodies or antibody fragments. This percentage generally lies within the acceptable cross reactivity percentage with interfering moieties of assays utilizing antibodies directed to detecting a specific target. Frequently, antibodies or antibody fragments of the present disclosure avoid binding greater than about 90% of an interfering moiety, although higher percentages are clearly contemplated and preferred. For example, antibodies or antibody fragments of the present disclosure avoid binding about 91%, about 92%, about 93%, about 94%, about 95%, about 96%, about 97%, about 98%, about 99%, and about 99% or more of an interfering moiety. Less occasionally, antibodies or antibody fragments of the present disclosure avoid binding greater than about 70%, or greater than about 75%, or greater than about 80%, or greater than about 85% of an interfering moiety. Although not bound by theory, as contemplated herein, an interfering moiety may comprise a non-whole PTH fragment.

As used herein the term "physiological level of whole PTH" refers generally to the average concentration of whole PTH present in a mammal, e.g., a human, expressed in pmol/L, or another suitable measurement unit (e.g., pgm/ml). See, e.g., Woodhead, J. S., Clin. Biochem. 23, 17 (1990). In one aspect, the physiological range of whole PTH ranges between about 0.2 pmol/L to about 4 pmol/L, or about 2 pgm/ml to about 40 pgm/ml. On occasion, the physiological range of whole PTH can range between about 7 pgm/ml to about 39 pgm/ml. Although specific ranges are described herein as representative of a physiological range, one of skill in the art would understand that the physiological level of whole PTH may lie outside of the presently disclosed ranges in certain subjects. Nevertheless, the compositions and methods provided herein are useful to detect discreet concentrations of whole PTH and have sensitivities within the physiological range as provided herein.

As used herein, the term "N-terminal" refers to the amino terminus of a PTH polypeptide having a free amino group. With reference to a PTH fragment, an N-terminal PTH fragment refers to a non-whole contiguous portion of PTH having an intact N-terminal. An "intact N-terminal" as used herein refers to PTH or a PTH fragment having an intact 1st position of $PTH_{1-84}$. This first position is also referred to herein as an "original N-terminus" or an "original N-terminal."

As used herein, the term "C-terminal" refers to the carboxyl terminus of a PTH polypeptide having a free carboxyl group. With reference to a PTH fragment, a C-terminal PTH fragment refers to a non-whole contiguous portion of PTH having an intact C-terminal. An "intact C-terminal" as used herein refers to PTH or a PTH fragment having an intact 84th position of $PTH_{1-84}$. This 84th position is also referred to herein as an "original C-terminus" or an "original C-terminal."

As used herein, the term "mid-terminal PTH fragment" refers to a non-whole contiguous portion of PTH having neither an intact N-terminal nor an intact C-terminal. These types of PTH fragments may also be referred to herein as "mid-terminus fragments."

As used herein, the term "specifically binds" refers to the specificity of an antibody such that it preferentially binds to a defined target. Recognition by an antibody of a particular target in the presence of other potential targets is one characteristic of such binding. Specific binding of the presently contemplated antibodies to particular PTH targets is measured through known methods utilizing the tools provided herein.

As used herein, "stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Current Protocols in Molecular Biology (Ausubel et al. eds., Wiley Interscience Publishers, 1995); Molecular Cloning: A Laboratory Manual (J. Sambrook, E. Fritsch, T. Maniatis eds., Cold Spring Harbor Laboratory Press, 2d ed. 1989); Wood et al., *Proc. Natl. Acad. Sci. USA*, 82:1585-1588 (1985).

As used herein the term "isolated" refers to material removed from its original environment, and is altered from its natural state. For example, an isolated polypeptide could be coupled to a carrier, and still be "isolated" because that polypeptide is not in its original environment.

The present disclosure encompasses antigens, antibodies and methods of producing antibodies that have a particular specificity to target proteins and/or peptides which contain a specific amino acid residue or multiple amino acid residues, in a series or otherwise. The specific amino acid residue(s) may be located in the N-terminal region of a proteins or peptide or in the C-terminal region. Moreover the specific amino acid residue(s) may be located in a region between the N-terminal and C-terminal regions of a protein or peptide. Occasionally, when there is more than one specific amino acid residue, such residues may be dispersed in any one or more of the N-terminal, C-terminal, between these two regions, and/or in all of these regions.

Figure 1:
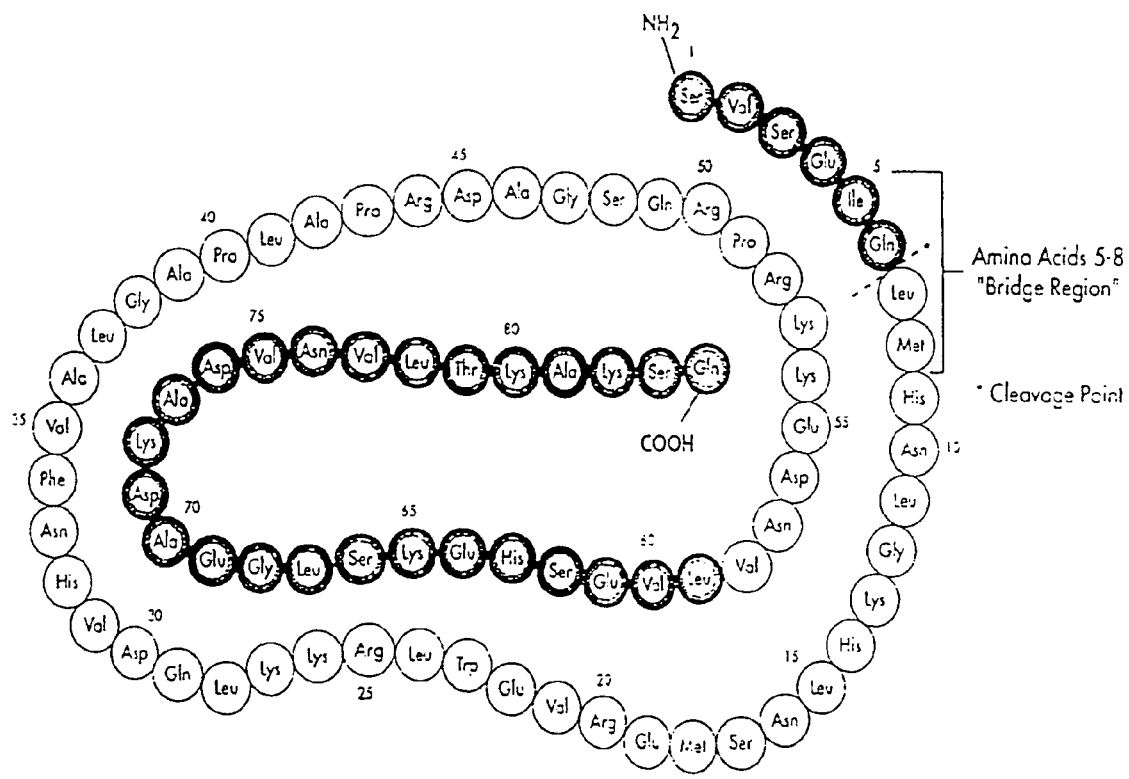
FIG. 1 is a diagrammatic view of whole human PTH (SEQ ID NO: 1).

In disclosing the present invention, one should remember that there are a number of closely analogous, species dependent forms of PTH. The amino acid sequence of hPTH is shown in FIG. 1. However, for rat PTH, mouse PTH, bovine PTH, canine PTH, horse PTH or porcine PTH, for example, one finds the substitutions at some of the amino acids in the hPTH sequence. For the purposes of the present invention, one can use interchangeably antibodies or antibody fragments to forms of these PTHs, although it is preferred to use an antibody with specificity for PTH having a sequence matching the species in which the PTH measurements are made.

B. Parathyroid Hormone Fragments

In general, a PTH fragment of the present invention comprises a non-whole contiguous portion of PTH having an amino acid sequence as set forth in SEQ ID NOs: 1, 2, 3, 4, 5, 6, and/or 7 ($PTH_{1-84}$), or a nucleic acid encoding said portion of PTH. A PTH fragment may have the following characteristics: a) the N-terminal amino acid residue of said PTH fragment starts at any position spanning position 1 through position 80 of said $PTH_{1-84}$; b) the C-terminal amino acid residue of said PTH fragment ends at any position spanning position 4 through position 84 of said $PTH_{1-84}$; and c) said PTH fragment has a minimal length of three amino acid residues. Preferably, the PTH fragment is in the form of a pharmaceutical composition.

PTH fragments of the present invention are organized into three categories: N-terminal, C-terminal, and mid-terminal PTH fragments. As further described herein, N-terminal fragments comprise a non-whole contiguous portion of PTH having an intact N-terminus, but not an intact original C-terminus. As also described herein, C-terminal fragments comprise a non-whole contiguous portion of PTH having an intact C-terminus, but not an intact original N-terminus. Moreover, as further described herein, mid-terminal fragments comprise a non-whole contiguous portion of PTH having neither an intact original C-terminus, nor intact original N-terminus. All mammalian sources/sequences of PTH are contemplated.

In one embodiment, PTH fragments comprise a subset of cyclase inactive PTH. However, in light of the present description, a variety of other PTH fragments are contemplated, ascertainable and useful in the present compositions, kits and methods. Importantly, $PTH_{7-84}$ represents a member of the group of PTH fragments currently contemplated. The present disclosure further contemplates large inactive PTH fragments in the description of PTH fragments.

In one embodiment, the N-terminal amino acid residue of the PTH fragment starts at any defined position spanning position 2 through position 70 of said $PTH_{1-84}$. The C-terminal amino acid residue of said PTH fragment ends at any defined position spanning position 35 through position 84 of said $PTH_{1-84}$. Therefore, for example, fragments ranging from $PTH_{2-84}$ to $PTH_{34-84}$ to $PTH_{70-84}$ are included as C-terminal fragments. Mid-terminal PTH fragments are also contemplated, for example, ranging within $PTH_{39-68}$ or $PTH_{44-68}$. For example, mid-terminal PTH fragments having their N-terminal beginning around position 44 of said $PTH_{1-84}$ and their C-terminal ending around position 68 of said $PTH_{1-84}$ are included in the present description. Without being bound by theory, a mid-terminal PTH fragment does not include position 1, nor position 84 of said $PTH_{1-84}$, but rather falls within these positions.

In a specific embodiment, the PTH fragment is a protein or a peptide, or a nucleic acid encoding said protein or peptide, selected from the group consisting of $PTH_{2-84}$, $PTH_{3-84}$, $PTH_{4-84}$, $PTH_{5-84}$, $PTH_{6-84}$, $PTH_{7-84}$, $PTH_{8-84}$, $PTH_{9-84}$, $PTH_{10-84}$, $PTH_{11-84}$, $PTH_{12-84}$, $PTH_{13-84}$, $PTH_{14-84}$, $PTH_{15-84}$, $PTH_{16-84}$, $PTH_{17-84}$, $PTH_{18-84}$, $PTH_{19-84}$, $PTH_{20-84}$, $PTH_{21-84}$, $PTH_{22-84}$, $PTH_{23-84}$, $PTH_{24-84}$, $PTH_{25-84}$, $PTH_{26-84}$, $PTH_{27-84}$, $PTH_{28-84}$, $PTH_{29-84}$, $PTH_{30-84}$, $PTH_{31-84}$, $PTH_{32-84}$, and $PTH_{33-84}$. In another specific embodiment, the PTH fragment is a protein or a peptide, or a nucleic acid encoding said protein or peptide, selected from the group consisting of $PTH_{7-69}$, $PTH_{7-70}$, $PTH_{7-71}$, $PTH_{1-72}$, $PTH_{1-73}$, $PTH_{7-74}$, $PTH_{7-75}$, $PTH_{7-76}$, $PTH_{7-77}$, $PTH_{7-78}$, $PTH_{7-79}$, $PTH_{7-80}$, $PTH_{7-81}$, $PTH_{7-82}$, $PTH_{7-83}$ and $PTH_{7-84}$.

In another embodiment, the PTH fragment is a protein or a peptide, or a nucleic acid encoding said protein or peptide, selected from the group consisting of $PTH_{34-84}$, $PTH_{35-84}$, $PTH_{36-84}$, $PTH_{37-84}$, $PTH_{38-84}$, $PTH_{39-84}$, $PTH_{40-84}$, $PTH_{41-84}$, $PTH_{42-84}$, $PTH_{43-84}$, $PTH_{44-84}$, $PTH_{45-84}$, $PTH_{46-84}$, $PTH_{47-84}$, $PTH_{48-84}$, $PTH_{49-84}$, $PTH_{50-84}$, $PTH_{51-84}$, $PTH_{52-84}$, $PTH_{53-84}$, $PTH_{54-84}$, $PTH_{55-84}$, $PTH_{56-84}$, $PTH_{57-84}$, $PTH_{58-84}$, $PTH_{59-84}$, $PTH_{60-84}$, $PTH_{61-84}$, $PTH_{62-84}$, $PTH_{63-84}$, $PTH_{64-84}$, $PTH_{65-84}$, $PTH_{66-84}$, $PTH_{67-84}$, $PTH_{68-84}$, $PTH_{69-84}$, and $PTH_{70-84}$.

In a further embodiment, the PTH fragment is a protein or a peptide, or a nucleic acid encoding said protein or peptide, selected from the group consisting of $PTH_{7-60}$, $PTH_{8-60}$, $PTH_{9-60}$, $PTH_{10-60}$, $PTH_{11-60}$, $PTH_{12-60}$, $PTH_{13-60}$, $PTH_{14-60}$, $PTH_{15-60}$, $PTH_{16-60}$, $PTH_{17-60}$, $PTH_{18-60}$, $PTH_{19-60}$, $PTH_{20-60}$, $PTH_{21-60}$, $PTH_{22-60}$, $PTH_{23-60}$, $PTH_{24-60}$, $PTH_{25-60}$, $PTH_{26-60}$, $PTH_{27-60}$, $PTH_{28-60}$, $PTH_{29-60}$, $PTH_{30-60}$, $PTH_{31-60}$, $PTH_{32-60}$, $PTH_{33-60}$, $PTH_{34-60}$, $PTH_{35-60}$, $PTH_{36-60}$, $PTH_{37-60}$, and $PTH_{38-60}$, $PTH_{39-60}$, $PTH_{40-60}$, $PTH_{41-60}$, $PTH_{42-60}$, $PTH_{43-60}$, $PTH_{44-59}$, $PTH_{44-60}$, $PTH_{45-60}$, $PTH_{46-60}$, $PTH_{47-60}$, and $PTH_{48-60}$, and other mid-terminal PTH fragments as described herein. In another specific embodiment, the PTH fragment is a protein or a peptide, or a nucleic acid encoding said protein or peptide, selected from the group consisting of $PTH_{13-34}$, $PTH_{7-53}$, $PTH_{8-53}$, $PTH_{9-53}$, $PTH_{10-53}$, $PTH_{11-53}$, $PTH_{12-53}$, $PTH_{13-53}$, $PTH_{14-53}$, $PTH_{15-53}$, $PTH_{16-53}$, $PTH_{17-53}$, $PTH_{18-53}$, $PTH_{19-53}$, $PTH_{20-53}$, $PTH_{21-53}$, $PTH_{22-53}$, $PTH_{23-53}$, $PTH_{24-53}$, $PTH_{25-53}$, $PTH_{26-53}$, $PTH_{27-53}$, $PTH_{28-53}$, $PTH_{29-53}$, $PTH_{30-53}$, $PTH_{31-53}$, $PTH_{32-53}$, $PTH_{33-53}$, $PTH_{34-53}$, $PTH_{35-53}$, $PTH_{6-53}$, $PTH_{37-53}$, and $PTH_{38-53}$, and other mid-terminal PTH fragments as described herein.

In another preferred embodiment, a PTH fragment comprises, or an antibody specifically binds, a PTH peptide fragment selected from the group consisting of: $PTH_{39-84}$, $PTH_{1-34}$, $PTH_{43-68}$, $PTH_{7-84}$, $PTH_{39-68}$, $PTH_{53-84}$, $PTH_{65-84}$, $PTH_{44-68}$, $PTH_{19-84}$, $PTH_{23-84}$, $PTH_{1-68}$, or a combination of two or more from this group. This group may further comprise a PTH peptide fragment having an N-terminus starting between position 39 to 65 of $PTH_{1-84}$, and having a C-terminal position ending at position 84 of $PTH_{1-84}$. In a particularly preferred embodiment, a PTH peptide fragment comprises a PTH fragment present and detectable in nature.

In another embodiment, the PTH fragment is a protein or a peptide, or a nucleic acid encoding said protein or peptide having an intact N-terminus, for example, without limitation, $PTH_{1-38}$, $PTH_{1-48}$, $PTH_{1-58}$, $PTH_{1-68}$, $PTH_{1-78}$, amongst other intact N-terminal PTH fragments.

The PTH fragment can have any suitable length and may have PTH agonizing or antagonizing activity, although PTH agonizing or antagonizing activity is not required of the present PTH fragments. For example, the PTH fragment can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82 or 83 amino acid residues.

C. PTH Ratios

Whole PTH and PTH Fragments

An important discovery leading to the present invention is that adynamic bone loses its capacity to buffer calcium and phosphate as the bones are shut down. In subjects afflicted with such conditions, they are unable to effectively buffer calcium as it enters their bodies through their diet. This calcium enters the blood stream and is thereafter shuttled to the soft tissues. The parathyroid gland is particularly subject to, and detrimentally affected by, this influx of calcium and thereby produces PTH fragments rather than, or in addition to, the active form of PTH. See, e.g., Mayer G P, et al., *Endocrinology* 104: 1778-1784 (1979); D'Amour P, et al., *J. Clin. Endocrinol. Metab.* 74: 525-532 (1992); D'Amour P, et al., *J. Bone Miner. Res.* 11: 1075-1085 (1996); Cardinal, H., et al., *J. Clin. Endocrinol. Metab.* 83: 3839-44 (1998). Accordingly, in subjects with adynamic bone, the concentration and production of PTH fragments is increased. In light of this and other related information, the measurement of PTH fragment levels, and particularly in conjunction with the measurement of whole PTH, can be used effectively to differentiate subjects having adynamic bone versus those having normal bone and high bone turnover rates.

The present disclosure includes these findings in the presentation of peptides, antibodies, methods and kits for the measurement of PTH levels. In one preferred embodiment, the present methods utilize a ratio of whole PTH to total PTH, wherein the total PTH level comprises whole PTH plus PTH fragments in addition to $PTH_{7-84}$, such as other PTH fragments described herein (i.e., whole PTH/total PTH ratio).

This ratio contains an increased total PTH concentration as compared with a PTH ratio that comprises a total PTH level reflecting measurement of whole PTH plus PTH fragments that specifically bind to an antibody generated from $PTH_{7-84}$ peptide. Accordingly, the CAP/PTH fragment ratio according is generally lower than the CAP/(CAP+$PTH_{7-84}$) ratio. Until presently, recognition of the predictive and therapeutic benefits of PTH ratios have been unrecognized. See, e.g., Martine-Esther Cohen Solal, et al., *J. Clin. Endocrinol. Metab.* 73: 516-524 (1991) (concluding that the measurement of whole PTH is "superior to C-terminal and midregion assays for the prediction of histological type bone diseases.").

In one embodiment, a total PTH assay is utilized wherein an antibody specific for $PTH_{44-68}$ is utilized in addition to an antibody specific for $PTH_{52-84}$ in addition to other potential antibodies to determine a total PTH level.

The present disclosure also provides a more therapeutically predictive PTH ratios involving whole PTH levels, PTH fragment levels, and occasionally total PTH levels. The total PTH levels in this ratio include PTH fragments in addition to large PTH N-terminal fragments such as $PTH_{7-84}$. These PTH fragments include a category of PTH fragments referred to elsewhere in the present disclosure as large inactive fragments and are not necessarily C-terminal nor N-terminal PTH fragments as described herein. As provided herein, PTH fragments included in the present total PTH determinations include $PTH_{7-84}$, in addition to other PTH fragments. Thus, an important aspect of the present enhanced PTH ratio involves monitoring a majority, and more preferably all, of the circulating PTH fragments in a subject such that a total PTH assay will measure N-terminal, C-terminal and mid-terminal PTH fragments. In a related aspect, the fragments measured in the enhanced ratio include $PTH_{7-84}$ in addition to other PTH fragments as described herein.

For example, an enhanced PTH ratio comprised of whole PTH versus total PTH (measuring most or all circulating PTH fragments in addition to whole PTH) will generally provide a lower percentage as compared with a PTH ratio measuring a total PTH ratio comprising whole PTH versus "total" PTH (consisting of whole PTH plus large N-terminal PTH fragments such as $PTH_{7-84}$). This lower percentage is due to the measurement of additional fragments in addition to $PTH_{7-84}$ as comprising the total PTH. Prior PTH totals generally provided lower numbers than $PTH_{7-84}$ totals including PTH fragments in addition to $PTH_{7-84}$. These totals were lower because PTH fragments other than large N-terminal fragments were not recognized. The present invention acknowledges this previous flaw in PTH totals in addition to the enhanced predictive and therapeutic benefits of ratios derived from measuring PTH fragments in addition to circulating N-terminal fragments.

The presently contemplated PTH ratios are useful to provide cutoff valuations to determine whether a subject suffers from adynamic bone disease (ADN), mild hyperparathyroidism (mild HPT) or severe hyperparathyroidism (severe HPT). Frequently, the present ratios are useful for initial diagnosis. However, these ratios may be equally useful to monitor and guide therapy for subjects. In one preferred embodiment, the present ratios are utilized in conjunction with measurement of CAP and/or whole PTH levels. Table 1 below provides a reference table for bone turnover rates as they relate to whole PTH levels and PTH ratios consisting of $PTH_{1-84}$ versus $PTH_{7-84}$.

TABLE 1

|  | Normal Turnover | High Turnover | Adynamic Bone Disease |
|---|---|---|---|
| Ratio $PTH_{1-84}/PTH_{7-84}$ | Between about 1.4 to about 2.0 | Greater than about 2.0 | Less than about 1.4 |
| PTH level $PTH_{1-84}$ (pg/ml) | Between about 90-170 | Greater than about 170 | Less than about 90 |

While not bound by theory, in light of current standards and practices, reliance solely on the values and ratios in Table 1 for determination and differentiation between the three listed bone turnover rate categories would be misplaced without reference to additional data including, for example, bone histology information and/or additional fragment related information (as provided herein).

Example ratios include variations of PTH parameters comprised of whole PTH (wPTH), C-terminal PTH (cPTH), and mid-terminus PTH fragments (mPTH). Depending on the antibodies utilized, cross-reactivity between these parameters may be witnessed (and corrected). A non-limiting list of example ratios of the present disclosure include wPTH/cPTH, wPTH/mPTH, wPTH/(cPTH+mPTH), wPTH/(cPTH−wPTH)+(mPTH−wPTH), wPTH/(cPTH+mPTH−wPTH), wPTH/(wPTH+mPTH+cPTH), cPTH/mPTH, mPTH/cPTH, cPTH/wPTH, mPTH/wPTH, and so forth. One of skill in the art would recognize that the inverse of these PTH ratios and other combinations of these parameters are equally suitable in the present methods. Moreover, CAP may be utilized as a PTH ratio parameter and used in conjunction with whole PTH levels, total PTH levels and/or PTH fragment levels in the contemplated ratios.

For example, Table 2 below provides a series of PTH ratio cutoff values. Antibodies specific for whole PTH (wPTH), mid-terminus PTH fragments (mPTH), and C-terminal PTH (cPTH) fragments and corresponding histology data are utilized to generate PTH level raw data providing the base values for ratio cutoffs. Each of the ratios presented below are generated based on the levels of cPTH, mPTH and/or wPTH as depicted.

TABLE 2

| Ratio composition | Cutoff (about) | Indication |
|---|---|---|
| wPTH/(cPTH + mPTH) | <0.020 | ADN |
| wPTH/(cPTH + mPTH) | >0.020 | Severe HPT |
| wPTH/(cPTH + mPTH) | 0.020 | Mild HPT |
| wPTH/((cPTH − wPTH) + (mPTH − wPTH)) | <0.0185 | ADN |
| wPTH/((cPTH − wPTH) + (mPTH − wPTH)) | >0.0185 | Severe HPT |
| wPTH/((cPTH − wPTH) + (mPTH − wPTH)) | >0.0185 | Mild HPT |
| wPTH/(cPTH + mPTH − wPTH) | <0.020 | ADN |
| wPTH/(cPTH + mPTH − wPTH) | >0.020 | Severe HPT |
| wPTH/(cPTH + mPTH − wPTH) | 0.020 | Mild HPT |
| wPTH/(wPTH + mPTH + cPTH) | <0.0175 | ADN |
| wPTH/(wPTH + mPTH + cPTH) | >0.0175 | Severe HPT |
| wPTH/(wPTH + mPTH + cPTH) | >0.0175 | Mild HPT |
| wPTH/cPTH | <0.103 | ADN |
| wPTH/cPTH | >0.103 | Severe HPT |
| wPTH/cPTH | 0.103 | Mild HPT |
| wPTH/mPTH | <0.0225 | ADN |
| wPTH/mPTH | >0.0225 | Severe HPT |
| wPTH/mPTH | >0.0225 | Mild HPT |

While Table 2 presents cutoff ranges for each of three clinical indications, variation for each may exist. The term "about" is used with each cutoff as a particularly preferred value range having slight inherent variation which may include the cutoff point as well. One of skill in the art would understand that PTH assay parameters could be changed such that the cutoff point may vary from that provided above; such variation falls within the scope of the present disclosure. In one embodiment, the cutoff point represents a median cutoff value for an indication. In a preferred embodiment, the cutoff point represents a range below or above which a majority or all subjects having a particular indication fall within.

There is a tremendous need to be able to non invasively separate the dialysis patients with ADN from those suffering from high bone turnover to avoid over treatment of ADN dialysis patients. Over treatment of dialysis patients with ADN is a frequent occurrence under presently utilized methods. For example, calcium based phosphate binders such as Zemplar® and Calcijex® (Abbott Laboratories), for example, have been used to treat dialysis patients. Under the treatment protocols utilized and recommended, these patients are at a great risk of over treatment due to inaccurate measurement of PTH levels (including wPTH and PTH fragment levels). For example, the proportion of dialysis patients treated with calcium based phosphate binders that become afflicted with ADN rose sharply during the time spanning 1995 to 2000 from 12% to 48% of such patients. See, e.g., Malluche, H. H., *The Importance of Bone Health in ESRD: Out of the Frying Pan, Into the Fire?*, World Congress on Nephrology, Berlin, Germany (June 2003) (based on unpublished data). It is postulated that this increase is due, in large part, to over treatment of dialysis patients; and this over treatment of dialysis patients is due, in turn, to ineffective PTH level monitoring (including whole PTH and PTH fragment levels). Moreover, K/DOQI recommends whole PTH as the only marker useful for separating ADN from HBT dialysis patients. See K/DOQI Clinical Practice Guidelines for Bone Metabolism and Disease in Chronic Kidney Disease, *Draft Guideline Statements and Treatment Algorithms* (February 2003). However, whole PTH levels fail to consistently separate ADN from HBT dialysis patients. See Qi, Q, et al., *Am. J. Kidney Dis.* 26:622-31 (1995); Quarles, L D, et al., *J. Clin. Endocrinol. Metab.* 75:145-150 (1992). It is recognized herein that such guidelines would appear to propagate the over treatment phenomenon. Accordingly, the present compositions and methods illustrate the effectiveness of separating ADN from HBT dialysis patients via PTH ratio results, rather than via measurement of whole PTH levels alone, and their use for routine clinical management of renal disease, osteoporosis, and/or dialysis patients.

D. PTH Assay Locations

The presently contemplated methods may be performed in a variety of settings and by a variety of entities. However, in general, the present methods and materials may be made available in a health care setting. Frequently, the present methods, e.g., determining and monitoring of PTH levels and ratios as described herein, are utilized in the clinical management of disease or disorders in a subject by a care provider or clinical laboratory. A health care setting, as used herein, includes clinical laboratories, doctor's offices, hospitals, health management organization facilities, and outpatient care facilities, amongst a variety of other nontraditional settings useful for the delivery of care and subject testing.

E. PTH Sequences

The present disclosure contemplates the use of parathyroid hormone peptides, peptide fragments, polynucleotides encoding whole PTH or PTH fragment peptides, and antibodies that specifically bind whole PTH and/or PTH fragments derived from a variety of mammalian sources. See, e.g., Caetano, A. R., et al., *Equus Genome Res.* 9(12): 1239-1249 (1999) (horse), U.S. Patent Application Publication US 2002/0110871 A1 (rat, mouse, bovine, canine, porcine), U.S. patent application Ser. Nos. 09/344,639 and 09/231,422 (human). By way of nonlimiting example, PTH derived from the following sources and having the following peptide sequences are contemplated herein:

Human $PTH_{1-84}$ (SEQ ID NO: 1):
SER-VAL-SER-GLU-ILE-GLN-LEU-MET-HIS-ASN-LEU-GLY-

LYS-HIS-LEU-ASN-SER-MET-GLU-ARG-VAL-GLU-TRP-LEU-

ARG-LYS-LYS-LEU-GLN-ASP-VAL-HIS-ASN-PHE-VAL-ALA-

LEU-GLY-ALA-PRO-LEU-ALA-PRO-ARG-ASP-ALA-GLY-SER-

GLN-ARG-PRO-ARG-LYS-LYS-GLU-ASP-ASN-VAL-LEU-VAL-

GLU-SER-HIS-GLU-LYS-SER-LEU-GLY-GLU-ALA-ASP-LYS-

ALA-ASP-VAL-ASN-VAL-LEU-THR-LYS-ALA-LYS-SER-GLN.

Rat $PTH_{1-84}$ (SEQ ID NO: 2):
ALA-VAL-SER-GLU-ILE-GLN-LEU-MET-HIS-ASN-LEU-GLY-

LYS-HIS-LEU-ALA-SER-VAL-GLU-ARG-MET-GLN-TRP-LEU-

ARG-LYS-LYS-LEU-GLN-ASP-VAL-HIS-ASN-PHE-VAL-SER-

LEU-GLY-VAL-GLN-MET-ALA-ALA-ARG-GLU-GLY-SER-TYR-

GLN-ARG-PRO-THR-LYS-LYS-GLU-ASP-ASN-VAL-LEU-VAL-

ASP-GLY-ASN-SER-LYS-SER-LEU-GLY-GLU-GLY-ASP-LYS-

ALA-ASP-VAL-ASP-VAL-LEU-VAL-LYS-ALA-LYS-SER-GLN.

Mouse $PTH_{1-84}$ (SEQ ID NO: 3):
ALA-VAL-SER-GLU-ILE-GLN-LEU-MET-HIS-ASN-LEU-GLY-

LYS-HIS-LEU-ALA-SER-VAL-GLU-ARG-MET-GLN-TRP-LEU-

ARG-ARG-LYS-LEU-GLN-ASP-MET-HIS-ASN-PHE-VAL-SER-

LEU-GLY-VAL-GLN-MET-ALA-ALA-ARG-ASP-GLY-SER-HIS-

GLN-LYS-PRO-THR-LYS-LYS-GLU-GLU-ASN-VAL-LEU-VAL-

ASP-GLY-ASN-PRO-LYS-SER-LEU-GLY-GLU-GLY-ASP-LYS-

ALA-ASP-VAL-ASP-VAL-LEU-VAL-LYS-SER-LYS-SER-GLN.

Bovine $PTH_{1-84}$ (SEQ ID NO: 4):
ALA-VAL-SER-GLU-ILE-GLN-PHE-MET-HIS-ASN-LEU-GLY-

LYS-HIS-LEU-SER-SER-MET-GLU-ARG-VAL-GLU-TRP-LEU-

ARG-LYS-LYS-LEU-GLN-ASP-VAL-HIS-ASN-PHE-VAL-ALA-

LEU-GLY-ALA-SER-ILE-ALA-TYR-ARG-ASP-GLY-SER-SER-

GLN-ARG-PRO-ARG-LYS-LYS-GLU-ASP-ASN-VAL-LEU-VAL-

GLU-SER-HIS-GLN-LYS-SER-LEU-GLY-GLU-ALA-ASP-LYS-

ALA-ASP-VAL-ASP-VAL-LEU-ILE-LYS-ALA-LYS-PRO-GLN.

Canine $PTH_{1-84}$ (SEQ ID NO: 5):
SER-VAL-SER-GLU-ILE-GLN-PHE-MET-HIS-ASN-LEU-GLY-

LYS-HIS-LEU-SER-SER-MET-GLU-ARG-VAL-GLU-TRP-LEU-

ARG-LYS-LYS-LEU-GLN-ASP-VAL-HIS-ASN-PHE-VAL-ALA-

LEU-GLY-ALA-PRO-ILE-ALA-HIS-ARG-ASP-GLY-SER-SER-

GLN-ARG-PRO-LEU-LYS-LYS-GLU-ASP-ASN-VAL-LEU-VAL-

-continued
GLU-SER-TYR-GLN-LYS-SER-LEU-GLY-GLU-ALA-ASP-LYS-

ALA-ASP-VAL-ASP-VAL-LEU-THR-LYS-ALA-LYS-SER-GLN.

Porcine PTH$_{1-84}$ (SEQ ID NO: 6):
SER-VAL-SER-GLU-ILE-GLN-PHE-MET-HIS-ASN-LEU-GLY-

LYS-HIS-LEU-SER-SER-LEU-GLU-ARG-VAL-GLU-TRP-LEU-

ARG-LYS-LYS-LEU-GLN-ASP-VAL-HIS-ASN-PHE-VAL-ALA-

LEU-GLY-ALA-SER-ILE-VAL-HIS-ARG-ASP-GLY-GLY-SER-

GLN-ARG-PRO-ARG-LYS-LYS-GLU-ASP-ASN-VAL-LEU-VAL-

GLU-SER-HIS-GLN-LYS-SER-LEU-GLY-GLU-ALA-ASP-LYS-

ALA-ALA-VAL-ASP-VAL-LEU-ILE-LYS-ALA-LYS-PRO-GLN.

Horse PTH$_{1-86}$ (SEQ ID NO: 7):
LYS-ARG-SER-VAL-SER-GLU-ILE-GLN-LEU-MET-HIS-ASN-

LEU-GLY-LYS-HIS-LEU-ASN-SER-VAL-GLU-ARG-VAL-GLU-

TRP-LEU-ARG-LYS-LYS-LEU-GLN-ASP-VAL-HIS-ASN-PHE-

ILE-ALA-LEU-GLY-ALA-PRO-ILE-PHE-HIS-ARG-ASP-GLY-

GLY-SER-GLN-ARG-PRO-ARG-LYS-LYS-GLU-ASP-ASN-VAL-

LEU-ILE-GLU-SER-HIS-GLN-XXX-SER-LEU-GLY-GLU-ALA-

ASP-LYS-ALA-ASP-VAL-ASP-VAL-LEU-SER-LYS-THR-LYS-

SER-GLN.

VII. EXEMPLARY MODES FOR CARRYING OUT THE INVENTION

In disclosing the present invention, one should remember that there are a number of closely analogous, species dependent forms of PTH (see above). The amino acid sequence of hPTH is shown in FIG. 1. However, for rat PTH, bovine PTH, or porcine PTH, for example, one finds the substitutions at some of the amino acids in the hPTH sequence (see, e.g., SEQ ID NOs: 1-7). For the purposes of the present invention, one can use interchangeably antibodies or antibody fragments to forms of these PTHs, although it is preferred to use an antibody with specificity for PTH having a sequence matching the species in which the PTH measurements are made.

A. Whole PTH Immunoassay

Figure 2:
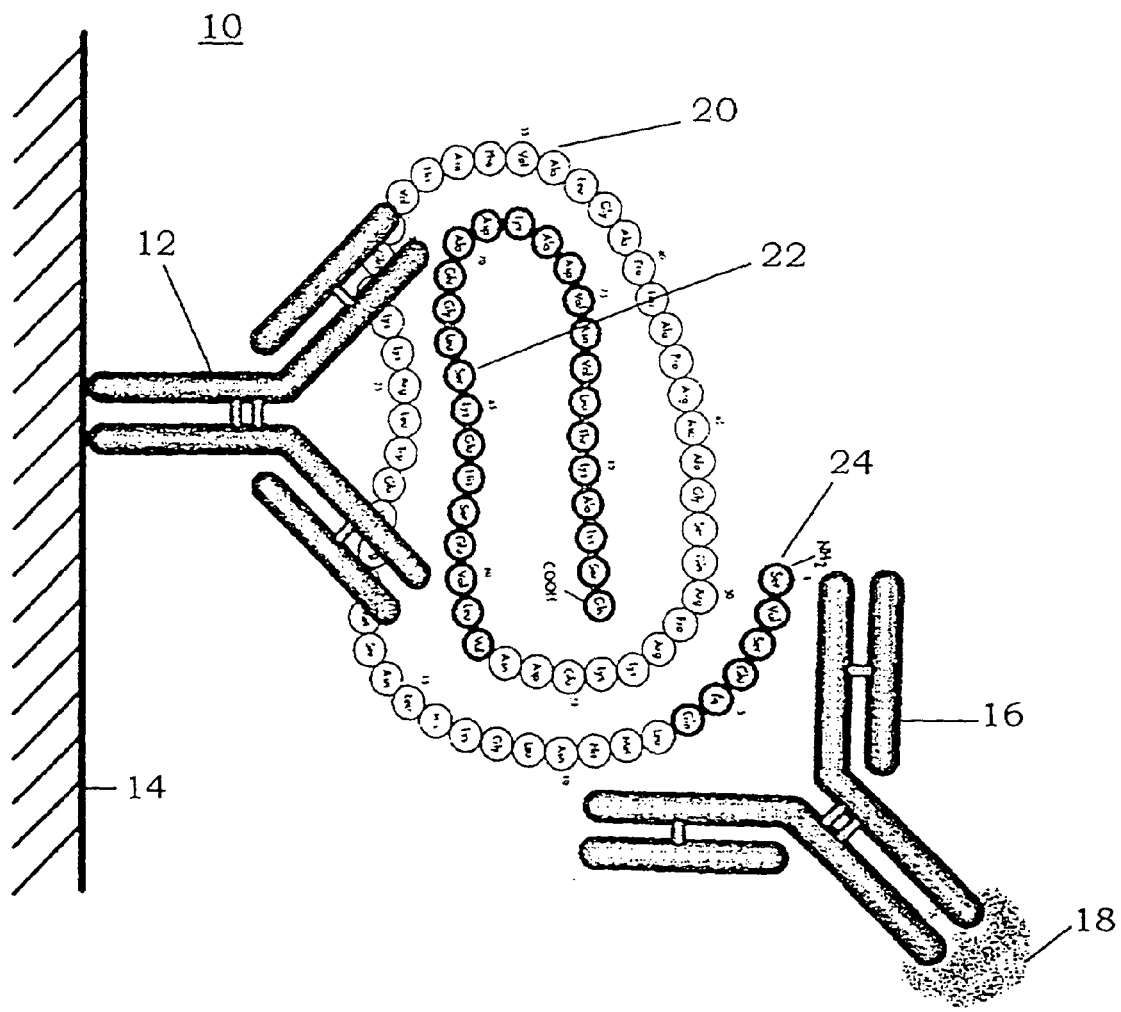
FIG. 2 is a diagrammatic view of a wPTH assay using the present antibody as a tracer element.
Figure 3:
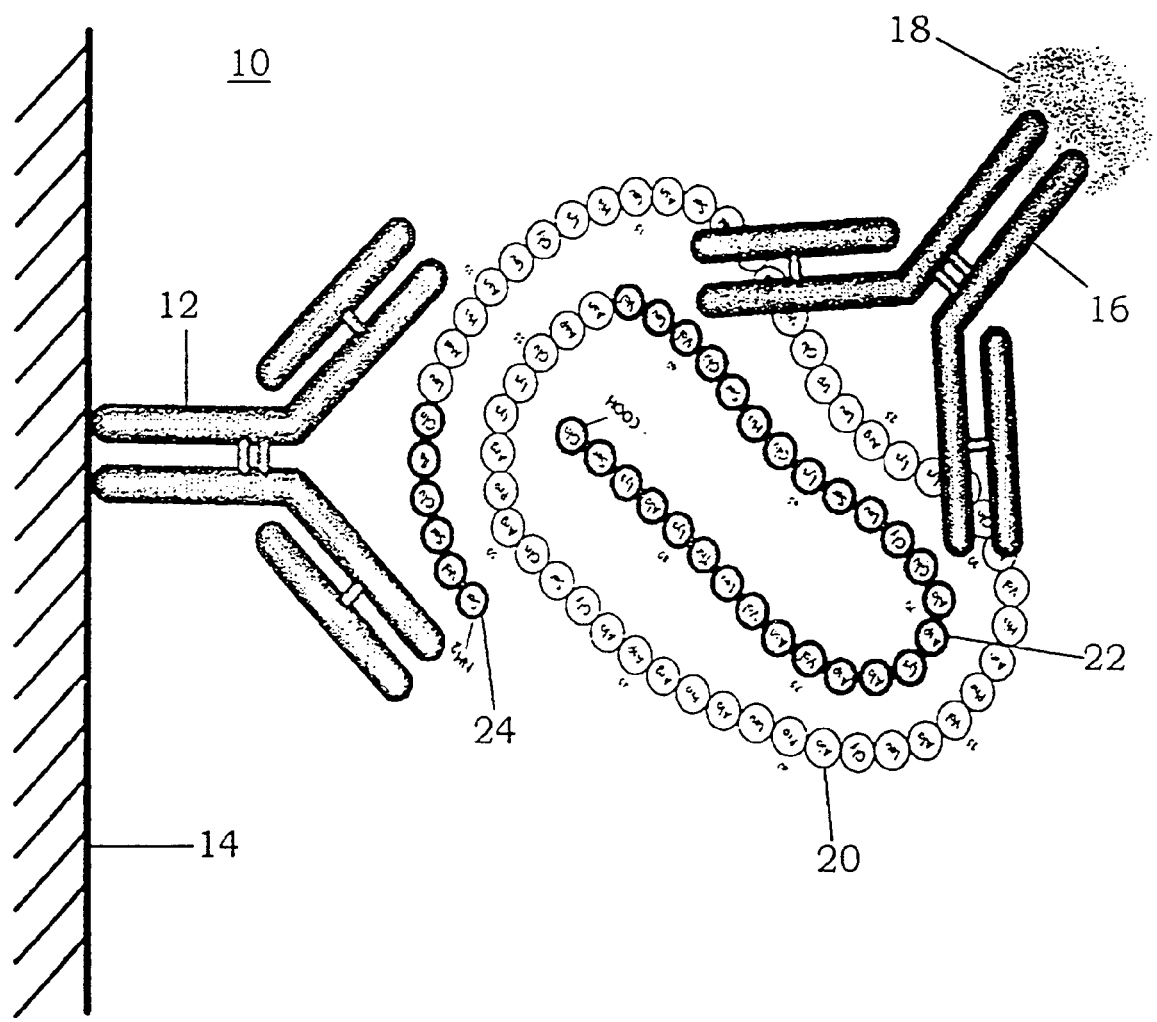
FIG. 3 is a diagrammatic view of a wPTH assay using the present antibody as a capture element.

A preferred embodiment of the present invention is an immunoradiometric assay 15 (IRMA), often referred to as a sandwich assay, as shown FIGS. 2 and 3. Elements employed in such an assay (10) include a capture antibody (12) attached to a solid support (14) and a signal antibody (16) having a label (18), attached thereto (20). Typically, one selects a capture antibody that is specific for C-terminal PTH fragments (22), while the label antibody is specific for the initial wPTH peptide sequence which comprises a domain for adenylate cyclase activation (24), as shown in FIG. 2. However, one could reverse the specificity of these antibodies, as is shown in FIG. 3.

Alternatively, one could create an immunoassay in which wPTH is either precipitated from solution or otherwise differentiated in a solution, as in conventional precipitating assays or turbidometric assays. For example, one can use at least three antibodies to form a precipitating mass. In addition to the initial wPTH sequence antibody and a C-terminal antibody, one can use at least a third antibody which attaches to the mid portion of Pm. The combined mass of wPTH and the at least three antibodies would form a labeled precipitating mass which can be measured by conventional techniques.

Another method would be to couple the initial wPTH sequence antibody to colloidal solid supports, such as latex particles. More specifically, one can create a signal antibody by iodinating 50 micrograms of affinity purified goat anti-(1-6) PTH antibody (Scantibodies Laboratory, Inc., Santee Calif., U.S.A.) by oxidation with chloramine T, incubation for 25 seconds at room temperature with 1 millicurie of 125-1 radioisotope and reduction with sodium metabisulfate. Unincorporated 125-1 radioisotope is separated from the 125-1-Goat anti-(1-6) PTH signal antibody by, passing the iodination mixture over a PD-10 desalting column (Pharmacia, Uppsala, Sweden) and following the manufacturers instructions. The fractions collected from the desalting column are measured in a gamma counter and those fractions representing the 125-1-goat anti-(1-6) PTH antibody are pooled and diluted to approximately 300,000 D PM (disintegrations per minute) per 100 microliters. This solution is the tracer solution to be used in the whole PTH IRMA.

Capture antibody coated tubes can be created by attaching affinity purified goat anti PTH 39-84 antibody, (Scantibodies Laboratory, Inc., Santee, Calif., U.S.A.), to 12×75 mm polystyrene tubes (Nunc, Denmark) by means of passive absorption techniques which are known to those of skill in the art. The tubes are emptied and dried, 20 creating solid phase antibody coated tubes.

Figure 4:
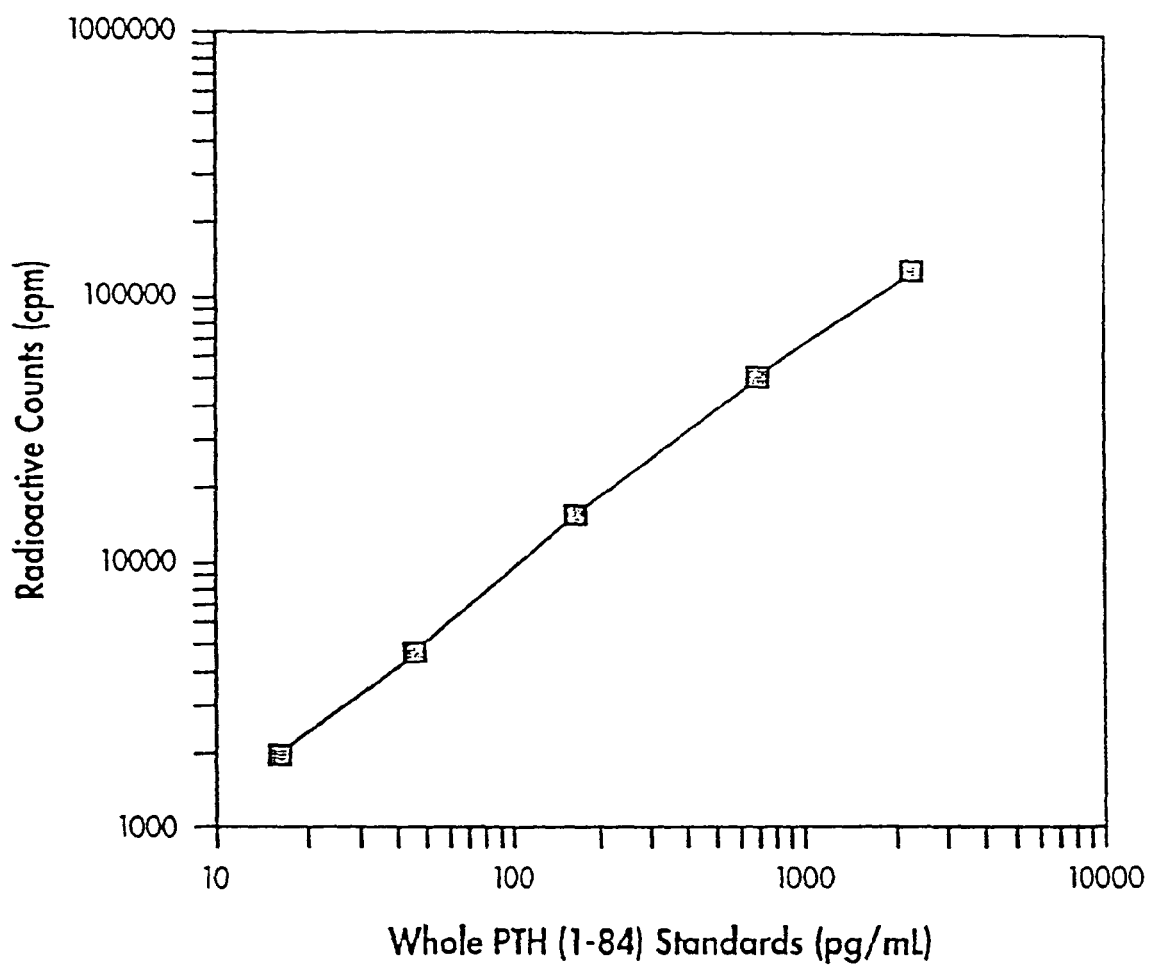
FIG. 4 is a graph showing a standard curve for a wPTH assay.

To conduct a whole PTH assay of a sample, 200 microliter samples of human serum are added to the solid phase antibody coated tubes. To each tube is added 100 microliters of the tracer solution (labeled goat anti-(1-6) PTH signal antibody). The tubes 25 are incubated at room temperature with shaking at 170 rpm for 20-22 hours. During this time the immunochemical reaction of forming the sandwich of {solid phase goat anti-(39-84) PTH antibody}-{whole PTH}-{125-1-goat anti-(1-6) PTH antibody} takes place. Following this incubation, the test tubes are washed with distilled water. Radioactivity on the solid phase, which amount corresponds to the quantity of wPTH present, is measured using a gamma counter. The radioactivity data for the samples is processed by conventional analysis with use of the results from standards and controls and computer software in order that the concentration of whole PTH in the samples may be ascertained. FIG. 4 shows a standard curve for such an assay.

B. Initial Whole PTH Sequence Peptide

In order to make the signal antibody in the above assays, first one makes a synthetic PTH peptide corresponding either to human PTH$_{1-8}$, rat PTH$_{1-8}$, mouse PTH$_{1-8}$, bovine PTH$_{1-8}$, canine PTH$_{1-8}$, porcine PTH$_{1-8}$, horse PTH$_{1-8}$, human PTH$_{1-15}$, rat PTH$_{1-15}$, mouse PTH$_{1-15}$, bovine PTH$_{1-15}$, canine PTH$_{1-15}$, porcine PTH$_{1-15}$, or horse PTH$_{1-15}$, or at least four amino acids in the common sequence. Although not bound by theory, suitable synthetic PTH peptides may extend beyond the PTH$_{1-8}$ as illustrated above, i.e., to position 84 of PTH$_{1-84}$. For example, any of the variety of PTH N-terminal fragments are suitable initial peptide sequences for this aspect. The selected peptide can play two roles in making an assay, first as a specific source for creating a polyclonal antibody or monoclonal antibody source for signal antibody or capture antibody, and second as part of an affinity purification means for isolating the desired signal antibody or capture antibody.

Briefly, such a peptide can be synthesized on an Applied Biosystems, Inc. (Foster City, Calif., U.S.A.) Model 431 automated peptide synthesizer employing Fmoc (9-fluoronylmethoxycarbonyl) as the alpha-amino protecting group. All amino acids and solvents are from Applied Biosystems and are of synthesis grade. Following synthesis, the peptide is cleaved from the resin, and side chains are de-blocked, using a cleavage cocktail 20 containing 6.67% phenol, 4.4% (v/v) thioanisole and 8.8% ethanedithiol in trifluoroacetic acid (TFA). The cleaved peptide is precipitated and washed several times in cold diethyl ether. It is then dissolved in water and lyophilized. The crude peptide is subjected to amino acid analysis (Waters PICO-TAG System, Boston, Mass., U.S.A.) and reversed-phase HPLC using a VYDAC (TM) C8 column with 0.1% TFA in water and 25 99.9% acetonitrile in 0.1% TFA as the mobile buffers. The presence of a single major peak along with the appropriate amino acid composition is taken as evidence that the peptide is suitable for further use.

The resulting peptide is then attached to cross linked agarose beads (activated Sepharose 4B from Pharmacia, Uppsala, Sweden) according to instructions from the manufacturer. Armed with the initial peptide sequence on a bead, one can affinity purify a polyclonal antibody serum source to isolate the initial sequence antibody for the wPTH immunoassay.

In a particularly preferred embodiment, initial sequence PTH antibodies successfully distinguish between initial PTH peptides and C-terminal and mid-terminal PTH peptides, such that they specifically bind initial sequence PTH peptides.

In another preferred embodiment, the above methods are utilized to synthesize mid-terminal and C-terminal PTH peptide fragments. After synthesis of these peptides, the above methods are utilized to generate and isolate mid-terminal PTH antibodies and/or C-terminal PTH antibodies. In a preferred embodiment, mid-terminal PTH antibodies specifically bind mid-terminal PTH peptide fragments. In another preferred embodiment, C-terminal PTH antibodies specifically bind C-terminal PTH peptide fragments.

C. Initial Sequence Whole PTH Antibody

In another embodiment, to create an affinity-purified initial sequence whole PTH antibody, one first uses a PTH sequence peptide having an intact N-terminal as described above as part of an immunogen for injection into a goat. For example, a PTH peptide ranging from $PTH_{1-34}$ to $PTH_{1-84}$ may be utilized. The peptide can be used either by itself as an injectable immunogen, incorporated into a non PTH peptide having a molecular weight, typically, of between about 5,000 and 10,000,000, or as part of the wPTH complete sequence. The immunogen is mixed with an equal volume of Freund's complete adjuvant which is a mixture of light mineral oil, Arlacel detergent, and inactivated mycobacterium tuberculosis bacilli. The resulting mixture is homogenized to produce an aqueous/oil emulsion which is injected into the animal (typically a goat) for the primary immunization. The immunogen dose is approximately 50-400 micrograms. The goats are injected monthly with the same dose of immunogen complex except no mycobacterium tuberculosis bacilli is used in these subsequent injections. The goats are bled monthly, approximately three months after the 20 primary immunization. The serum (or antiserum) is derived from each bleeding by separating the red blood cells from the blood by centrifugation and removing the antiserum which is rich in initial sequence PTH antibodies.

To purify the antiserum for the desired initial sequence whole PTH antibody, one packs a separation column with a PTH sequence peptide (e.g., a PTH peptide ranging from $PTH_{1-5}$ to $PTH_{1-15}$) bound beads described above, washes the column and equilibrates it with 0.01 M phosphate buffered saline (PBS). The antiserum is loaded onto the column and washed with 0.01 M PBS in order to remove antibodies without the initial sequence PTH specificity. The bound specific goat initial sequence PTH polyclonal antibody is eluted from the solid phase that includes optionally $PTH_{1-15}$ to $PTH_{1-15}$ in the column by passing an elution solution of 0.1 M glycine hydrochloride buffer, pH 2.5 through the column. The eluted polyclonal antibody is neutralized after it leaves the column with either the addition of 1.0 M phosphate buffer, pH 7.5 or by a buffer exchange with 0.01 M PBS, as is known to those of skill in the art. The polyclonal antibody is stored at 2-8 degrees centigrade.

In another embodiment, to create an affinity-purified anti-(1-6) PTH antibody, one first uses a selected initial PTH sequence peptide as described above as part of an immunogen for injection into a goat. The peptide can be used either by itself as an injectable immunogen, incorporated into a non PTH peptide having a molecular weight, typically, of between about 5,000 and 10,000,000, or as part of the wPTH complete sequence. The immunogen is mixed with an equal volume of Freund's complete adjuvant which is a mixture of light mineral oil, Arlacel detergent, and inactivated mycobacterium tuberculosis bacilli. The resulting mixture is homogenized to produce an aqueous/oil emulsion which is injected into the animal (typically a goat) for the primary immunization. The immunogen dose is approximately 50-400 micrograms. The goats are injected monthly with the same dose of immunogen complex except no mycobacterium tuberculosis bacilli is used in these subsequent injections. The goats are bled monthly, approximately three months after the 20 primary immunization. The serum (or antiserum) is derived from each bleeding by separating the red blood cells from the blood by centrifugation and removing the antiserum which is rich in (1-6) PTH antibodies.

To purify the antiserum for the desired (1-6) PTH antibody, one packs a separation column with the initial PTH sequence peptide bound beads described above, washes the column and equilibrates it with 0.01 M phosphate buffered saline (PBS). The antiserum is loaded onto the column and washed with 0.01 M PBS in order to remove antibodies without the (1-6) PTH specificity. The bound specific goat anti-(1-6) PTH polyclonal antibody is eluted from the solid phase PTH 1-6 in the column by passing an elution solution of 0.1 M glycine hydrochloride buffer, pH 2.5 through the column. The eluted polyclonal antibody is neutralized after it leaves the column with either the addition of 1.0 M phosphate buffer, pH 7.5 or by a buffer exchange with 0.01 M PBS, as is known to those of skill in the art. The polyclonal antibody is stored at 2-8 degrees centigrade.

One of skill in the art would understand that there are acceptable variations in the above practices. See, e.g., Harlow E, Lane D: Antibodies: A laboratory manual. Cold Spring Harbor Laboratory Press, Cold Spring Harbor, N.Y., 1988; Kohler & Milstein, Nature, 256: 495-7 (1975). While not bound by theory, the above practices are suitable for production of other PTH N-terminal antibodies using selected N-terminal PTH sequence peptides as described herein.

In a particularly preferred embodiment, initial sequence PTH antibodies successfully distinguish between initial PTH peptides and both C-terminal and mid-terminus PTH peptides, such that they specifically bind initial sequence PTH peptides.

D. C-Termimal Sequence PTH Antibody

To create an affinity-purified anti-(60-84) PTH antibody, one first uses a selected C-terminal PTH sequence peptide as described above as part of an immunogen for injection into a goat. In another embodiment, the immunogen comprises whole PTH peptide, e.g., $PTH_{1-84}$. The peptide can be used either by itself as an injectable immunogen, incorporated into a non PTH peptide having a molecular weight, typically, of between about 5,000 and 10,000,000. The immunogen is mixed with an equal volume of Freunds complete adjuvant which is a mixture of light mineral oil, Arlacel detergent, and inactivated mycobacterium tuberculosis bacilli. The resulting mixture is homogenized to produce an aqueous/oil emulsion which is injected into the animal (typically a goat) for the primary immunization. The immunogen dose is approximately 50-400 micrograms. The goats are injected monthly with the same dose of immunogen complex except no mycobacterium tuberculosis bacilli is used in these subsequent injections. The goats are bled monthly, approximately three months after the 20 primary immunization. The serum (or antiserum) is derived from each bleeding by separating the red blood cells from the blood by centrifugation and removing the antiserum which contains (60-84) PTH antibodies. In another embodiment, the antiserum is removed which contains (60-84) PTH antibodies in addition to other PTH antibodies, e.g., whole PTH antibodies.

To purify the antiserum for the desired (60-84) PTH antibody, one packs a separation column with the C-terminal PTH sequence peptide bound beads described above, washes the column and equilibrates it with 0.01 M phosphate buffered saline (PBS). The antiserum is loaded onto the column and washed with 0.01 M PBS in order to remove antibodies without the (60-84) PTH specificity. The bound specific goat anti-(60-84) PTH polyclonal antibody is eluted from the solid phase PTH 1-6 in the column by passing an elution solution of 0.1 M glycine hydrochloride buffer, pH 2.5 through the column. The eluted polyclonal antibody is neutralized after it leaves the column with either the addition of 1.0 M phosphate buffer, pH 7.5 or by a buffer exchange with 0.01 M PBS, as is known to those of skill in the art. The polyclonal antibody is stored at 2-8 degrees centigrade.

One of skill in the art would understand that there are acceptable variations in the above practices. See, e.g., Harlow E, Lane D: Antibodies: A laboratory manual. Cold Spring Harbor Laboratory Press, Cold Spring Harbor, N.Y., 1988; Kohler & Milstein, Nature, 256: 495-7 (1975). While not bound by theory, the above practices are suitable for production of other PTH C-terminal antibodies using selected C-terminal PTH sequence peptides as described herein. For example, PTH peptides such as $PTH_{53-84}$, $PTH_{60-84}$, $PTH_{64-84}$, $PTH_{65-84}$, $PTH_{39-84}$, $PTH_{23-84}$, $PTH_{19-84}$, and other C-terminal PTH peptides as described above.

In a particularly preferred embodiment, C-terminal PTH antibodies successfully distinguish between C-terminal peptides and both initial sequence and mid-terminus PTH peptides, such that they specifically bind C-terminal PTH peptides.

E. Mid-Terminus Sequence PTH Antibody

To create an affinity-purified anti-(44-68) PTH antibody, one first uses a selected mid-terminus PTH sequence peptide as described above as part of an immunogen for injection into a goat. In another embodiment, the immunogen comprises whole PTH peptide, e.g., $PTH_{1-84}$. The peptide can be used either by itself as an injectable immunogen, incorporated into a non PTH peptide having a molecular weight, typically, of between about 5,000 and 10,000,000. The immunogen is mixed with an equal volume of Freunds complete adjuvant which is a mixture of light mineral oil, Arlacel detergent, and inactivated mycobacterium tuberculosis bacilli. The resulting mixture is homogenized to produce an aqueous/oil emulsion which is injected into the animal (typically a goat) for the primary immunization. The immunogen dose is approximately 50-400 micrograms. The goats are injected monthly with the same dose of immunogen complex except no mycobacterium tuberculosis bacilli is used in these subsequent injections. The goats are bled monthly, approximately three months after the 20 primary immunization. The serum (or antiserum) is derived from each bleeding by separating the red blood cells from the blood by centrifugation and removing the antiserum which contains (44-68) PTH antibodies. In another embodiment, the antiserum is removed which contains (44-68) PTH antibodies in addition to other PTH antibodies, e.g., whole PTH antibodies.

To purify the antiserum for the desired (44-68) PTH antibody, one packs a separation column with the mid-terminus PTH sequence peptide bound beads described above, washes the column and equilibrates it with 0.01 M phosphate buffered saline (PBS). The antiserum is loaded onto the column and washed with 0.01 M PBS in order to remove antibodies without the (44-68) PTH specificity. The bound specific goat anti-(44-68) PTH polyclonal antibody is eluted from the solid phase PTH 1-6 in the column by passing an elution solution of 0.1 M glycine hydrochloride buffer, pH 2.5 through the column. The eluted polyclonal antibody is neutralized after it leaves the column with either the addition of 1.0 M phosphate buffer, pH 7.5 or by a buffer exchange with 0.01 M PBS, as is known to those of skill in the art. The polyclonal antibody is stored at 2-8 degrees centigrade.

One of skill in the art would understand that there are acceptable variations in the above practices. See, e.g., Harlow E, Lane D: Antibodies: A laboratory manual. Cold Spring Harbor Laboratory Press, Cold Spring Harbor, N.Y., 1988; Kohler & Milstein, Nature, 256: 495-7 (1975). While not bound by theory, the above practices are suitable for production of other PTH mid-terminus antibodies using selected mid-terminus PTH sequence peptides as described herein. For example, PTH peptides such as $PTH_{44-60}$, $PTH_{7-53}$, $PTH_{12-53}$, $PTH_{17-53}$, $PTH_{22-53}$, $PTH_{27-53}$, $PTH_{30-35}$, $PTH_{32-53}$, $PTH_{32-53}$, $PTH_{37-53}$, $PTH_{42-53}$, $PTH_{4-53}$, and other mid-terminal PTH peptides as described above.

In a particularly preferred embodiment, mid-terminus PTH antibodies successfully distinguish between mid-terminus peptides and both initial sequence and C-terminal PTH peptides, such that they specifically bind mid-terminus PTH peptides.

F. Comparison Between Second Generation Whole PTH and Total PTH Assays

Figure 10:
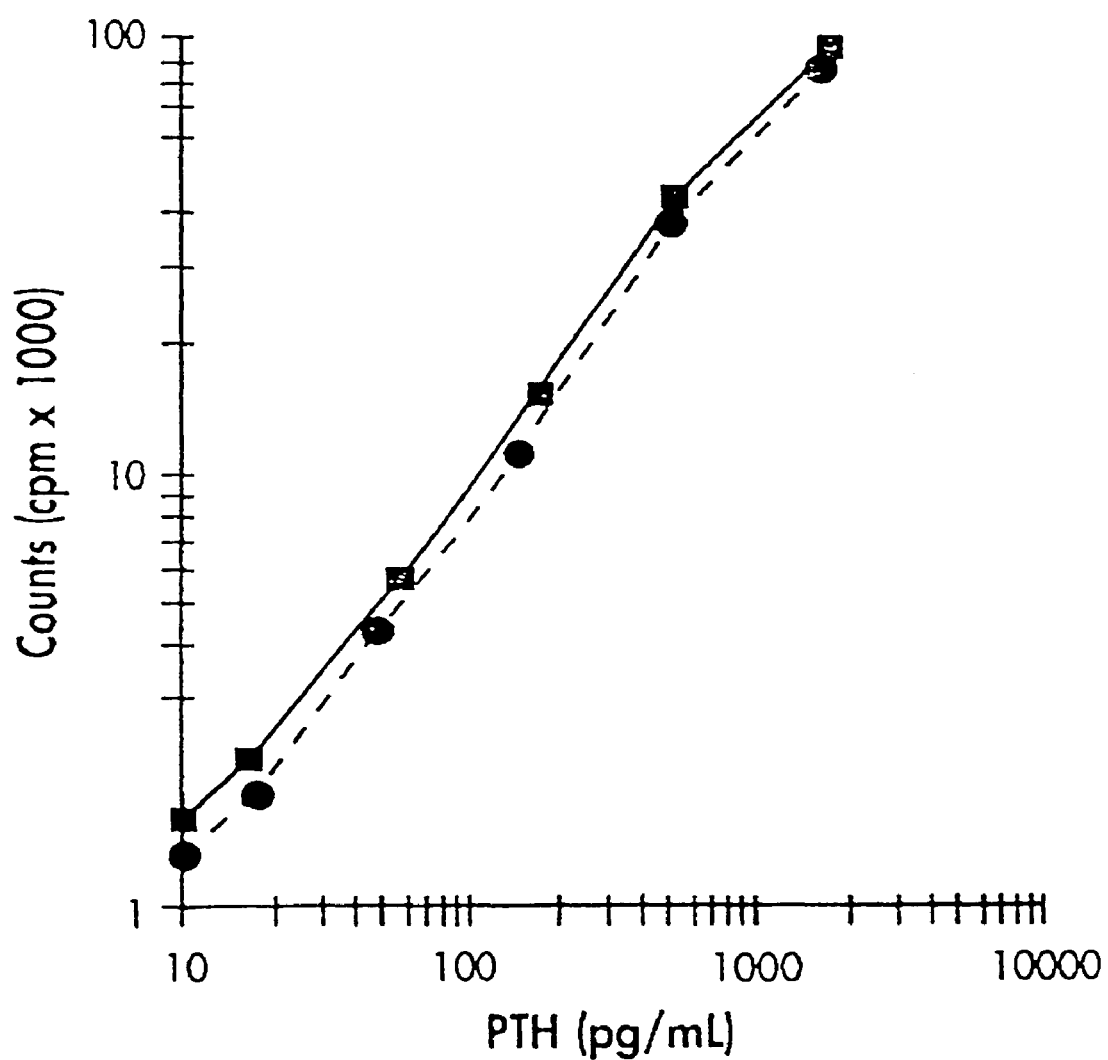
FIG. 10 is a graph demonstrating complete cross-reactivity of wPTH and PIN in a total PTH assay used in the present invention.

The present whole IRMA assay was compared to a conventional intact PTH or I-PTH immunoassay, the Allegro Nichols Intact-PTH assay, (which is commercially available and made by Nichols Institute Diagnostics of San Juan Capistrano, Calif., U.S.A.), in both PTH normal persons and those suffering from chronic uremia. This I-PTH immunoassay, detects both $PTH_{7-84}$ and wPTH (see FIG. 10).

Figure 5:
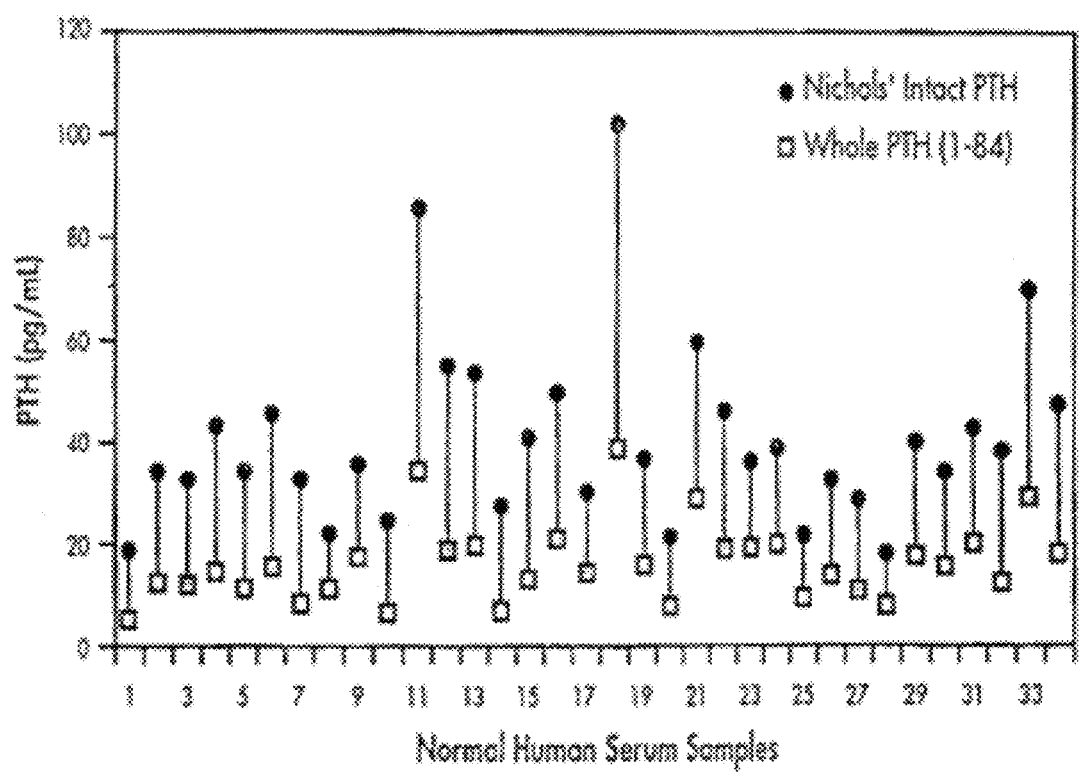
FIG. 5 is a graph comparing a conventional I-PTH assay with the present wPTH assay for healthy normal persons with "normal" PTH values.
Figure 6A:
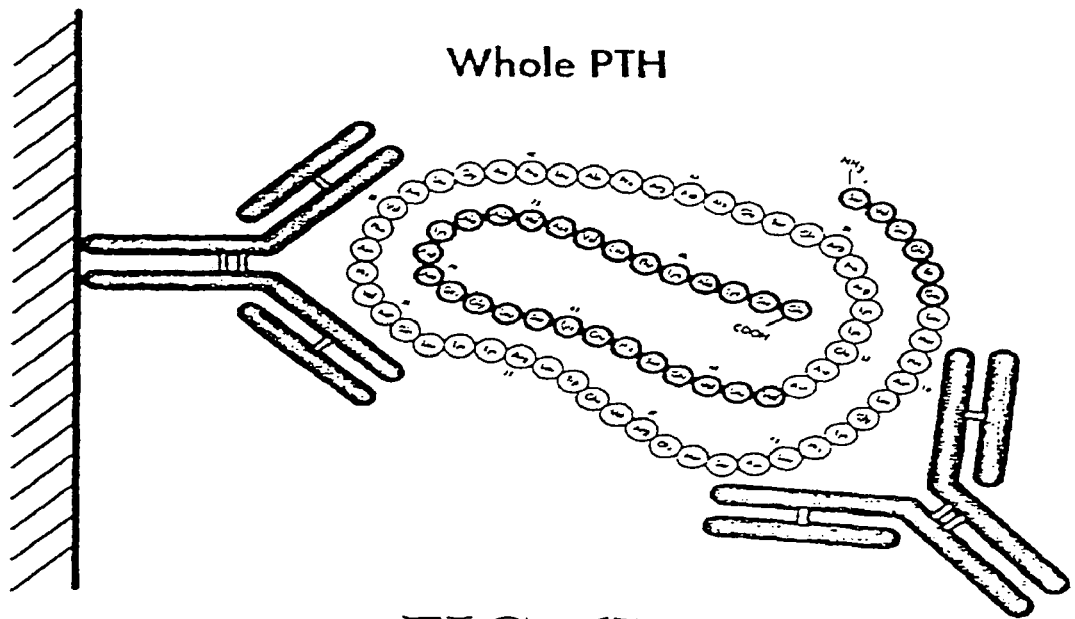
FIG. 6 is a diagrammatic view showing interference from non (1-84) PTH fragments in conventional I-PTH assays.
Figure 6B:
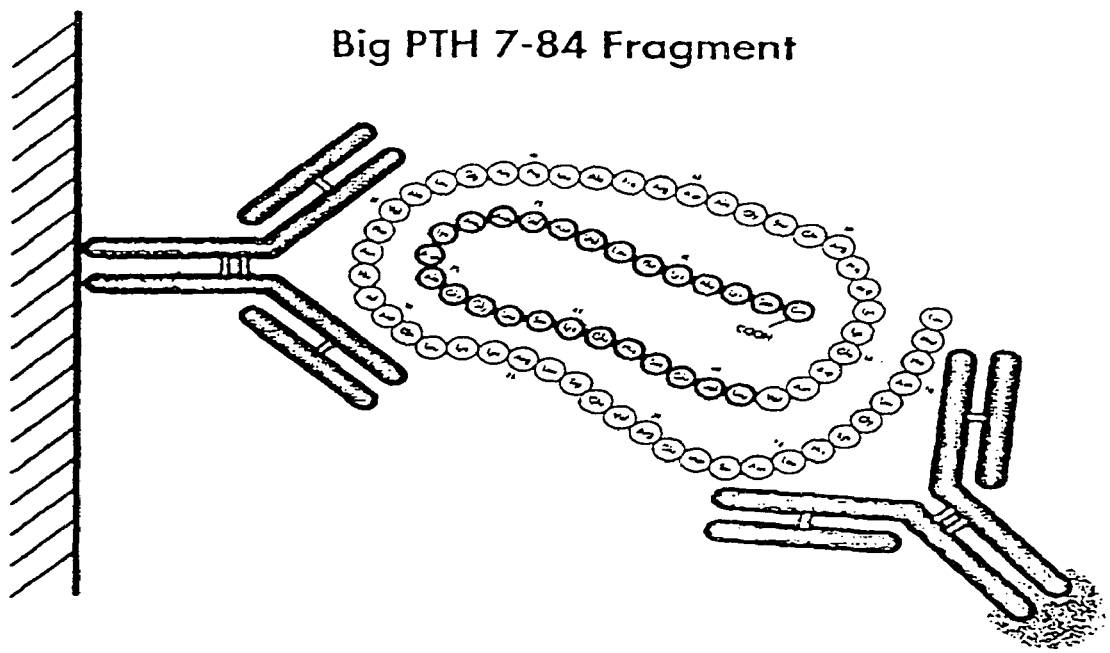
Figure 11:
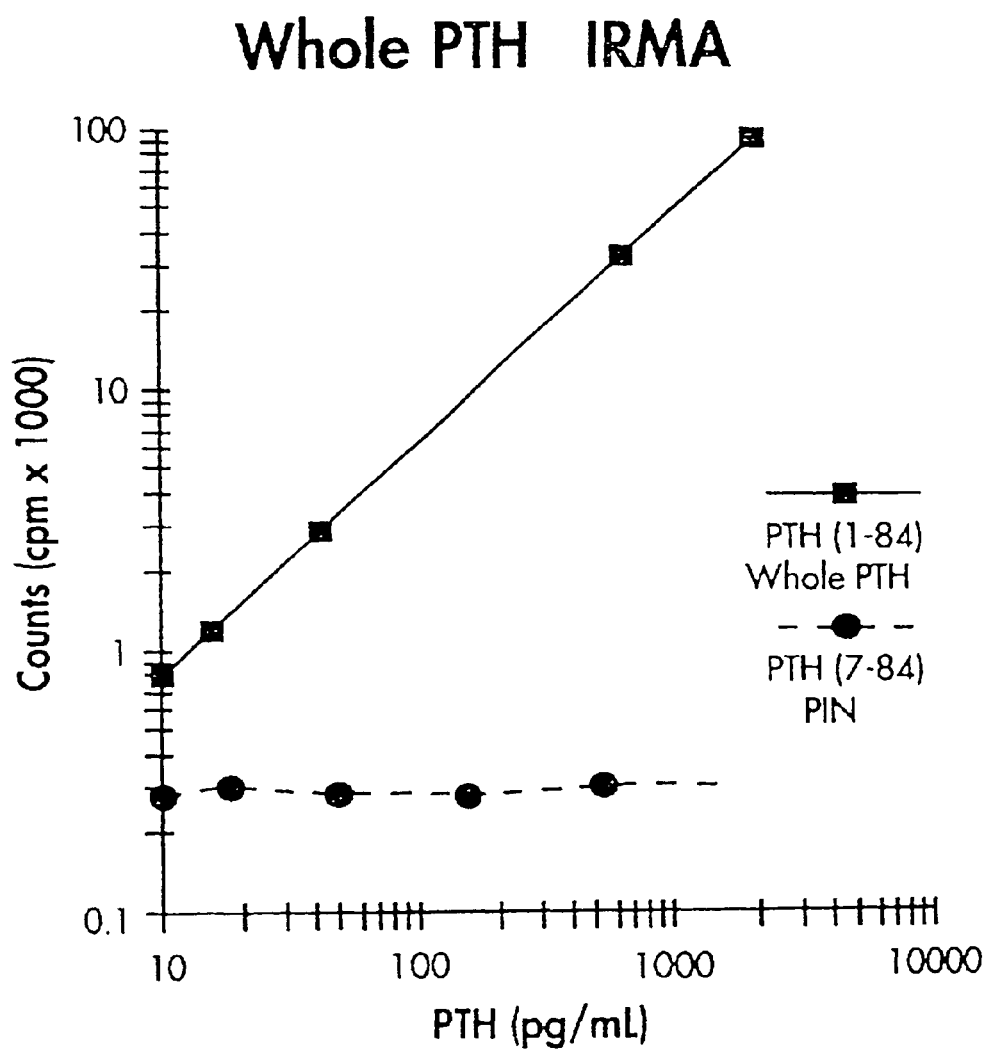
FIG. 11 is a graph demonstrating how the whole PTH assay used in the present invention does not detect to PIN.

FIG. 5 shows the results for 34 normal human serum samples from healthy subjects which were assayed both by the present wPTH IRMA and the above I-PTH assay. In every case, the level of wpm detected by the IRMA is lower than that reported by the I-PTH assay, demonstrating the ability of the present IRMA to avoid detecting the interfering large, non (1-84) PTH fragment detected by the I-pm assay, (see FIG. 11). FIG. 6 illustrates how such interference can occur. An N-terminal PTH specific signal antibody which is not specific to the initial PTH peptide sequence, as in the present invention, can detect not only wPTH (as in the upper part of FIG. 6), but also can detect PIN, the large, non (1-84) PTH fragment, (as in the lower part of FIG. 6).

Figure 7:
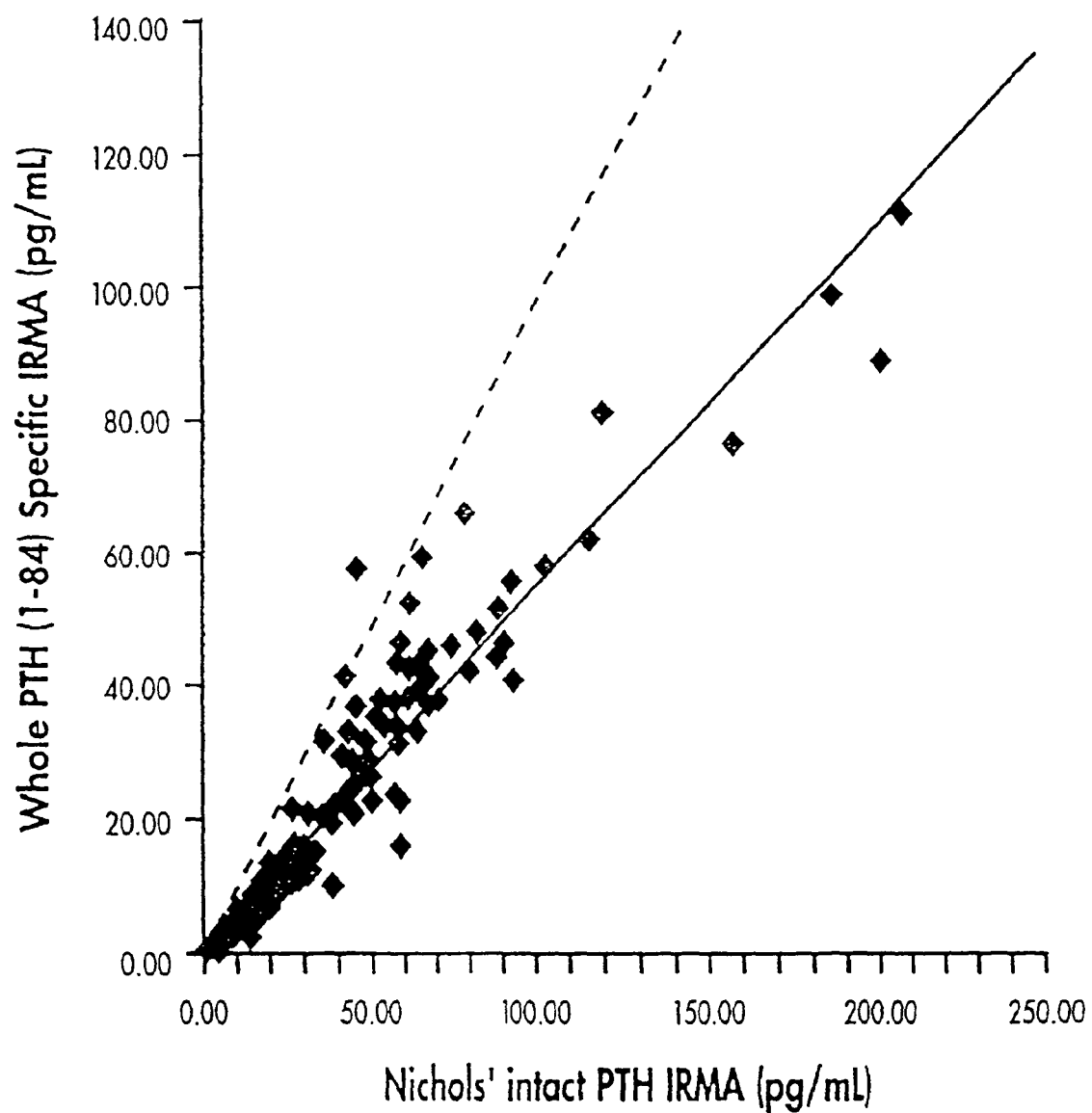
FIG. 7 is a graph comparing a conventional I-PTH assay with the present wPTH assay for patients with chronic uremia.
Figure 8:
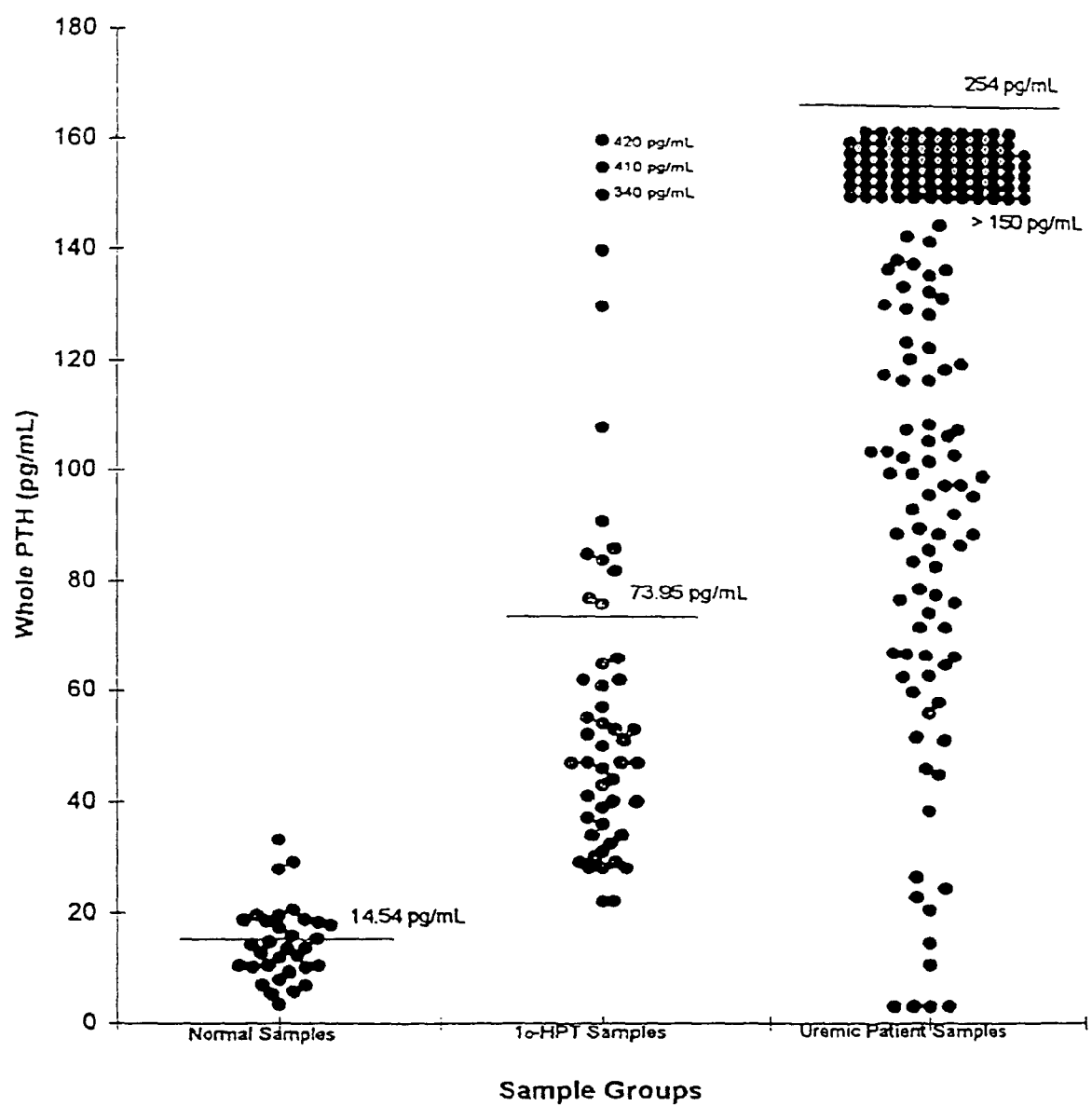
FIG. 8 is a graph showing the distribution of values for healthy normal persons, patients with primary hyperparathyroidism, and patients with chronic uremia.
Figure 9:
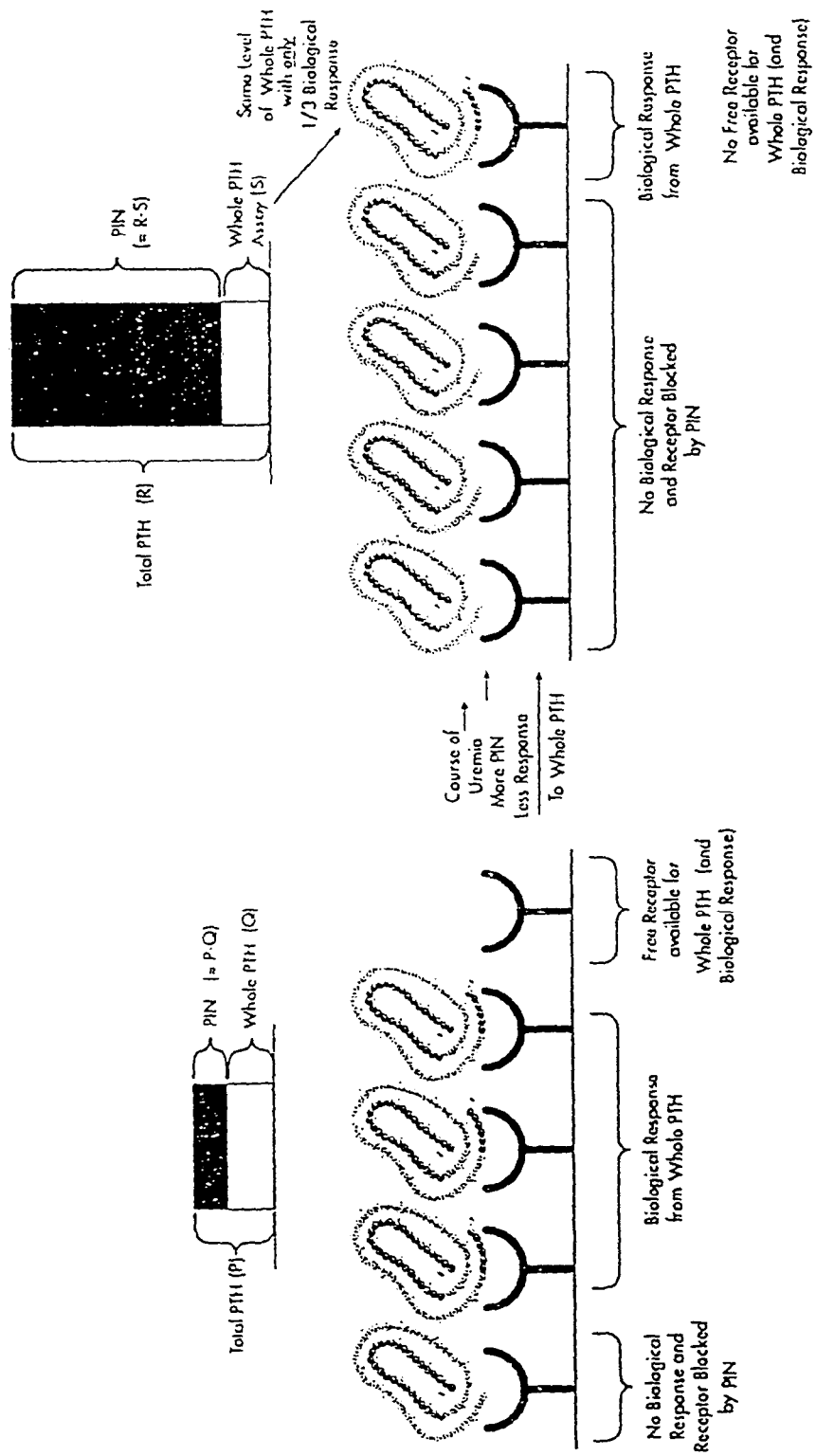
FIG. 9 is a diagrammatic view showing how PIN blocks the action of wPTH at the receptor level, thereby making the person insensitive to the biological effects of wPTH.

A comparison of assay results for 157 chronic uremic patients is shown in FIG. 7. Serum samples from these patients were measured using the wPTH IRMA and the above I-PTH assay. In every case the wPTH levels are lower than I-PTH values.

G. Cyclase Active PTH/PTH Fragment Ratio Assay

Another preferred embodiment of the present invention is an immunoradiometric assay (IRMA), often referred to as a sandwich assay. As described herein, elements employed in such an assay include a capture antibody attached to a solid support and a signal antibody having a label, attached thereto. Typically, one selects a capture antibody that is specific for C-terminal PTH fragments, while the label antibody is specific for a mid-terminus PTH peptide sequence as described herein. However, one could reverse the specificity of these antibodies.

Alternatively, one could create an immunoassay in which PTH fragments are either precipitated from solution or otherwise differentiated in a solution, as in conventional precipitating assays or turbidometric assays. For example, one can use at least two or more antibodies to form a precipitating mass. These antibodies having specificity for N-terminal, C-terminal and/or mid-terminal portions of PTH. The combined mass of the PTH fragment and the antibodies would form a labeled precipitating mass which can be measured by conventional techniques.

Another method would be to couple C-terminal PTH sequence antibody to colloidal solid supports, such as latex particles. In addition, a signal antibody can be created by iodinating 50 micrograms of affinity purified goat anti-(7-53) PTH antibody by oxidation with chloramine T, incubation for 25 seconds at room temperature with 1 millicurie of 125-1 radioisotope and reduction with sodium metabisulfate. Unincorporated 125-1 radioisotope is separated from the 125-1-Goat anti-(7-53) PTH signal antibody by, passing the iodination mixture over a PD-10 desalting column (Pharmacia, Uppsala, Sweden) and following the manufacturers instructions. The fractions collected from the desalting column are measured in a gamma counter and those fractions representing the 125-1-goat anti-(7-53) PTH antibody are pooled and diluted to approximately 300,000 D PM (disintegrations per minute) per 100 microliters. This solution is the tracer solution to be used in the PTH assay.

Other signal antibodies can also be provided using affinity purified goat anti-(12-53) PTH antibody, purified goat anti-(17-53) PTH antibody, purified goat anti-(22-53) PTH antibody, purified goat anti-(27-53) PTH antibody, purified goat anti-(32-53) PTH antibody, purified goat anti-(37-53) PTH antibody, purified goat anti-(42-53) PTH antibody, purified goat anti-(47-53) PTH antibody, and the like. Antibodies specific for other mid-terminus PTH peptide fragments and epitopes described herein are also contemplated. Optimally, PTH antibodies specific for different PTH portions are obtained utilizing different goats and ELISA methods may be utilized to determine optimum antibody generation and use. See, e.g., Harlow E, Lane D: Antibodies: A laboratory manual. Cold Spring Harbor Laboratory Press, Cold Spring Harbor, N.Y., 1988.

Capture antibody coated tubes can be created by attaching affinity purified goat anti-(39-84) PTH antibody to 12×75 mm polystyrene tubes (Nunc, Denmark) by means of passive absorption techniques which are known to those of skill in the art. The tubes are emptied and dried, creating solid phase antibody coated tubes. The present methods are also useful to create solid phase antibody coated tubes having any of a variety of C-terminal PTH antibodies. For example, antibodies generated specific for $PTH_{40-84}$ ranging to those specific for $PTH_{60-84}$ and $PTH_{65-84}$ are useful in the present methods. One of skill in the art would understand that the specificity for the capture and label/signal antibodies may be reversed.

A selection of these specific antibodies may be utilized to assay samples from patients having adynamic low bone turnover. In one example, a sample of 50-100 ml blood is drawn from a subject having adynamic low bone turnover. The sample is then subject to multiple sandwich assays utilizing the capture and label antibodies described herein above. Each assay determines the level of whole PTH, in addition to one or more PTH fragments present in the sample. The level of whole PTH is then compared with a variety of permutations of PTH fragment levels and total PTH levels. The comparison results are then viewed in light of corresponding bone histological data for the patient to determine one or more comparison schemes that are predictive of bone turnover rate. Ratio results that are produced through the practice of this assay are represented in Table I and are further described hereinbefore.

A PTH ratio is predictive of certain bone turnover rates in a subject. The present disclosure recognizes that additional PTH fragments may be present in a sample beyond $PTH_{7-84}$, and often effect the bone turnover rate. Thus, the present compositions, kits and methods are particularly useful to account for PTH fragments in addition to $PTH_{7-84}$, having associated therapeutic and predictive benefits for a subject. Although not bound by theory, one component of this discovery is illustrated, in part, by the observation that although a percentage of circulating large PTH fragments are inactive, others exhibit antagonistic effects to those exhibited by whole PTH. Thus, accounting for all, or a majority of, the circulating PTH fragments in a particular assay will reduce the variability of the result, and increase its therapeutic, diagnostic and predictive potential.

H. Clinical Use

The present wPTH and PIN assays have been used in a clinical setting involving 188 persons. The group included 31 persons having normal healthy parathyroid glands and 157 patients with chronic uremia who are undergoing dialysis on a continuous basis. Each person had a blood sample drawn which was assayed using a wPTH assay from Scantibodies Laboratory, Inc. as well as an I-PTH assay from Nichols Institute which gave total PTH values.

Table 3 shows the results individually and comparatively, of the wPTH, PIN, and 10 total PTH assays from chronic uremic patients on dialysis.

TABLE 3

| Patient No. | Total PTH pg/ml | CAP pg/ml | CIP pg/ml | CIP to Total PTH | CIP to CAP | CAP to Total PTH |
|---|---|---|---|---|---|---|
| 1 | 1410 | 740 | 670 | 48% | 91% | 52% |
| 2 | 185 | 89 | 96 | 52% | 108% | 48% |
| 3 | 231 | 104 | 127 | 55% | 122% | 45% |
| 4 | 1020 | 590 | 430 | 42% | 73% | 53% |
| 5 | 270 | 159 | 111 | 41% | 70% | 59% |
| 6 | 201 | 100 | 101 | 50% | 101% | 50% |
| 7 | 380 | 100 | 280 | 74% | 280% | 26% |
| 8 | 460 | 277 | 183 | 40% | 66% | 60% |
| 9 | 380 | 197 | 183 | 48% | 93% | 52% |
| 10 | 880 | 522 | 358 | 41% | 69% | 59% |
| 11 | 310 | 154 | 156 | 50% | 101% | 50% |
| 12 | 880 | 451 | 429 | 49% | 95% | 51% |
| 13 | 670 | 418 | 252 | 38% | 60% | 63% |
| 14 | 390 | 221 | 169 | 43% | 76% | 57% |
| 15 | 170 | 108 | 62 | 36% | 57% | 64% |
| 16 | 510 | 381 | 129 | 25% | 34% | 75% |
| 17 | 200 | 67 | 133 | 67% | 199% | 34% |
| 18 | 170 | 109 | 61 | 36% | 56% | 64% |
| 19 | 360 | 199 | 161 | 45% | 81% | 55% |
| 20 | 260 | 164 | 96 | 37% | 59% | 63% |
| 21 | 440 | 372 | 68 | 15% | 18% | 85% |
| 22 | 120 | 51.7 | 68.3 | 57% | 132% | 43% |
| 23 | 600 | 527 | 73 | 12% | 14% | 83% |
| 24 | 220 | 130 | 90 | 41% | 69% | 59% |
| 25 | 190 | 136 | 54 | 28% | 40% | 72% |

TABLE 3-continued

| Patient No. | Total PTH pg/ml | CAP pg/ml | CIP pg/ml | CIP to Total PTH | CIP to CAP | CAP to Total PTH |
|---|---|---|---|---|---|---|
| 26 | 220 | 118 | 102 | 46% | 86% | 54% |
| 27 | 630 | 334 | 296 | 47% | 89% | 53% |
| 28 | 150 | 90 | 60 | 40% | 67% | 60% |
| 29 | 170 | 106 | 64 | 38% | 60% | 62% |
| 30 | 810 | 489 | 321 | 40% | 66% | 60% |
| 31 | 570 | 319 | 251 | 44% | 79% | 56% |
| 32 | 570 | 133 | 103 | 18% | 22% | 82% |
| 33 | 400 | 564 | 100 | 25% | 33% | 75% |
| 34 | 560 | 89 | 182 | 33% | 48% | 68% |
| 35 | 310 | 121 | 189 | 61% | 156% | 39% |
| 36 | 240 | 98 | 142 | 59% | 145% | 41% |
| 37 | 280 | 133 | 157 | 54% | 118% | 48% |
| 38 | 230 | 124 | 106 | 46% | 85% | 54% |
| 39 | 350 | 319 | 31 | 9% | 10% | 91% |
| 40 | 200 | 133 | 67 | 34% | 50% | 67% |
| 41 | 920 | 564 | 356 | 39% | 63% | 61% |
| 42 | 210 | 89 | 121 | 58% | 136% | 42% |
| 43 | 1990 | 904 | 1086 | 55% | 120% | 45% |
| 44 | 300 | 212 | 88 | 29% | 42% | 71% |
| 45 | 260 | 132 | 128 | 49% | 97% | 51% |
| 46 | 140 | 72 | 68 | 49% | 94% | 51% |
| 47 | 250 | 129 | 121 | 48% | 94% | 52% |
| 48 | 130 | 72 | 58 | 45% | 81% | 56% |
| 49 | 1840 | 1000 | 840 | 46% | 84% | 54% |
| 50 | 280 | 167 | 113 | 40% | 68% | 60% |
| 51 | 490 | 268 | 222 | 45% | 83% | 55% |
| 52 | 150 | 77.1 | 72.9 | 49% | 95% | 51% |
| 53 | 140 | 58.1 | 81.9 | 59% | 141% | 42% |
| 54 | 210 | 92.7 | 117.3 | 56% | 127% | 44% |
| 55 | 160 | 79 | 81 | 51% | 103% | 49% |
| 56 | 480 | 296 | 184 | 38% | 62% | 62% |
| 57 | 480 | 281 | 199 | 41% | 71% | 59% |
| 58 | 270 | 120 | 150 | 56% | 125% | 44% |
| 59 | 97 | 45 | 52 | 54% | 116% | 46% |
| 60 | 330 | 154 | 176 | 53% | 114% | 47% |
| 61 | 110 | 56 | 54 | 49% | 96% | 51% |
| 62 | 660 | 456 | 204 | 31% | 45% | 69% |
| 633 | 300 | 137 | 163 | 54% | 119% | 46% |
| 64 | 240 | 145 | 95 | 40% | 66% | 60% |
| 65 | 100 | 66.5 | 33.5 | 34% | 50% | 67% |
| 66 | 410 | 416.3 | 6.3 | 2% | 2% | 102% |
| 67 | 410 | 235.7 | 174.3 | 43% | 74% | 57% |
| 68 | 45 | 14.4 | 30.6 | 68% | 213% | 32% |
| 69 | 200 | 102.3 | 97.7 | 49% | 96% | 51% |
| 70 | 300 | 134 | 166 | 55% | 124% | 45% |
| 71 | 320 | 202 | 118 | 37% | 58% | 63% |
| 72 | 440 | 254 | 186 | 42% | 73% | 58% |
| 73 | 190 | 99.6 | 90.4 | 48% | 91% | 52% |
| 74 | 160 | 74.6 | 85.4 | 53% | 114% | 47% |
| 75 | 600 | 429.8 | 170.2 | 28% | 40% | 72% |
| 76 | 1140 | 632 | 508 | 45% | 80% | 55% |
| 77 | 40 | 211 | 229 | 52% | 109% | 48% |
| 78 | 450 | 276 | 174 | 39% | 63% | 61% |
| 79 | 510 | 344 | 166 | 33% | 48% | 67% |
| 80 | 190 | 62.8 | 127.2 | 67% | 203% | 33% |
| 81 | 170 | 86 | 84 | 49% | 98% | 51% |
| 82 | 180 | 103.4 | 76.6 | 43% | 74% | 57% |
| 83 | 78 | 22.7 | 55.3 | 71% | 244% | 29% |
| 84 | 230 | 117 | 113 | 49% | 97% | 51% |
| 85 | 160 | 96 | 64 | 40% | 67% | 60% |
| 86 | 220 | 89 | 131 | 60% | 147% | 40% |
| 87 | 470 | 321.5 | 148.5 | 32% | 46% | 68% |
| 88 | 310 | 137 | 173 | 56% | 126% | 44% |
| 89 | 2050 | 1127 | 923 | 45% | 82% | 55% |
| 90 | 930 | 414 | 516 | 55% | 125% | 45% |
| 91 | 180 | 65 | 115 | 64% | 177% | 36% |
| 92 | 560 | 238 | 322 | 58% | 135% | 43% |
| 93 | 640 | 597 | 43 | 7% | 7% | 93% |
| 94 | 590 | 382 | 208 | 35% | 54% | 65% |
| 95 | 270 | 103 | 167 | 62% | 162% | 38% |
| 96 | 560 | 349 | 211 | 38% | 60% | 62% |
| 97 | 180 | 78 | 102 | 57% | 131% | 43% |
| 98 | 790 | 429 | 361 | 46% | 84% | 54% |
| 99 | 670 | 372 | 298 | 44% | 80% | 56% |
| 100 | 140 | 20.4 | 119.6 | 85% | 586% | 15% |
| 101 | 190 | 117 | 73 | 38% | 62% | 62% |
| 102 | 190 | 108 | 82 | 43% | 76% | 57% |
| 103 | 430 | 217 | 213 | 50% | 98% | 50% |
| 104 | 560 | 439 | 121 | 22% | 28% | 78% |
| 105 | 500 | 357.7 | 142.3 | 28% | 40% | 72% |
| 106 | 1560 | 777 | 783 | 50% | 101% | 50% |
| 107 | 62 | 24.3 | 37.7 | 61% | 155% | 39% |
| 108 | 430 | 226 | 204 | 47% | 90% | 53% |
| 109 | 160 | 67.2 | 92.8 | 58% | 138% | 42% |
| 110 | 530 | 346 | 184 | 35% | 53% | 65% |
| 111 | 260 | 142 | 118 | 45% | 83% | 55% |
| 112 | 580 | 163 | 41 | 72% | 256% | 28% |
| 113 | 440 | 579 | 139 | 32% | 24% | 132% |
| 114 | 500 | 232.3 | 267.7 | 54% | 115% | 46% |
| 115 | 160 | 60 | 100 | 63% | 167% | 38% |
| 116 | 340 | 202 | 138 | 41% | 68% | 59% |
| 117 | 260 | 138 | 122 | 47% | 88% | 53% |
| 118 | 260 | 119 | 141 | 54% | 118% | 46% |
| 119 | 160 | 84 | 76 | 48% | 90% | 53% |
| 120 | 130 | 46 | 84 | 65% | 183% | 35% |
| 121 | 190 | 104 | 86 | 45% | 83% | 55% |
| 122 | 420 | 334 | 86 | 20% | 26% | 80% |
| 123 | 630 | 440 | 190 | 30% | 43% | 70% |
| 124 | 75 | 26.4 | 48.6 | 65% | 184% | 35% |
| 125 | 260 | 143 | 117 | 45% | 82% | 55% |
| 126 | 640 | 409 | 231 | 36% | 56% | 64% |
| 127 | 130 | 66.7 | 63.3 | 49% | 95% | 51% |
| 128 | 700 | 381 | 319 | 46% | 84% | 54% |
| 129 | 560 | 376 | 184 | 33% | 49% | 67% |
| 130 | 240 | 107 | 133 | 55% | 124% | 45% |
| 131 | 110 | 63 | 47 | 43% | 75% | 57% |
| 132 | 420 | 297 | 123 | 29% | 41% | 71% |
| 133 | 580 | 229 | 351 | 61% | 153% | 39% |
| 134 | 310 | 201.2 | 108.8 | 35% | 54% | 65% |
| 135 | 160 | 97.9 | 62.1 | 39% | 63% | 61% |
| 136 | 290 | 138.7 | 151.3 | 52% | 109% | 48% |
| 137 | 200 | 96.2 | 103.8 | 52% | 108% | 48% |
| 138 | 770 | 662.7 | 107.3 | 14% | 16% | 86% |
| 139 | 290 | 130.7 | 159.3 | 55% | 122% | 45% |
| 140 | 260 | 219 | 41 | 16% | 19% | 84% |
| 141 | 350 | 211 | 139 | 40% | 66% | 60% |
| 142 | 730 | 463.5 | 266.5 | 37% | 57% | 63% |
| 143 | 490 | 231 | 259 | 53% | 112% | 47% |
| 144 | 160 | 87 | 73 | 46% | 84% | 54% |
| 145 | 380 | 222 | 158 | 42% | 71% | 58% |
| 146 | 210 | 93.5 | 116.5 | 55% | 125% | 45% |
| 147 | 630 | 383.4 | 246.6 | 39% | 64% | 61% |
| 148 | 150 | 83.2 | 66.8 | 45% | 80% | 55% |
| 149 | 320 | 152.5 | 167.5 | 52% | 110% | 48% |
| 150 | 900 | 467.6 | 432.4 | 48% | 92% | 52% |
| 151 | 1180 | 818.6 | 361.4 | 31% | 44% | 69% |
| 152 | 120 | 38.4 | 81.6 | 68% | 213% | 32% |
| 153 | 5230 | 1388 | 3842 | 73% | 277% | 27% |
| 154 | 34 | 10.5 | 23.5 | 69% | 224% | 31% |
| 155 | 1020 | 590.6 | 429.4 | 42% | 73% | 58% |
| 156 | 280 | 76.6 | 103.4 | 57% | 135% | 43% |
| 157 | 120 | 51.1 | 68.9 | 57% | 135% | 43% |
| Median | 300 | 154 | 127 | 46% | 84% | 54% |

TABLE 4 shows the results, individually and comparatively, of the wPTH, PIN, and total PTH assays from the normals.

TABLE 4

| Patient No. | Total PTH pg/ml | CAP pg/ml | CIP pg/ml | CIP to Total PTH | CIP to CAP | CAP to Total PTH |
|---|---|---|---|---|---|---|
| 1 | 17.13 | 3.32 | 13.81 | 81% | 416% | 19% |
| 2 | 32.92 | 10.49 | 22.43 | 68% | 214% | 32% |
| 3 | 31.32 | 10.31 | 21.01 | 67% | 204% | 33% |
| 4 | 41.84 | 12.72 | 29.12 | 70% | 229% | 30% |
| 5 | 33.03 | 10.09 | 22.94 | 69% | 227% | 31% |
| 6 | 44.32 | 14.23 | 30.09 | 68% | 211% | 32% |
| 7 | 31.47 | 6.80 | 24.67 | 78% | 363% | 22% |

TABLE 4-continued

| Patient No. | Total PTH pg/ml | CAP pg/ml | CIP pg/ml | CIP to Total PTH | CIP to CAP | CAP to Total PTH |
|---|---|---|---|---|---|---|
| 8 | 20.82 | 10.03 | 10.79 | 52% | 108% | 48% |
| 9 | 34.64 | 15.95 | 18.69 | 54% | 117% | 46% |
| 10 | 23.69 | 5.25 | 18.44 | 78% | 351% | 22% |
| 11 | 53.98 | 17.82 | 36.16 | 67% | 203% | 33% |
| 12 | 52.71 | 18.83 | 33.88 | 64% | 180% | 36% |
| 13 | 26.92 | 5.63 | 21.29 | 79% | 378% | 21% |
| 14 | 39.93 | 11.86 | 28.07 | 70% | 237% | 30% |
| 115 | 48.84 | 20.47 | 28.37 | 58% | 139% | 42% |
| 16 | 29.56 | 13.68 | 15.88 | 54% | 116% | 46% |
| 17 | 36.19 | 14.69 | 21.50 | 59% | 146% | 41% |
| 18 | 20.96 | 6.99 | 13.97 | 67% | 200% | 33% |
| 19 | 59.29 | 27.89 | 31.40 | 53% | 113% | 47% |
| 20 | 45.57 | 18.23 | 27.34 | 60% | 150% | 40% |
| 21 | 35.64 | 18.72 | 16.92 | 47% | 90% | 53% |
| 22 | 38.53 | 19.56 | 18.97 | 49% | 97% | 51% |
| 23 | 21.71 | 9.34 | 12.37 | 57% | 132% | 43% |
| 24 | 32.42 | 13.51 | 18.91 | 58% | 140% | 42% |
| 25 | 28.50 | 10.41 | 18.09 | 63% | 174% | 37% |
| 26 | 18.27 | 7.80 | 10.37 | 57% | 133% | 43% |
| 27 | 39.96 | 17.29 | 22.67 | 57% | 131% | 43% |
| 28 | 34.08 | 15.24 | 18.84 | 55% | 124% | 45% |
| 29 | 42.95 | 19.59 | 23.36 | 54% | 119% | 46% |
| 30 | 38.40 | 12.16 | 26.24 | 68% | 216% | 32% |
| 31 | 47.57 | 18.45 | 29.12 | 61% | 158% | 39% |
| MEDIAN | 34.64 | 13.51 | 21.50 | 61% | 158% | 39% |

Clearly, the statistically significant differences in the medians of these two groups demonstrates that one can differentiate between the two by using these assays alone or by comparing their respective values.

TABLE 5

| Sample Type | Total PTH pg/ml Median | CAP pg/ml Median | CIP pg/ml Median | CIP to Total PTH Median | CIP to CAP Median | CAP to Total PTH Median |
|---|---|---|---|---|---|---|
| Chronic uremia (n = 157) | 300 | 154 | 127 | 46% | 84% | 55% |
| Normal (n = 31) | 34.64 | 13.51 | 21.50 | 61% | 158% | 37% |
| P-Value | <0.0001 | <0.0001 | <0.0001 | <0.0001 | <0.0001 | <0.0001 |

I. Characterization of the "Whole" PTH IRMA Assay

This new Whole PTH two-site assay (Scantibodies Laboratories, Santee, Calif., USA) first employees and antibody that recognizes the 39-84 region of the PTH molecule. This antibody, produced in a goat and affinity purified, is present in relative excess and is immobilized onto polystyrene-coated tubes. The second antibody, also developed in a goat, was also affinity purified and recognizes only the first six amino acids (1 to 6; Ser-Val-Ser-Glu-Ile-Gln) of the human PTH molecule (FIG. 1). This anti-hPTH assay uses synthetic human PTH 1-84 as the standard, with a limit of detection of approximately 1 to 2 pg/mL. Normal values range from 5 to 35 pg/mL. The interassay and intra-assay coefficients of variation were found to be between 2 and 7% and recovery was from 96 to 106%. The Whole PTH assay was compared with the Intact PTH assay purchases from the Nichols Institute (I-Nichols, San Jan Capistrano, Calif., USA). Synthetic human PTH 1-84 and 7-84 were purchased from Bachem (Torrance, Calif. USA). To assess circulating levels of hPTH 1-84 and non-(1-84) PTH, heparinized blood samples were obtained before dialysis from 28 patients who had been maintained on chronic hemodialysis for 1.2 to 7.5 years and from 14 renal transplant patients (1 to 6 years).

1. Studies in vitro

Osteoblastic cell line. To compare the biological effects of the two peptides (hPTH 1-84 and 7-84), intracellular cAMP production was measured in the rate osteosarcoma cell line ROS/17.2, which has an osteoblastic phenotype and is known to increase cAMP production in response to PTH. Cells were cultured in Ham's F12 media containing 10% fetal bovine serum. Cells were plated out in 12-well plates at a density of 30,000 cells per well and grown to confluence. Cells were washed three times with KHMS buffer at 37° C. (KCl 4.0 mmol/L, $CaCl_2$ 1.25 mmol/L, $MgSO_4$ 1.25 mmol/L, $KH_2PO_4$ 1.2 mmol/L, HEPES 10 mmol/L, NaCl 100 mmol/L, $NaHCO_3$ 37 mmol/L, and glucose 10 mmol/L, pH 7.5). cAMP production was measured using 500 μL of KHMS buffer (37°) containing isobutyl-1 methylxantine (IBMX) 1.0 mmol/L and various concentrations ($10^{-11}$ to $10^{-8}$ mol/L) of hPTH 1-84 or hPTH 7-84. After a five-minute incubation, 100 μL of 1.8 mol/L pechloric acid were added. After an additional five-minute incubation at room temperature, 100 μL of 3 mol/$KHCO_3$ were added to neutralize the acid. Samples were centrifuged at 3000 rpm for 15 minutes, and the supernatants were assayed for cAMP [26].

Analysis of PTH in human parathyroid glands. Human parathyroid glands were placed in ice-cold phosphate-buffered saline and processed within 30 minutes of parathyroidectomy. Aliquots of parathyroid tissue were dissected, weighed, and homogenized in 500 μL of a buffer containing 100 mmol/L Tris-HCl, pH 7.5, 100 mmol/L NaCl, 1 mol/L DL-dithiothreitol, and a complete TM protease inhibitor cocktail (Boehringer-Mannheim, Mannheim, Germany). Homogenates were sonicated three times for 30 seconds each at 0° C. and centrifuged at 10,000× g for 15 minutes. Supernatants were kept at −70° C. until measurements of 1-84 PTH, non-(1-84) PTH, and total protein were performed.

2. Studies in vivo

Calcemic response. Normal female Sprague-Dawley rats weighing 225 to 250 g (Harlan, Indianapolis, Ind., USA) were parathyroidectomized (PTX) and fed a 0.02% calcium diet. Rats with a plasma calcium below 7.0 mg/dL after overnight fasting were included in the study. A 20 μg dose of hPTH 1-84 or 7-84 was given intraperitoneally to PTX rats in four doses of 5 μg each at 30-minute intervals (0, 30, 60, and 90 minutes). For control studies, the rats received vehicle (saline solution) alone. Blood was drawn via the tail at 0, 60, 90, and 120 minutes. For competition experiments, rats received an injection of hPTH 7-84 10 minutes prior to each injection of hPTH 1-84. The molar ratio of hPTH 7-84/hPTH 1-84 was 1:1.

Phosphaturic response. Normal female Sprague-Dawley rats weighing 225 to 250 g were prepared for clearance studies under light anesthesia. Polyethylene catheters (PE50) were placed in the femoeral artery for the collection of blood and measurement of blood pressure (Blood Pressure Analyzer; Micro-Medic, Inc., Louisville, Ky., USA), in the femoral vein for infusion and in the bladder for the collection of urine. Rats were placed in Plexiglas® holders and allowed to recover from the effect of the anesthetic for one hour. A priming dose (0.6 mL) of chemical inulin in saline was administered over a period of three minutes to achieve a plasma inulin level between 50 and 100 mg/mL. A solution of saline containing inulin to maintain this level and calcium gluconate to deliver 0.5 mg. Calcium was infused at the rate of 0.03 mL/min. After equilibration, a total of four 30-minute urine collections was obtained.

To assess the effect of hPTH 1-84 on phosphate excretion, urine was collected during two control periods, after which rats received a priming bolus of 1.8 μg of hPTH 1-84 followed by a sustained infusion that delivered a total of 8.2 μg of I-PTH. After an equilibration period of 20 minutes, two 30-minute urine collections were obtained. In competition experiments, hPTH 7-84 was given five minutes prior to hPTH 1-84 at a molar ratio of 4:1.

Blood samples and blood pressure measurements were recorded at the beginning and end of the baseline period, at the beginning of the PTH infusion period, and at the end of the study. The concentration of inulin in plasma and urine was determined by the method of Fuhr, Kaczmarczyk, and Kruttgen, *Klin Wochenschr,* 33:729-730 (1955). The estimation of the glomerular filtration rate (GFR) by inulin clearance and the calculation of the fractional urinary excretion rate of phosphorus ($FE_{PO4}$) were performed in the standard fashion. Blood samples were centrifuged, and plasma phosphorus and calcium concentrations were measured.

3. Serum Chemistries

Total plasma calcium levels were determined using an atomic absorption spectrophotometer (model 1100B; Perkin Elmer, Norwalk, Conn., USA). Plasma phosphorus levels were determined using an autoanalyzer (COBAS MIRA Plus; Roche, Newark, N.J., USA).

4. Statistical Analysis

Results are expressed as mean±SEM. N indicates the number of samples. The paired t-test was employed to examine statistical significance, unless otherwise indicated in the text.

J. Specificity of IRMA Assays for hPTH 1-84

Figure 13:
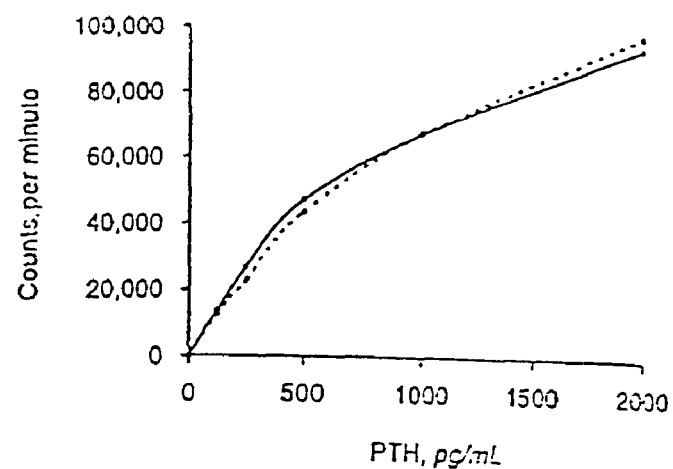
FIG. 13 illustrates comparison of the recognition of hPTH 1-84 and hPTH 7-84 by the Nichols I-PTH assay. The Nichols I-PTH assay does not differentiate between hPTH 1-84 (solid line) and hPTH 7-84 (dashed line).

Initial studies compared the ability of the Nichols Intact (I-Nichols) PTH assay and the new Whole PTH assay to discriminate between the hPTH 1-84 and hPTH 7-84 molecules. FIG. 13 shows that the Nichols "intact" PTH assay did not discriminate between human PTH 1-84 and 7-84. However, as depicted in FIG. 14, studies performed using the Whole PTH assay show that hPTH 1-84 was detected with a high degree of sensitivity, whereas hPTH 7-84 was undetectable, even at a concentration as high as 10,000 pg/mL.

1. Studios in vitro

The results of cAMP production by ROS/17.2 cells exposed to hPTH 1-84 or hPTH 7-84 are shown in FIG. 15. Unlike hPTH 7-84, hPTH 1-84 increased cAMP production in a does-dependent manner. hPTH 1-84 ($10^{-8}$ mol/L) increased intracellular cAMP from 18.1±1.25 to 738±4.13 nmol/well. On the other hand, the same concentration of hPTH 7-84 had no effect on cAMP (N=6).

2. Studies in vivo in Rats

Figure 12:
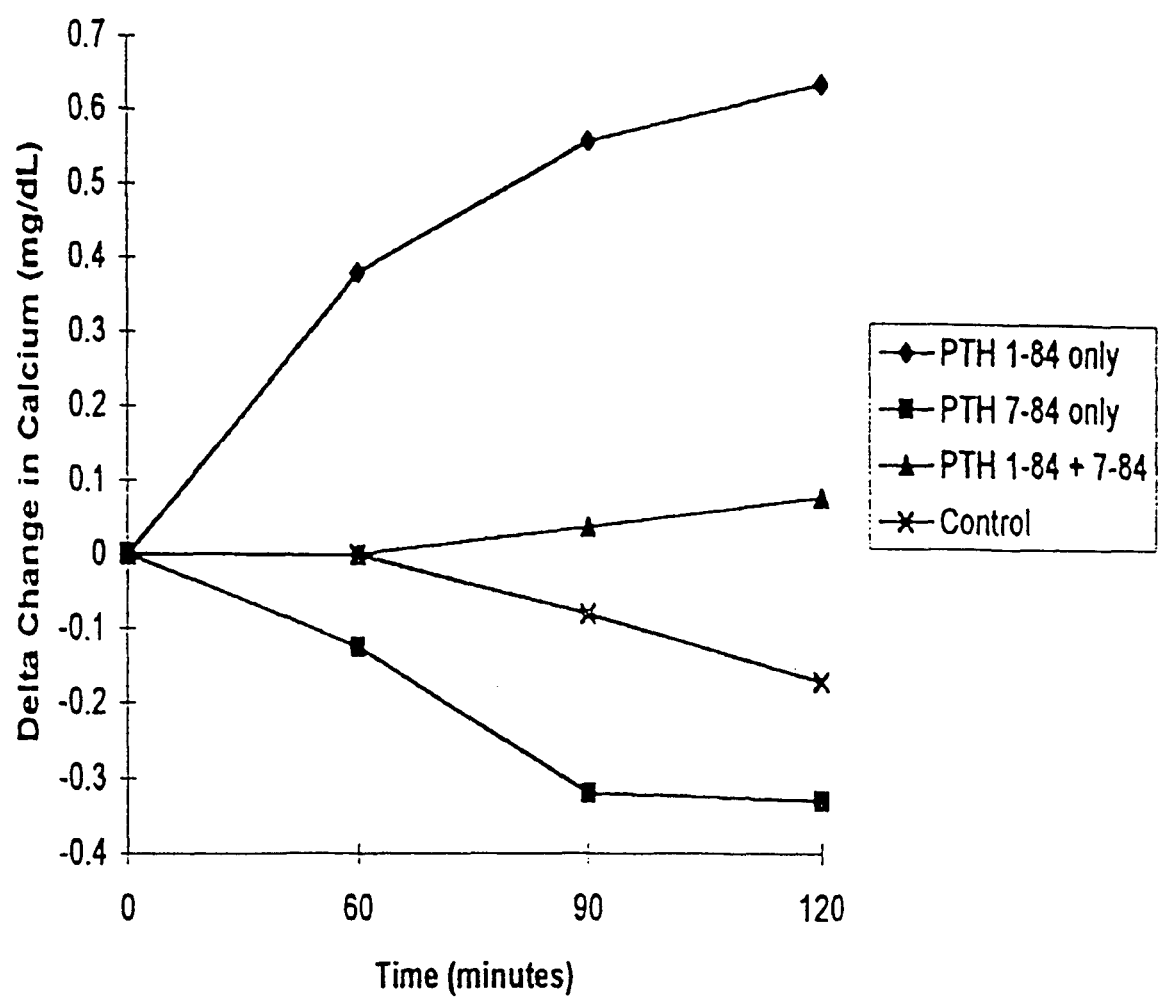
FIG. 12 is a graph demonstrating how PIN is an in vivo inhibitor of wPTH.

We next examined the hPTH 7-84 fragment as a potential competitive inhibitor of hPTH 1-84 in bone by measuring changes in serum calcium in PTX rats. FIG. 12 shows that the administration of hPTH 1-84 to PTX rats fed a 0.02% calcium diet increased plasma calcium by 0.65±0.10 mg/dL (N=9, P.<0.001, ANOVA). With the administration of vehicle alone, plasma calcium changed slightly in accordance with PTX (−0.17±0.10 mg/dL, N=5). A slight but significant decrease was observed in the rats receiving hPTH 7-84 (0.30±0.08 mg/dL, N=5, P<0.05). When both peptides were given together in a 1:1 molar ratio, the calcemic response induced by the administration of hPTH 1-84 alone decreased by 94% (N=6, P<0.001, ANOVA. Thus in this model, hPTH 7-84 significantly inhibits hPTH 1-84 induction of bone calcium mobilization.

The phosphaturic effects of these two peptides were then evaluated (FIG. 16). The GFR did not change in rats infused with hPTH 1-84 (1.8±0.3 vs. 1.8±0.1 mL/min), whereas fractional excretion of phosphate ($FE_{PO4}$) increased from 11.9±2.4 to 27.7±2.4% (N=10, P<0.001). When hPTH 7-84 was given simultaneously with hPTH 1-84, the GFR increased from 2.1±0.1 to 2.6±0.2 mL/min (N=8, P<0.05). However, despite this increase in GFR, the increase in $FE_{PO4}$ induced by treatment with hPTH 1-84 was significantly decreased by 50.2% (P<0.01). by virtue of the co-administration of hPTH 7-84.

3. Studios in Humans

FIG. 17 shows that the values for plasma PTH were higher in all 28 patients on chronic dialysis when measured with the I-Nichols assay compared with the Whole assay. The median PTH values were 523 versus 344 pg/ml (P<0.001), respectively. A regression analysis of these data is shown in FIG. 7.

The association between plasma levels of non-(1-84) PTH, "likely" hPTH 7-84, and plasma calcium and phosphorus was next examined in 20 patients maintained on chronic dialysis (FIG. 18). There was a positive correlation between the percentage of non-(1-84) PTH and serum calcium (P<0.002), but no correlation with plasma phosphorus (data not shown). These studies were performed only in those patients in whom there were values for calcium, phosphorous, and PTH from the same blood sample [20].

In a group of 14 renal transplant patients the percentage of non-(1-84) PTH was found to be 44.1±3.1% of the total PTH, as measured by the I-Nichols assay and the Whole PTH assay (FIG. 19). The absolute PTH value with the I-Nichols assay was 132.9±39.9 compared with 79.8±24.8 pg/mL (P<0.005) with the Whole PTH assay.

Finally, we examined whether intracellular cleavage of the hPTH 1-84 molecule occurs in the parathyroid gland, thus producing the non (1-84) PTH fragment. Surgically excised parathyroid glands from six uremic patients maintained on chronic dialysis were studied. FIG. 20 shows that non (1-84) PTH fragments exist in the cell lysates from these parathyroid glands and represent 41.8±3.2% (P<0.05) of the total intracellular PTH measured by the "intact" PTH assay (that is, 1-84 PTH and most likely 7-84 PTH).

The ordinarily skilled artisan can appreciate that the present invention can incorporate any number of the preferred features described above.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

Citation of the above publications or documents is not intended as an admission that any of the foregoing is pertinent prior art, nor does it constitute any admission as to the contents or date of these publications or documents.

What is claimed is:

1. A multiple antigenic peptide (MAP), which MAP comprises a branched oligolysine core conjugated with a plurality of the PTH peptide selected from the group consisting of $PTH_{2-5}$, $PTH_{2-6}$, $PTH_{2-8}$, $PTH_{2-9}$, $PTH_{2-11}$, $PTH_{2-13}$, $PTH_{2-16}$, $PTH_{2-17}$, $PTH_{2-18}$, $PTH_{2-19}$, $PTH_{2-20}$, $PTH_{2-21}$, $PTH_{2-22}$, $PTH_{2-23}$, $PTH_{2-24}$, $PTH_{2-25}$, $PTH_{2-26}$, $PTH_{2-27}$, $PTH_{2-30}$, $PTH_{2-31}$, $PTH_{2-32}$, and $PTH_{2-33}$.

2. The MAP of claim 1, wherein the branched oligolysine core comprises 3, 7 or 15 lysine residues.

3. The MAP of claim 1, wherein the plurality of the PTH peptide is conjugated to the branched oligolysine core via a spacer.

4. The MAP of claim 3, wherein the spacer is an amino acid residue.

5. The MAP of claim 3, which comprises 4, 8 or 16 copies of the PTH peptide.

6. The MAP of claim 1, wherein the plurality of the PTH peptide comprises same or different PTH peptides.

7. A method for producing an antibody to a parathyroid hormone (PTH) or a PTH peptide, which method comprises:
   a) introducing a MAP of claim 1 to a mammal in an amount sufficient to produce an antibody to a PTH peptide comprised in said MAP; and
   b) recovering said antibody from said mammal.

8. An antibody to a PTH or a PTH peptide produced by the method of claim 7.

9. A kit for producing an antibody to a parathyroid hormone (PTH) or a PTH peptide, which kit comprises:
   a) a MAP of claim 1;
   b) means for introducing said MAP to a mammal in an amount sufficient to produce an antibody to a PTH peptide comprised in said MAP; and
   c) means for recovering said antibody from said mammal.

* * * * *

SEQUENCE LISTING

<160> NUMBER OF SEQ ID NOS: 7

<210> SEQ ID NO 1
<211> LENGTH: 84
<212> TYPE: PRT

<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
        50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 2
<211> LENGTH: 84
<212> TYPE: PRT
<213> ORGANISM: Rat

<400> SEQUENCE: 2

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
                20                  25                  30

Asn Phe Val Ser Leu Gly Val Gln Met Ala Ala Arg Glu Gly Ser Tyr
            35                  40                  45

Gln Arg Pro Thr Lys Lys Glu Asp Asn Val Leu Val Asp Gly Asn Ser
        50                  55                  60

Lys Ser Leu Gly Glu Gly Asp Lys Ala Asp Val Asp Val Leu Val Lys
65                  70                  75                  80

Ala Lys Ser Gln

<210> SEQ ID NO 3
<211> LENGTH: 84
<212> TYPE: PRT
<213> ORGANISM: Mouse

<400> SEQUENCE: 3

Ala Val Ser Glu Ile Gln Leu Met His Asn Leu Gly Lys His Leu Ala
1               5                   10                  15

Ser Val Glu Arg Met Gln Trp Leu Arg Arg Lys Leu Gln Asp Met His
                20                  25                  30

Asn Phe Val Ser Leu Gly Val Gln Met Ala Ala Arg Asp Gly Ser His
            35                  40                  45

Gln Lys Pro Thr Lys Lys Glu Glu Asn Val Leu Val Asp Gly Asn Pro
        50                  55                  60

Lys Ser Leu Gly Glu Gly Asp Lys Ala Asp Val Asp Val Leu Val Lys
65                  70                  75                  80

Ser Lys Ser Gln

<210> SEQ ID NO 4
<211> LENGTH: 84
<212> TYPE: PRT
<213> ORGANISM: Bovine

<400> SEQUENCE: 4

Ala Val Ser Glu Ile Gln Phe Met His Asn Leu Gly Lys His Leu Ser

```
                 1               5                  10                 15
Ser Met Glu Arg Val Glu Trp Leu Arg Lys Lys Leu Gln Asp Val His
                20                 25                 30

Asn Phe Val Ala Leu Gly Ala Ser Ile Ala Tyr Arg Asp Gly Ser Ser
                35                 40                 45

Gln Arg Pro Arg Lys Lys Glu Asp Asn Val Leu Val Glu Ser His Gln
                50                 55                 60

Lys Ser Leu Gly Glu Ala Asp Lys Ala Asp Val Asp Val Leu Ile Lys
 65                 70                 75                 80

Ala Lys Pro Gln

<210> SEQ ID NO 5
<211> LENGTH: 84
<212> TYPE: PRT
<213> ORGANISM: Canine

<400> SEQUENCE: 5

Ser Val Ser Glu Ile Gln Phe Met His Asn Leu Gly Lys His Leu Ser
 1               5                  10                 15

Ser Met Glu Arg Val Glu Trp Leu Arg Lys Lys Leu Gln Asp Val His
                20                 25                 30

Asn Phe Val Ala Leu Gly Ala Pro Ile Ala His Arg Asp Gly Ser Ser
                35                 40                 45

Gln Arg Pro Leu Lys Lys Glu Asp Asn Val Leu Val Glu Ser Tyr Gln
                50                 55                 60

Lys Ser Leu Gly Glu Ala Asp Lys Ala Asp Val Asp Val Leu Thr Lys
 65                 70                 75                 80

Ala Lys Ser Gln

<210> SEQ ID NO 6
<211> LENGTH: 84
<212> TYPE: PRT
<213> ORGANISM: Porcine

<400> SEQUENCE: 6

Ser Val Ser Glu Ile Gln Phe Met His Asn Leu Gly Lys His Leu Ser
 1               5                  10                 15

Ser Leu Glu Arg Val Glu Trp Leu Arg Lys Lys Leu Gln Asp Val His
                20                 25                 30

Asn Phe Val Ala Leu Gly Ala Ser Ile Val His Arg Asp Gly Gly Ser
                35                 40                 45

Gln Arg Pro Arg Lys Lys Glu Asp Asn Val Leu Val Glu Ser His Gln
                50                 55                 60

Lys Ser Leu Gly Glu Ala Asp Lys Ala Ala Val Asp Val Leu Ile Lys
 65                 70                 75                 80

Ala Lys Pro Gln

<210> SEQ ID NO 7
<211> LENGTH: 86
<212> TYPE: PRT
<213> ORGANISM: Horse
<220> FEATURE:
<221> NAME/KEY: VARIANT
<222> LOCATION: 67
<223> OTHER INFORMATION: Xaa = Any Amino Acid

<400> SEQUENCE: 7

Lys Arg Ser Val Ser Glu Ile Gln Leu Met His Asn Leu Gly Lys His
 1               5                  10                 15
```

```
Leu Asn Ser Val Glu Arg Val Glu Trp Leu Arg Lys Lys Leu Gln Asp
            20              25              30

Val His Asn Phe Ile Ala Leu Gly Ala Pro Ile Phe His Arg Asp Gly
            35              40              45

Gly Ser Gln Arg Pro Arg Lys Lys Glu Asp Asn Val Leu Ile Glu Ser
    50              55              60

His Gln Xaa Ser Leu Gly Glu Ala Asp Lys Ala Asp Val Asp Val Leu
65              70              75              80

Ser Lys Thr Lys Ser Gln
                85
```